(12) United States Patent
Bromann et al.

(10) Patent No.: US 9,238,826 B2
(45) Date of Patent: Jan. 19, 2016

(54) METHOD FOR PRODUCING TERPENES

(75) Inventors: Kirsi Bromann, Espoo (FI); Tina Nakari-Setala, Espoo (FI); Laura Ruohonen, Helsinki (FI); Mervi Toivari, Espoo (FI); Merja Penttila, Espoo (FI)

(73) Assignee: Teknologian Tutkimuskeskus VTT Oy, Espoo (FI)

( * ) Notice: Subject to any disclaimer, the term of this patent is extended or adjusted under 35 U.S.C. 154(b) by 0 days.

(21) Appl. No.: 13/883,995

(22) PCT Filed: Nov. 14, 2011

(86) PCT No.: PCT/FI2011/051001
§ 371 (c)(1),
(2), (4) Date: Oct. 25, 2013

(87) PCT Pub. No.: WO2012/062971
PCT Pub. Date: May 18, 2012

(65) Prior Publication Data
US 2014/0045238 A1  Feb. 13, 2014

Related U.S. Application Data

(60) Provisional application No. 61/412,845, filed on Nov. 12, 2010.

(30) Foreign Application Priority Data

Nov. 12, 2010  (FI) ..................... 20106190

(51) Int. Cl.
| C07K 14/37 | (2006.01) |
| C12P 5/00 | (2006.01) |
| C07K 14/38 | (2006.01) |
| C12N 15/52 | (2006.01) |
| C12N 15/80 | (2006.01) |
| C12P 15/00 | (2006.01) |

(52) U.S. Cl.
CPC ............... *C12P 5/007* (2013.01); *C07K 14/37* (2013.01); *C07K 14/38* (2013.01); *C12N 15/52* (2013.01); *C12N 15/80* (2013.01); *C12P 15/00* (2013.01)

(58) Field of Classification Search
None
See application file for complete search history.

(56) References Cited

FOREIGN PATENT DOCUMENTS

| WO | WO 0121779 A2 | 3/2001 |
| WO | WO 0224865 A2 | 3/2002 |
| WO | WO 0240694 | 5/2002 |
| WO | WO 2006014837 A1 | 2/2006 |
| WO | WO 2007140339 A2 | 12/2007 |
| WO | WO 2008039499 A2 | 4/2008 |
| WO | WO 2010104763 A1 | 9/2010 |

OTHER PUBLICATIONS

Lim et al. Arch. Pharm. Res. (2009) 32 (9) 1237-1243.*
Tirapell et al. Pharmacy and Pharmacology (2005) 57, 997-1004.*
Bergmann S. et al. Genomics-driven discovery of PKS-NRPS hybrid metabolites from Aspergillus nidulans. Nature Chemical Biology, Apr. 2007, vol. 3 No. 4.
Database Genbank Genbank (online) Oct. 2, 2009 'TPA_reasm: Aspergillus nidulans FGSC A4 chromosome VII' NCBI & Wortman J.R. et al. The 2008 update of the Aspergillut nidulans genome annotation: a coomunity effort. Fungal Genetics and Biology, Mar. 2009, vol. 46, pp. 52-59 and 510-513.
Kimura M. et al. Molecular and genetic studies of Fusarium trichothecene biosynthesis, pathways, genes, and evolution. Bioscience Biotchnology and Biochemistry, Sep. 2007, vol. 71, No. 9.
Nicholson, M. J. et al. Identification of two aflatrem biosynthesis gene logi in Aspergillus flavus and metabolic engineering of Penicillium paxilli to elucidate their function. Applied and Environmental Microbiology, Dec. 2009, vol. 75, No. 23.
Sakai, K. et al. Construction of a citrinin gene cluster expression system in heterologous Aspergillus oryzae. Journal of Bioscience and Bioengineering, Nov. 2008, vol. 106, No. 5.
Toyomasu T. et al. Cloning of a gene cluster responsible for the biosynthesis of diterpene aphidicolin, a specific inhibitor of DNA polymerase alpha. Bioscience Biotechnology and Biochemistry, Jan. 2004, vol. 68, No. 1.
Galagan James E et al: Sequencing of Aspergillus nidulans and comparative analysis with A-fumigatus and A-oryzae. Nature, vol. 438, No. 7071, Jan. 12, 2005.

* cited by examiner

*Primary Examiner* — Nashaat Nashed
(74) *Attorney, Agent, or Firm* — Sughrue Mion, PLLC

(57) ABSTRACT

The present invention relates to a method for producing terpenes in fungi, wherein a terpene biosynthetic gene cluster having terpene biosynthetic genes and regulatory regions operably linked to said genes is activated. The invention relates also to a terpene biosynthetic gene duster and regulatory regions of such terpene biosynthetic gene cluster usable is production of terpenes, use of regulator for regulating the terpene production and use of *Aspergillus nidulans* FGSC A4 for producing terpenes. The method of invention provides higher yields of enriched terpene product without essential amount of side-products.

11 Claims, 9 Drawing Sheets

METHOD FOR PRODUCING TERPENES

This Application is a National Stage Entry of PCT/FI2011/051001, filed Nov. 14, 2011, which claims the benefit of U.S. Provisional Application No. 61/412,845, filed Nov. 12, 2010, and which claims priority to Finnish Patent Application No. 20106190, filed Nov. 12, 2010.

FIELD OF THE INVENTION

This invention relates to a method for producing terpenes in fungi, a terpene biosynthetic gene cluster, regulatory regions of such terpene biosynthetic gene cluster, use of transcription factor for regulating the terpene production and use of *Aspergillus nidulans* FGSC A4 for producing terpenes.

DESCRIPTION OF RELATED ART

Terpenes are a large group of compounds that have many pharmaceutical and industrial applications. Terpenes can function as potential drugs or precursors for pharmaceuticals or bioactive compounds. Examples for these applications are antimalarial sesquiterpene amorphadiene and anticancer diterpene taxol. Monoterpenes, such as limonene, have applications as jet fuel components.

Bioactive terpenes are commonly purified from plants. Terpenes are a class biologically produced molecules synthesized from five carbon precursor molecules in a wide range of organisms. Terpenes are pure hydrocarbons, while terpenoids may contain one or more oxygen atoms. The terms terpene and terpenoid are used interchangeably. Problem in the industrial scale production of terpenoids is their structural complexity which makes them expensive to produce by the means of conventional chemistry. Another concern is the environmental stress caused by terpene purification from harvested plant material. One way to go around these problems is to generate microbial hosts that are easily cultured in industrial conditions. There is an increasing demand for inexpensive production methods for terpene derived pharmaceuticals. Heterologous expression organisms such as bacteria, yeasts, or fungi, would provide the sought-after cost-efficient way to produce these compounds. One of the problem areas in genetically engineered fungal hosts is the product outcome of exogenous genes.

Genes encoding successive steps in a biosynthetic pathway tend to be clustered together on the chromosome to form "gene clusters". The extent of the clustering is highly variable within and between organisms. Secondary metabolites are compounds that are not essential for the normal growth of an organism but that function as defense compounds or signaling molecules in ecological interactions. Many secondary metabolites have interesting biological properties, for example as antibiotics, anticancer agents, insecticides, immunosuppressants and herbicides. Clustering of the genes controlling the biosynthesis of these compounds in bacteria is virtually universal. However, eukaryotic genomes also contain clusters of functionally related but non-homologous genes [Osborn].

Numerous clusters for the synthesis of secondary metabolites can be found in filamentous fungi. Filamentous organisms contain far more clusters of genes for secondary metabolite biosynthesis than had been predicted from the previously identified metabolites. Secondary metabolic gene clusters are self-contained cassettes for metabolite production. They contain genes encoding enzymes that give rise to the skeleton structures of the different classes of secondary metabolite e.g. non-ribosomal peptide synthetase (NRPS) enzymes, polyketide synthases (PKSs), and terpene synthases, which are referred to as 'signature' genes/enzymes. The clusters also contain genes for tailoring enzymes that modify the secondary metabolite skeleton, such as oxidoreductases, methyltransferases, acyltransferases and glycosyltransferases. In some cases secondary metabolic clusters also include genes for pathway-specific regulators and/or for resistance to the pathway end-product [Osborn].

Expression of secondary metabolic clusters is typically under environmental and/or developmental control and is mediated by complex regulatory cascades that relay signals to the pathway-specific switches. The Zn(II)2Cys6-type transcription factors function as pathway-specific activators of secondary metabolite clusters by upregulating the transcription of the clustered genes. Clustering of secondary metabolite genes has the potential to facilitate regulation at the higher level of chromatin. The specific order and position of the genes within some secondary metabolite clusters could provide a structural framework that help to determine the timing and order of gene activation. This process has been proposed to orchestrate sequential substrate channeling through the enzymatic steps in the pathway (Roze et. al.) The main selective advantage for clustering of functionally related genes is the need to coregulate a set of genes controlling successive steps in a biosynthetic or developmental pathway. Clustering facilitates the optimal regulation of a set of biosynthetic genes.

It has been shown that intergenic regions and the chromosomal positioning play a part in optimal gene expression. Many secondary metabolite clusters are in the subtelomeric regions of chromosomes, where the heterochromatin transcription is positionally regulated. Some of the clusters residing in subtelomeric regions are shown to be regulated by the universal transcriptional activators such as LaeA or AreA, which react to the environmental stimuli to release the heterochromatin regions for translation. The transcription of the genes in these areas is silenced under normal conditions. When exogenous genes are randomly integrated into the genome of the host organism, positional transcription regulation can play a role in the gene expression of the target gene (Palmer et al).

Apart from unforeseen pleiotropic effects due to gene disruption by randomly integrated transforming DNA, it has been suggested that certain chromosomal locations may be more favorable for heterologous expression than others, perhaps due to specific interaction with local regulatory elements, or more generally active native transcription in the neighbourhood of normally highly expressed genes (Davis et al.). Certain spatially or temporally regulated *Aspergillus* genes—e.g., the aflatoxin cluster (Chiou et al.) and conidium-specific genes (Miller et al.) show dramatic changes in regulatory response when displaced from their original locus, and locus effects on heterologous expression have also been reported (Verdoes et al.).

In the paper published by Lubertozzi & Kiesling amorphadiene synthase gene from *Artemisia annua* was transformed into *Aspergillus nidulans*. In their approach the product specificity was greatly reduced in *Aspergillus nidulans* compared to the same expression experiments in *E. coli*. The reason for this was hypothesized to be interfering background activity of other *Aspergillus nidulans* secondary metabolite genes, which are absent in *E. coli*, or the lack of supporting enzymatic activities needed for the modification of the terpenoid carbon skeleton to amorphadiene.

Bok et al. discloses that over-expression of LaeA in *Aspergillus nidulans* induces numerous secondary metabolite clusters including putative terpenoid clusters.

WO 2002024865 (Holzman) describe modulation of lovastatin production using a Zn2(II)Cys6-transcriptional activator residing outside the lovastatin cluster.

WO 2001 021779 (DSM) discloses an identification, cloning and over-expression of a cluster-specific transcription activator BlaR activating β-lactam production in filamentous fungus.

WO 1999 025735 describe over-expression of chimeric transcription factors to enhance production of secondary metabolites.

Sakai et al. have introduced citrinin biosynthetic gene cluster of *Monascus* into *Aspergillus oryzae*. They were able to increase the citrinin production by further introducing multiple copies of activator gene ctnA controlled by *Aspergillus* trpC promoter.

Chiang et al. have been able to activate an otherwise silent polyketide cluster in *Aspergillus nidulans* by replacing the promoter of the transcription activator with an inducible promoter.

WO 2010104763 discloses the production of terpenes and terpenoids using a nucleic acid encoding a terpene synthase. This is carried out by the expression of biosynthetic genes that are not part of a single naturally occurring gene cluster, but are artificially linked to heterologous regulatory regions (promoters). The genes described in this invention are not activated by a transcription factor.

Similarly, WO 2008039499 discloses a nucleic acid comprising a nucleotide sequence encoding a terpene synthase, WO 0240694 discloses an expression vector comprising specifically the taxane synthesis pathway, and WO 2007140339 discloses the production of isoprenoids via a biosynthetic pathway.

Thus, biosynthetic pathways for the production of terpenes are known. However, none of the cited publications disclose overexpression of a transcription factor specifically activating a cluster of genes belonging to a terpene biosynthetic pathway.

Drawback in the prior-art solution is difficulty in obtaining high product yields for terpenes. Further drawback is that the products obtained by microbial fermentation typically contain a major amount of unspecific side products and other unwanted compounds. In conclusion there is a need for production processes of terpenes giving higher yields of enriched product without essential amount of side-products.

OBJECTS AND SUMMARY OF THE INVENTION

It is an aim of the invention to provide a method for producing terpenes by microbial fermentation so that the yield of the product is improved and the product is enriched. Particularly, the aim is to provide a method in which the intrinsic transcriptional regulation capacity of the fungus is used to keep the transcriptional regulation of terpene producing genes at a high level to produce commercially valuable terpene compounds in a microbial host.

These and other objects are achieved by the present invention as hereinafter described and claimed.

The first aspect of the invention is a method for producing terpenes in fungi. According to invention the method comprises the steps of:
(a) providing a transcription factor activating a terpene biosynthetic gene cluster having terpene biosynthetic genes and regulatory regions operably linked to said genes;
(b) operably linking said transcription factor to a promoter;
(c) transforming the transcription factor of item (a) operably linked to the promoter of item (b) to a host cell carrying a terpene biosynthetic gene cluster as described in item (a);
(d) cultivating said host in conditions allowing the expression of the transcription factor activating the cluster; and optionally
(e) recovering the terpene product.

The second aspect of the invention is a terpene biosynthetic gene cluster. Characteristic to the cluster is that it essentially comprises the genes putatively encoding
(a) Zn(II)2Cys6-type transcription factor (AN1599 SEQ ID NO: 74), a terpene synthase (AN1594 SEQ ID NO: 65), an HMG-CoA reductase (AN1593 SEQ ID NO: 63), GGPP-synthase (AN1592 SEQ ID NO: 61) and
(b) optionally translation elongation factor 1-gamma (AN1595 SEQ ID NO: 67), cytochrome P450 (AN1598 SEQ ID NO: 73), short-chain dehydrogenase (AN1596 SEQ ID NO: 69), hypothetical protein with some similarity to methyltransferase (AN1597 SEQ ID NO: 71), the regulatory regions operably linked to said genes, and optionally an AAA family ATPase (AN1591 SEQ ID NO: 59) and
(c) regulatory regions operably linked to the genes of item (a) and to the optional genes of item (b).

Zn(II)2Cys6-type transcription factor is capable of regulating all pathway genes residing within the terpene biosynthetic gene cluster. Transcription factors originally residing within the cluster or close to the cluster are preferred as they can be easily identified. However, after transformation to the homologous or heterologous host the genomic location of the inserted transcription factor in relation to the cluster is not critical.

The third aspect of the invention is regulatory regions of terpene biosynthetic gene cluster as described here for production of terpenes in fungus.

The fourth aspect of the invention is use of the transcription factor characterized by SEQ ID NO: 1, or a sequence showing at least 80% identity to one of those for regulating the terpene production. In a preferred embodiment the degree of identity to SEQ ID NO: 74 is 82%, 85%, 87%, 90%, 92%, 95%, 98% or even 99%.

The fifth aspect of the invention is the use of *Aspergillus nidulans* FGSC A4 (Glasgow wild type, Fungal Genetic Stock Center strain A4) for producing terpenes.

The sixth aspect of this invention is a production host that is usable in the method of this invention. According to the invention the host comprises a terpene biosynthetic pathway gene cluster as described above and an introduced transcription factor operably linked to a promoter, wherein the transcription factor is capable of activating a terpene biosynthetic gene cluster. An introduced transcription factor operably linked to a promoter used in this connection means that the host cell carries (in addition to possible endogenous transcription factor and promoter) further copy or copies of transcription factor operably linked to a promoter when compared to a host that is not tailored for use within scope of this invention. The introduced transcription factor and the promoter can be homologous or heterologous to the host.

Seventh aspect of this invention is a process for production of terpenes. According to the invention the method comprises cultivating a production host useful in the method described here and optionally recovering the product.

So called "AN1599-transformant" or "AN1599-transformant strain" described herein is *Aspergillus nidulans* strain FGSC A4 that has been transformed to carry extra copies of a Zn(II)2Cys6 transcription factor AN1599 (SEQ ID NO: 74) gene under a constitutively active gpdA-promoter. The exogenous gene product (SEQ ID NO: 10) is linearized with PciI and transformed into the genome of the host strain. The integration site and the copy number of the expression construct are not known.

The embodiments of the invention are disclosed in the dependent claims.

DESCRIPTION OF THE PREFERRED EMBODIMENTS OF THE INVENTION

Figure 1:
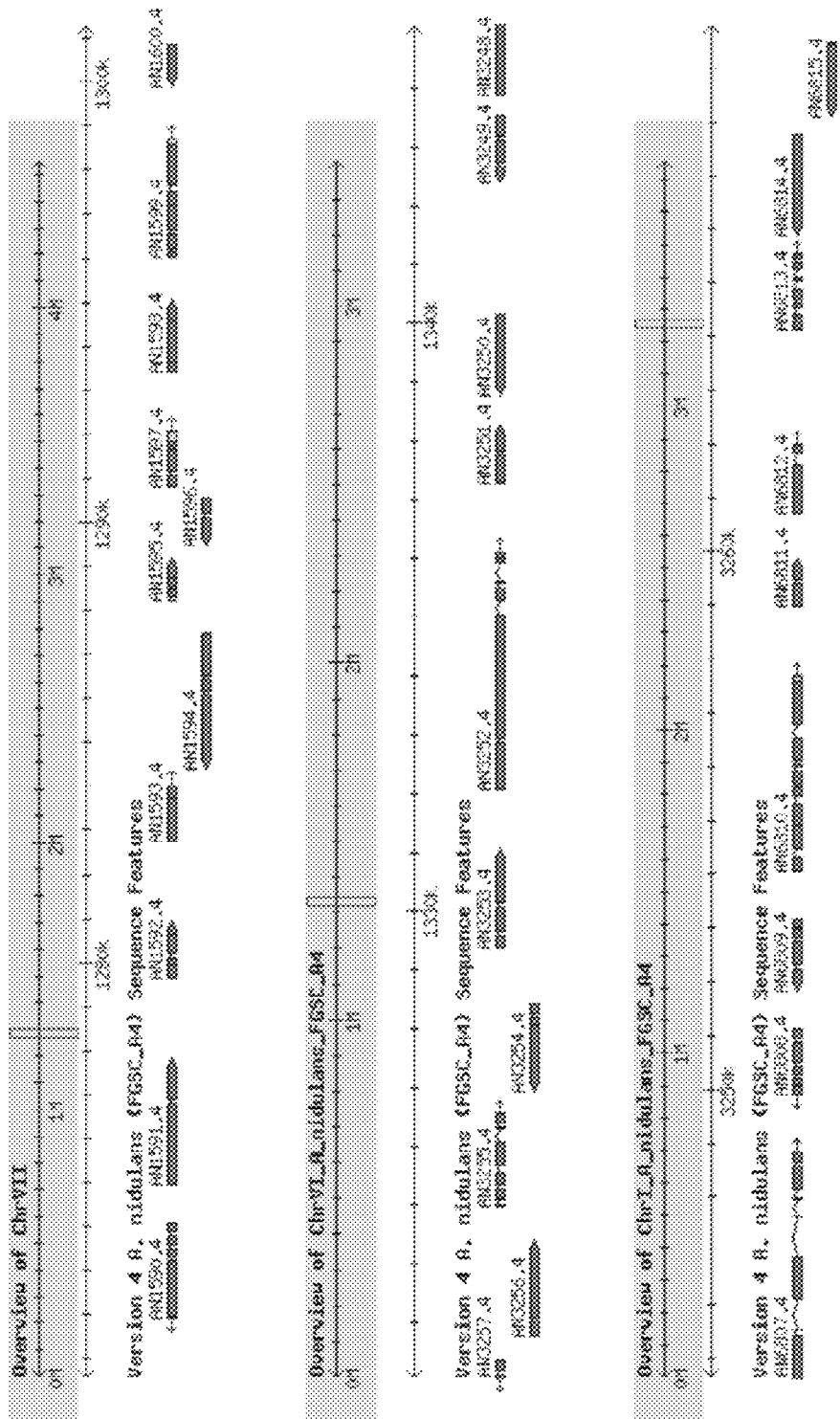
FIG. 1. Chromosomal areas of predicted terpene synthase clusters. Pictures adapted from *Aspergillus* Genome Database (Arnaud et al.) using Genome Browser tool.

This invention describes the use of naturally occurring regulatory regions operably linked to biosynthetic genes that are activated by a single transcription factor and lead to production of terpene via several enzymatic reactions. These enzymes are coded by cluster genes.

Thus, the invention relates to a method for the modulation of secondary metabolite production of fungi through genetic manipulation of such fungi. Disclosed is a method using zinc binuclear cluster, Zn(II)2Cys6, -protein to significantly increase useful secondary metabolite production. The term zinc binuclear cluster protein (ZBC-protein) means any gene encoding a protein having as part of its structure Cys-(Xaa) 2-Cys-(Xaa)6-Cys-(Xaa)5-16-Cys-(Xaa)2-Cys-(Xaa)6-8-Cys. Generally, the methods according to the invention comprise expressing a zinc binuclear cluster protein in a fungus. $Zn(II)_2Cys_6$-type transcription factors have a well-conserved cysteine rich domain that binds two zinc atoms. This DNA binding domain recognizes CGG triplets in varying orientations within the promoter region of the target genes.

AN1599 polypeptide is a species of ZBC-protein and capable of acting as a pathway specific transcription factor for the production of ent-pimara-8(14),15-diene compound in a microorganism. It is characterized by an amino acid sequence comprising at least a part of SEQ ID NO: 74.

In this invention an activation of upstream crucial precursor synthesis genes, HMG-CoA reductase for isoprenoid synthesis and GGPP-synthase for the diterpenoid backbone synthesis, as well as enzymes needed for the modification of the final product is provided. By overexpressing transcriptional activator we can achieve optimal expression levels for all necessary genes in the pathway.

Function of the genes residing in the cluster was predicted using homology searches with BLAST and pfam software programs. HMG-CoA reductase is the rate-limiting enzyme needed for the production of the isoprenoid precursors in the mevalonate pathway. GGPP-synthase combines isoprenoid moieties to form a precursor for diterpenoid backbone. The terpene synthase gene coding for ent-kaurene/ent-copalyl type synthase performs two sequential cyclisation steps to first form ent-copalyl diphosphate from GGPP precursor, and then diterpene compound pimaradiene from the ent-copalyl diphosphate. Cytochrome P450, short-chain dehydrogenase and the hypothetical protein residing in the cluster may function as decorative enzymes performing oxidation/reduction reactions and additions of functional groups to the diterpene structure. Translation elongation factor 1-gamma plays a central role in the elongation cycle during protein biosynthesis. Members of the AAA+ATPases function as molecular chaperons, ATPase subunits of proteases, helicases, or nucleic-acid stimulated ATPases. The AAA+proteins contain several distinct features in addition to the conserved alpha-beta-alpha core domain structure and the Walker A and B motifs of the P-loop NTPases.

Expression cassette, which is encoding a selectable marker gene and a transcriptional regulator AN1599 polypeptide operably linked to a promoter and a terminator, is useful for improving the production of terpenes, especially pimaradiene compounds in a microorganism such as filamentous fungus, e.g. *Aspergillus nidulans, Aspergillus niger, Neosartorya fisheri, Microsporum canis* or *Trichoderma reesei*, by transforming the organism with the expression cassette comprising a transcription factor operably linker to a promoter and a terminator, and selecting the transformed cells with the selectable marker and an increased production of terpene compound as compared to non-transformed cells. Transformed host, which is a terpene producing microorganism, is useful for producing terpene compound by fermentation, and the terpene compound can optionally be isolated from the cells or the growth medium. Terpene product can be any terpene, diterpenes are preferred and ent-pimara-8(14),15-diene is the most preferred terpene product.

In one embodiment of the invention terpenes or terpenoids are produced in fungi by activating a terpene pathway. Basic idea is to overexpress a positive transcription factor specifically activating a cluster of genes belonging to a terpene, for example pimaradiene, biosynthetic pathway. Transcriptional upregulation of the complete gene cluster will overcome the challenges of introducing multiple overexpression constructs for individual biosynthetic pathway genes into a single host organism. Compared to the traditional systems, where multiple genes are exogenously introduced to a host and upregulated, this approach benefits from the specific transcriptional activator capable of upregulating all necessary genes for the production of a diterpene compound in the host organism. It has been noted, that a product outcome of an organism with multiple exogenous genes will rely on the individual expression levels of each introduced gene. Balancing the expression levels to achieve optimal product yield can be tricky. Optimizing expression for multiple exogenous genes at the same time will in many cases create a so-called bottleneck effect, where insufficient transcriptional activation of one gene will limit the product yield no matter how high upregulation is achieved for the rest of the genes in the pathway. When multiple biosynthetic pathways with similar end products are activated, existing precursor pool is guided to the biosynthetic pathway of the synthase gene with the highest expression level. Thus downregulation of competing pathways can be beneficial in guiding the product flux toward the desired compound. The holistic changes in the transcriptome of the host can be seen in our DNA array study which revealed downregulation of multiple other secondary metabolite synthase clusters when the terpene cluster was activated (results shown in FIG. 10). This enables the production of enriched diterpene product with only minor amount of side products in the AN1599 transformant. Concentrated main product and high yield provide an excellent material for industrial use and possible further purification for intended applications.

In this connection term terpenes means hydrocarbons built from isoprene units ($CH_2=C(CH_3)-CH=CH_2$). Terpene hydrocarbons therefore have molecular formulas ($C_5H_8)_n$, and they are classified according to the number of isoprene units: hemiterpenes, monoterpenes, sesquiterpenes, diterpenes, triterpenes, and tetraterpenes. In one embodiment the terpenes are terpenoids, which are terpenes with modifications in their carbon skeleton, and especially diterpenoids. In one embodiment the terpenes are pimaradienes. Ent-pimara-8(14),15-diene and its derivatives are preferred embodiments. Ent-pimara-8(14),15-diene derivatives have been shown to have antitrypanosomal, antimicrobial, anti-inflammatory and antiviral activities and are known to function as Ca-channel blocker, as well as cholesterol lowering agents. Thus such products are very valuable material for pharmaceutical industry.

In this connection the phrase "conditions allowing the expression" means conditions wherein the transcription factor (for example AN1599 SEQ ID NO: 74) activating the cluster is under constitutive promoter or under inducible promoter and the micro-organism is cultured in the presence of the inducer.

In one embodiment the host cell of item carries the terpene biosynthetic gene cluster having terpene metabolite synthase genes, and wherein the transcription factor (particularly AN1599 SEQ ID NO: 74) of the gene cluster is operably linked to a suitable promoter and transformed to the cell.

In other embodiment the terpene biosynthetic gene cluster having terpene metabolite synthase genes is transformed to a host cell. The host may be heterologous or homologous to the cluster.

The transcription factor operably linked to a promoter and activating a terpene biosynthetic gene cluster having terpene biosynthesis genes, may be homologous or heterologous to the host cell and/or said gene cluster. After transformation the host strain may have one or more copies of said transcription factor and promoter.

Site-directed transformation of the transcription factor operably linked to a suitable promoter, transformation of single genes and/or transformation of a whole cluster or transformation of genes of the pathway with the regulatory regions may be preferred to block translation of the unwanted genes of the host or to enhance the transcription of the synthetic pathway genes.

In one embodiment a gene encoding a transporter protein is included to the production host. The transporter protein can be within the terpene pathway cluster, it can be natural to the host or introduced heterologous or homologous transporter. Transporter molecules represent an active transportation system through cellular membranes or for example facilitated diffusion. They can force ions or small molecules through the membranes, for example enhance secretion of terpenes. It is well understood by the skilled person that transporters may enhance the production of desired product. For example, several PDR type transporters as well as transporters of the major facilitator superfamily (MFS) were up-regulated in the artemisinic acid-producing *Saccharomyces cerevisiae* strain. These transporters may enhance the export of the terpene product (Ro et al).

With the DNA array experiment, we noticed that the transcription of numerous transporters and transferases is upregulated in the AN1599 transformant-strain where terpene biosynthetic pathway is activated (data not shown). Efficient transport of precursors and end products will likely be beneficial for the production of secondary metabolites in fungi.

Transcription factor (for example AN1599 SEQ ID NO: 74) can activate the terpene biosynthetic pathway by activating the pathway genes (upregulation). The upregulation of the cluster genes by transcription factor (for example AN1599 SEQ ID NO: 74) may also be associated with downregulation of other secondary metabolite clusters. Other secondary metabolite pathways might be competing for the precursor pool needed for the terpene biosynthesis. Hence, the downregulation of potentially competing clusters is an advantage for the specific production of the activated cluster compound.

In this connection the transcription factor (for example AN1599 SEQ ID NO: 74) is capable of upregulating the whole terpene pathway. Activation of the pathway increases the amount of desired final product and decreases impurities including intermediates. The location of the transcription factor, such as AN1599 (SEQ ID NO: 74), is not restricted. In one embodiment the transcription factor and the promoter are transformed to the host cell randomly, in another embodiment the transformation is site-directed. Thus the production host will have a native transcription factor within the cluster, and another copy(/ies) of the said transcription factor operably linked to a promoter located elsewhere in the genome.

The N-terminal region of a number of fungal transcription factors contain a cysteine-rich motif that is involved in zinc-dependent binding of DNA. The region forms a binuclear Zn cluster, in which two Zn atoms are bound by six Cys residues. Amino acids 45-86 in the transcription factor AN1599 (SEQ ID NO: 74) form a conserved Zn(II)2Cys6 DNA-binding domain.

```
Consensus sequence   haCdnCrkkKvKCda . . . kkPaCsnCkklnleCtfyse

Match                +ac++Cr +Kv+Cd+       + P C +C+k++++C++

AN1599 45-86         RACQSCRASKVRCDQPNPGMP-CLRCQKSGKPCVDAAS
```

Pfam (pfam.janelia.org/) sequence alignment for AN1599 (SEQ ID NO: 74) conserved Zn(II)2Cys6 DNA-binding domain.

In one embodiment the transcription factor has a sequence SEQ ID NO: 74, or a sequence showing at least 80% identity to SEQ ID NO: 74. In a preferred embodiment the transcription factor has a sequence characterized by SEQ ID NO: 74, or a sequence showing at least 85%, 88%, 90%, 92%, 95%, 98% identity to SEQ ID NO: 74.

The promoter should be suitable to the host and preferably effective in cultivation conditions. Typically the promoter is homologous to the production host but also heterologous promoter can be used. The promoter can be a constitutive or an inducible promoter. An inducible promoter is especially advantageous when the final product or one or more of the intermediates is (are) harmful or toxic to the production host and controlled expression is preferred. Examples of suitable constitutively active promoters are promoters such as *Aspergillus nidulans* glyceraldehyde-3-phosphate dehydrogenase (gpdA), and tryptophan biosynthesis gene trpC. Examples of suitable inducible promoters include nitrate reductase (niaD) promoter, alcohol dehydrogenase (alcA) promoter, acetamidase (amdS), and heterologous inducible promoters such as *Penicillium chrysogenum* endoxylanase (xylP). In one embodiment the promoter is *Aspergillus nidulans* gpdA promoter. In one embodiment the promoter is *Aspergillus* glucoamylase (glaA) promoter.

The host cell can be heterologous or homologous to one or more of the genes encoding transcription factor, promoter and the genetic cluster. Any production host can be used but preferably the host is a microbial cell such as fungus, yeast or bacterium, more preferably a fungus and still more preferably a filamentous fungus. Examples of suitable fungal host are *Aspergillus, Penicillium, Trichoderma, Neurospora, Fusarium* and *Neosartorya*. In one embodiment the host is *Aspergillus, Penicillium* or *Trichoderma* and in a preferred embodiment *Aspergillus nidulans*. Especially preferred host is *Aspergillus nidulans* homologous to the cluster. In one embodiment the host cell is *Aspergillus nidulans* FGSC A4.

In the experimental section we describe AN1599-transformant strain that is *Aspergillus nidulans* strain FGSC A4 that has been transformed to carry extra copies of a Zn(II)2Cys6 transcription factor AN1599 (SEQ ID NO: 74) gene under a constitutively active gpdA-promoter. The exogenous gene product (SEQ ID NO:10) is linearized with PciI and transformed into the host genome of the host strain. The integration site and the copy number of the expression construct are not known.

Transformation and selection of transformants can be performed by methods known in the art. One example is transformation by protoplasting and selection using glufosinate ammonium. Stable transformation is obtained when the expression cassette is integrated to the chromosomal DNA of the host. However, also episomal plasmids and other non-integrated constructs are within this invention.

A gene cluster is a set of two or more genes that serve to encode proteins needed for the biosynthesis of a product. In one embodiment of the invention the terpene biosynthetic gene cluster is obtained from species *Aspergillus, Neosartorya* or *Microsporus*, preferably *Aspergillus nidulans*, *Aspergillus niger, Neosartorya fischeri* or *Microsporum canis*. *Aspergillus nidulans* and especially *Aspergillus nidulans* FGSC A4 are most preferred.

In another embodiment the cluster comprises essentially the genes encoding proteins characterized by SEQ ID NO: 74 or a sequence having at least 80%, preferably at least 85%, 90%, 95% or even 98% degree of identity to SEQ ID NO: 74 (AN1599), or an active fragment thereof.

SEQ ID NO: 65 or a sequence having at least 88%, 90%, 95% or even 98% degree of identity to SEQ ID NO: 65 (AN1594), or an active fragment thereof.

SEQ ID NO: 63 or a sequence having at least 90%, preferably at least 95%, 97% or even 98% degree of identity to SEQ ID NO: 63 (AN1593), or an active fragment thereof.

SEQ ID NO: 61 or a sequence having at least 86%, preferably at least 90%, 95%, 97% or even 98% degree of identity to SEQ ID NO: 61 (AN1592), or an active fragment thereof.

SEQ ID NO: 67 or a sequence having at least 90%, preferably at least 93%, 95%, 97%, 98% or even 99% degree of identity to SEQ ID NO: 67 (AN1595), or an active fragment thereof.

SEQ ID NO: 73 or a sequence having at least 94%, preferably at least 95%, 97% or even 98% degree of identity to SEQ ID NO: 73 (AN1598), or an active fragment thereof.

SEQ ID NO: 69 or a sequence having at least 90%, preferably at least 93%, 95%, 97%, 98% or even 99% degree of identity to SEQ ID NO: 69 (AN1596), or an active fragment thereof.

SEQ ID NO: 71 or a sequence having at least 90%, preferably at least 93%, 95%, 97%, 98% or even 99% degree of identity to SEQ ID NO: 71 (AN1597), or an active fragment thereof and optionally SEQ ID NO: 59 or a sequence having at least 50%, preferably at least 60%, 70%, 75%, 80%, 85%, 90% or even 95% degree of identity to SEQ ID NO: 59 (AN1591) or an active fragment thereof, and regulatory regions operably linked to said genes.

In another embodiment the cluster comprises the genes encoding proteins as listed and characterized above. In still further embodiment the cluster comprises the genes encoding proteins (AN1599 SEQ ID NO: 74), (AN1594 SEQ ID NO: 65), (AN1593 SEQ ID NO: 63), (AN1592 SEQ ID NO: 61), (AN1595 SEQ ID NO: 67), (AN1598 SEQ ID NO: 73), (AN1596 SEQ ID NO: 69), and (AN1597 SEQ ID NO: 71) as listed and characterized above.

"An active fragment" means a fragment having all the parts needed for completing the function typical for the protein.

In this connection the phrase "comprises essentially" means that at least genes encoding the proteins needed for terpene production are included. In this connection at least genes encoding Zn(II)2Cys6-type transcription factor (AN1599 SEQ ID NO: 74), a terpene synthase (AN1594 SEQ ID NO: 65), an HMG-CoA reductase (AN1593 SEQ ID NO: 63), GGPP-synthase (AN1592 SEQ ID NO: 61), and regulatory regions operably linked to said genes should be included. Thus, cluster fragments can also be used.

Organization of the genes within the biosynthetic pathway gene cluster is not critical, e.g. *Aspergillus nidulans* and *Neosartorya fisheri* carry the respective genes but the order of the genes is different.

Thus, any combination of cluster fragments can be used.

As used in the present context the term "identity" refers to the global identity between two amino acid sequences compared to each other from the first amino acid encoded by the corresponding gene to the last amino acid. For the purposes of the present invention identity is preferably determined by means of known computer programs using standard algorithms. An example of such a program is NCBI BLAST; BLASTp (comparison of known protein sequences, amino acids), BLASTn (comparison of nucleic acid sequences), BLASTx (comparison of translated nucleic acid sequences against know protein sequences).

In this connection the term "synthase genes" means gene(s) encoding the terpene cyclase and all genes encoding enzymes that are needed in modification of terpene. HMG-CoA reductase is the rate-limiting enzyme in the isoprenoid precursor biosynthesis, and therefore indispensable for the synthesis of terpenes. Sufficient synthesis of precursor molecules critically impacts the yield of the desired metabolite. Increasing the amount of biosynthesis genes without the activated upstream precursor synthesis will not affect the yield of the product. When also the precursor pathway is activated it is possible to achieve optimal production levels for the target metabolite.

Two DNA sequences are operably linked when the function of the promoter results in transcription. An operable linkage is a linkage in which a sequence is connected to a regulatory sequence (or sequences) in such a way as to place expression of the sequence under the influence or control of the regulatory sequence.

In this connection the regulatory areas for the cluster genes are naturally occurring within the host organism. The transcriptional control regions are associated with the coding region in nature. These regulatory areas are under influence or control of a transcription factor. For example, the DNA binding domain of transcription factor AN1599 (SEQ ID NO: 74) recognizes CGG triplets or other sequence stretches in varying orientations within the promoter region of the target genes in the biosynthetic cluster area (SEQ ID NO:57) thus activating the transcription of said genes. The CGG triplets or other sequence stretches affecting binding of the transcription factor have not been identified for each gene. However, the promoter areas within the identified cluster are specific for the transcriptional activation by the transcription factor AN1599 (SEQ ID NO: 74). The naturally occurring regulatory regions included within SEQ ID NO:57 can be used with the expressed transcription factor to promote the transcription of the ORFs within the cluster. The regulatory region may contain various elements, for example promoter(s), enhancer(s), repressor(s) or other sequences that regulate transcription or translation. A regulatory region can be exogenous or endogenous in relationship to the host organism. The regulatory regions for the cluster genes described herein (SEQ ID NO:57) are endogenous as well as naturally occurring in relation to coding regions of the genes described.

The promoter used in the overexpression of the transcription factor AN1599 (SEQ ID NO: 74) described herein is endogenous but not naturally occurring. The promoter is operably linked to a coding sequence. The promoter used in the overexpression of the transcription factor can also be heterologous. As used herein, the terms "heterologous promoter" and "heterologous control regions" refer to promoters and other control regions that are not normally associated with a particular nucleic acid in nature. The fungal strain overexpressing AN1599 (SEQ ID NO: 74) described herein also contains natural regulatory region(s) that are associated with the coding region of AN1599 (SEQ ID NO: 74) in nature. The mechanism of upregulation of AN1599 (SEQ ID NO: 74) transcription factor through its natural regulatory regions is not known. Activation of the pimaradiene cluster described herein by activation of AN1599 (SEQ ID NO: 74) through its naturally occurring regulatory region(s) is within the embodiments of this invention.

In a biosynthetic gene cluster the regulatory regions between the enzyme/protein encoding regions comprise promoters, terminators and regions to which various regulatory factors are able to attach. The terms "DNA regulatory sequences", "control elements", and "regulatory elements" used interchangeably herein, refer to transcriptional and translational control sequences, such as promoters, enhancers, polyadenylation signals, terminators, protein degradation signals, and the like, that provide for and/or regulate expression of a coding sequence and/or production of an encoded polypeptide in a host cell. In one embodiment the regulatory regions are those characterized by SEQ ID NO: 57, or a sequence having at least 40%, preferably at least 50%, 60%, 70%, 80% or even 90% degree of identity to said SEQ ID NO: 57 without fractions encoding the synthetic proteins.

It is also embodiment of the invention to use the transcription factor for production of diterpenoids, preferably pimaradiene or its derivates, and especially ent-pimara-8(14),15-diene or its derivatives.

One embodiment is the use of *Aspergillus nidulans* FGSC A4 for producing terpenes using the method as described here and illustrated in the experimental part.

The invention is illustrated by the following non-limiting examples. It should be understood, however, that the embodiments given in the description above and in the examples are for illustrative purposes only, and that various changes and modifications are possible within the scope of the invention.

EXAMPLES

Example 1

Locating the Terpenoid Clusters in Different Filamentous Fungi and the Selection of the Clusters to be Studied Protein sequences of 33 fungi (Arvas et al.) were mapped to their respective genome sequences by BLAST (Altschul et al.) in order to find genomic co-ordinates for each gene. From the gene co-ordinates windows of 16 and 30 consecutive genes along chromosomal sequence were calculated, moving the window along chromosome with increments of 2 and 5 genes, respectively, to cover all 33 genomes with overlapping windows. For each window its protein domain content i.e. InterPro (Mulder et al.) identifier content was determined based on protein domains of individual genes derived from InterPro data of Arvas et al. All windows containing identifiers IPR008949 'Terpenoid synthase' and IPR008930 'Terpenoid cyclase' were found, and the list of these windows was used as source for selecting gene clusters for laboratory manipulations. Alternatively windows containing IPR008930, IPR001128 'Cytochrome P450' and IPR001138 'Fungal transcriptional regulatory protein' were looked for. Data manipulations and visualizations were carried out with custom R (www.r-project.org/) & Perl (www.perl.org/) scripts.

Clusters with a putative diterpenoid synthase gene located close to a fungal $Zn(II)_2Cys_6$-type transcription factor were identified. The clusters chosen for further analysis also included putative Cytochrome P450-genes as well as enzymes predicted to participate in terpenoid precursor synthesis or modification of the terpenoid product. The three selected clusters from *Aspergillus nidulans* did not reside in the immediate vicinity of another secondary metabolite synthase gene, such as polyketide synthase, thus avoiding the study of hybrid metabolite clusters. The transcription factors from the three selected clusters were AN1599 (SEQ ID NO: 1), AN3250 (SEQ ID NO: 2) and AN6814 (SEQ ID NO: 3). Similar clusters were also found in *Neosartorya fischeri, Microsporum canis, Trichoderma reesei, Neurospora crassa, Aspergillus clavus, Aspergillus fumigatus, Aspergillus niger, Aspergillus oryzae, Aspergillus terreus, Botrytis cinerea, Magnaporthe grisea, Fusarium graminearum*, and *Fusarium oxysporum*, and the terpenoid clusters were mapped in *Ashbya gossypii, Candida albicans, Candida glabrata, Candida guilliermondii, Candida lusitaniae, Chaetomium globosum, Debaryomyces hansenii, Kluyveromyces lactis, Pichia pastoris, Pichia stipitis, Saccharomyces castellii, Saccharomyces cerevisiae, Saccharomyces kluyveri, Yarrowia lipolytica, Coprinus cinereus, Cryptococcus neoformans, Phanerochaete chrysosporium, Coccidioides immitis, Schizosaccharomyces pombe, Sclerotinia sclerotiorum, Stagonospora nodorum, Ustilago maydis*, and *Rhizopus oryzae*.

FIG. 1 shows chromosomal areas of predicted terpene synthase clusters. Pictures are adapted from *Aspergillus* Genome Database (Arnaud et al.) using Genome Browser tool.

Example 2

Cloning of the Selected Transcription Factors in Fungal Expression Constructs

Genomic DNA was extracted by homogenizing 300-500 mg of FGSC A4 mycelia grown over night in YES-medium. 500 µL of glass beads (Acid-washed glass beads, cat #G8772, Sigma), 500 µL 1×TE-buffer, pH 7.5 and 500 µL phenol-chloroform-isoamyl alcohol was added to 2 mL vial with mycelia and homogenized in Fast Prep-homogenizer at speed 6 for 25 seconds. Aqueous layer was separated with 5 minute centrifugation at 15 000 rpm at 4° C., and 650 µL of phenol-chloroform-isoamyl alcohol was added. DNA purification from the aqueous phase was continued according to phenol extraction and ethanol precipitation of DNA-protocol (Current Protocols in Molecular Biology). Concentration of the DNA was measured with Nanodrop (Thermo Scientific).

Open reading frames (ORFs) of AN1599 (SEQ ID NO: 1), AN3250 (SEQ ID NO: 2) and AN6814 (SEQ ID NO: 3) were amplified with PCR using 43 ng of genomic DNA extracted from *Aspergillus nidulans* FGSC A4 as template. Primer concentration was 300 nM for both sense and anti-sense primers in 50 µL total volume. PCR was done according manufacturer's protocol with Expand High Fidelity PCR System (Cat #11 732 650 001, Roche). Primers used in the PCR for *Aspergillus nidulans* AN1599 were SEQ ID NO: 4 and SEQ ID NO: 5, primers used in the PCR for *Aspergillus nidulans* AN3250 were SEQ ID NO: 6 and SEQ ID NO: 7, and primers used in the PCR of *Aspergillus nidulans* AN6814 were SEQ ID NO: 8 and SEQ ID NO: 9. Oligos were synthesized at 0.025 scale and purified by desalting at Sigma-Aldrich.

Figure 2:
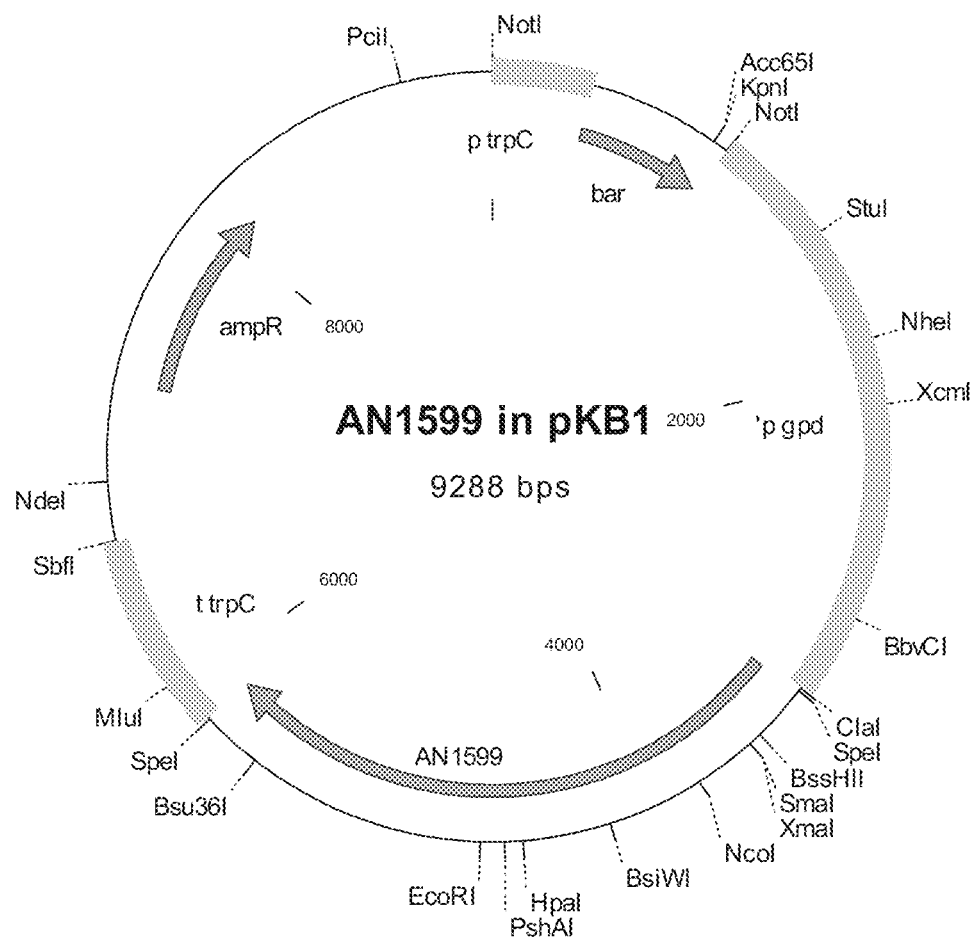
FIG. 2. is a schematic representation of a fungal expression vector for AN1599 (SEQ ID NO: 10)
Figure 3:
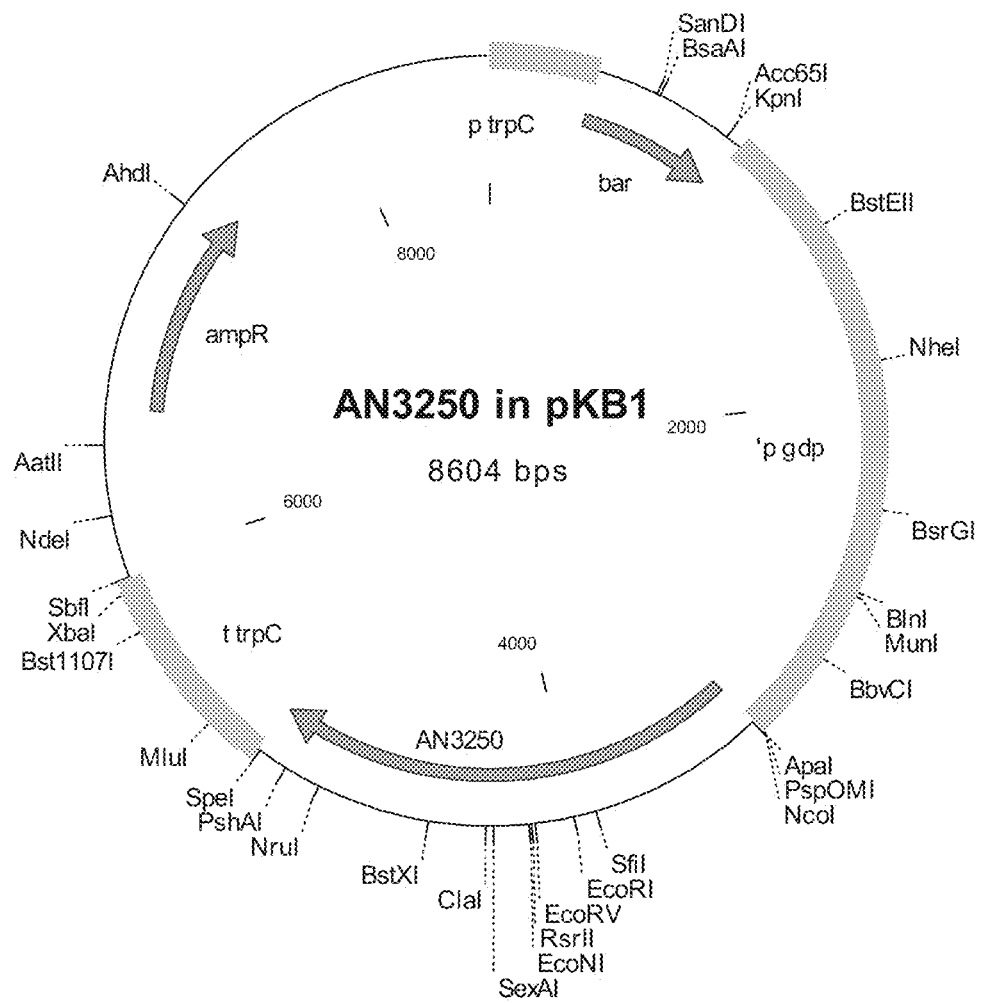
FIG. 3. is a schematic representation of a fungal expression vector for AN3250 (SEQ ID NO: 11)
Figure 4:
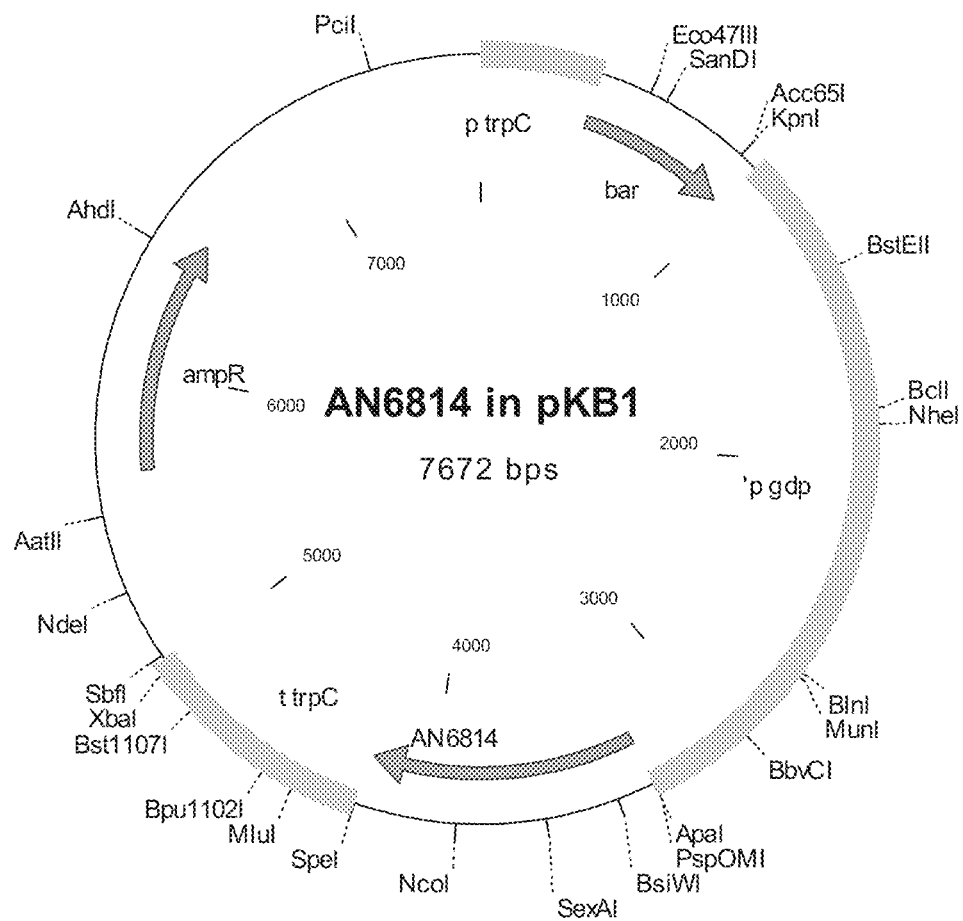
FIG. 4. is a schematic representation of a fungal expression vector for AN6814 (SEQ ID NO: 12)

Amplification for AN1599 and AN6814 was done in thermal cycler with following parameters: 1 cycle at 95° C. for 5 minutes, 30 cycles at 94° C. for 15 seconds, 68° C. for 30 second, and 72° C. for 2 minutes, 1 cycle at 72° C. for 7 minutes, and cool down at +4° C. Amplification of AN3250 was done with following parameters: 1 cycle at 95° C. for 5 minutes, 30 cycles at 94° C. for 15 seconds, 63° C. for 30 second, and 72° C. for 1 minute 20 seconds, 1 cycle at 72° C. for 7 minutes, and cool down at +4° C. Fragments were checked on agarose gel and cloned into pCR 2.1 TOPO-vector (Cat #K4510-20, TOPO TA Cloning® Kit (with pCR 2.1 TOPO-vector), Invitrogen) according to manufacturer's protocol. Full-length genomic AN1599 was digested from pCR2.1 TOPO-vector with SpeI (cat #R0133S, New England Biolabs, Inc.), and AN3250 and AN6814 were digested with both SpeI and ApaI (cat #R0114S, New England Biolabs, Inc.). All fragments were sub-cloned into pKB1-vector.

pKB1-vector was constructed by adding PCR-amplified glufosinate ammonium resistance gene, bar, into NotI-site of modified pAN52-1NotI-vector (Kuorelahti et al.). bar-fragment had been PCR amplified from pTJK1 (Jones et al.) with added NotI-sites on both ends of the fragment. The fragment contains *Aspergillus nidulans* trpC promoter upstream of bar-resistance gene. AN1599-fragment was cloned into the SpeI-site of pKB1 (SEQ ID NO: 10), and AN3250 and AN6814 were cloned into the SpeI and ApaI-sites of pKB1-vector (SEQ ID NO: 11 and SEQ ID NO: 12 respectively). All constructs were sequence-verified before transformations. Schematic representations of the expression vectors for AN1599, AN3250 and AN6814 are shown as FIGS. 2, 3 and 4, respectively.

Example 3

Generating the Fungal Strains Overexpressing the Transcription Factor

Conidia of *Aspergillus nidulans* strain FGSC A4 Glasgow wild type (veA+) (Fungal Genetics Stock Center, School of Biological Sciences, University of Missouri, Kansas City, 5007 Rockhill Road, Kansas City, Mo. 64110, USA) were inoculated in YES-medium supplemented with gelatine [20 g Bacto™ Yeast Extract (Cat #212750, Becton, Dickinson and Company), 40 g sucrose (Calbiochem Cat #573113) and 30 g Difco™ Gelatin (Cat #214340, Becton, Dickinson and Company) per liter of $dH_2O$], and grown at +24° C. in shaking flasks over night with 250 rpm. Cultures were transferred to +30° C. shaker the next morning and the grown with 250 rpm for 2 hours. Protoplasts were prepared from *Aspergillus nidulans* FGSC A4 mycelium, that was filtered through sterile Miracloth, and rinsed with +37° C. $dH_2O$, and room temperature citrate buffer [0.8 M KCl, 0.05 M Na-citrate, pH 5.8]. Filtrated mycelium was resuspended in 100 mL of room temperature citrate buffer supplemented with 1 mM dithiotreitol and 50 mL of 3% enzyme-solution[1.5 g of Hydrolyzing enzymes from *Trichoderma harzianum*, cat #L1412, Sigma in 50 mL of citrate buffer] was added. Protoplasting was done at +30° C. for 2.5 hours shaking at 100 rpm, and protoplast formation was monitored under microscope at 50 minute-, and 1.5 hour-time-points during the enzyme treatment. Suspension was cooled on ice for 10 minutes and then filtered through sterile Miracloth to a sterile flask, and the protoplast suspension was transferred to 50 mL conical tubes. Protoplasts were centrifuged at 1500×g for 5 minutes at +4° C. in a tabletop centrifuge, and supernatant was discarded. Pelleted protoplasts were washed with cold GTC-buffer [1 M glucose, 50 mM $CaCl_2$, 10 mM Tris-HCl, pH 5.8], centrifuged at 1500×g for 5 minutes at +4° C. in a tabletop centrifuge, and resuspended in 600 µL of GTC. 600 µL of 40% glycerol was added and protoplasts were stored at −80° C. until transformation.

Selective plates for the transformation were prepared with modified minimal medium (MM) (Kaminskyj). 1 liter of MM was supplemented with 1 mL of Triton x-100 (Cat #93418, Fluka Analytical), 18 g of Difco™ Agar Noble (Cat #214230, Becton, Dickinson and Company), and 200 µg/mL of glufosinate ammonium (Cat #45520, Glufosinate-ammonium, PESTANAL®, Sigma-Aldrich). Glufosinate ammonium was added to cooled solution after autoclaving. Top agar used in the transformations was prepared without Triton x-100 in minimal medium supplemented with 2% agar and 200 µg/mL of glufosinate ammonium. Selective MM-plates were also used for the subsequent selection of the transformants.

Protoplast suspension was thawed on ice and 400 µL of the suspension was transferred to a 15 mL tube. Glycerol was washed out with 2 mL of cold GTC, and protoplasts were suspended in 180 µL of cold GTC. 20 µg of the expression plasmids were linearized with PciI (cat #R0655S, New England Biolabs Inc.) at +37° C. for 1.5 hours. Linearized DNA was precipitated at −80° C. for 15 minutes after adding dH$_2$O up to 100 µL, 10 µL of 3 M NaAc (sodium acetate), pH 4.8, and 275 µL of 94% EtOH. Precipitated DNA was collected by 5 minute centrifugation at 15 000 rpm at +4° C., washed with 70% EtOH and re-suspended in 20 µL of GTC. DNA was added to protoplasts and mixed by tapping the tube. 50 µL of PEG-solution[25% PEG6000, 50 mM CaCl$_2$, 10 mM Tris-HCl, pH 7.5] was mixed with protoplast and DNA and the tubes were incubated on ice for 20 minutes. 2 mL of PEG-solution was added, and the transformation solution was transferred to 15 mL vial. The vial was incubated at room temperature for 5 minutes, 4 mL of RT GTC was added, and tubes mixed by inverting. 6 mL of +55° C. top agar was supplemented with 1.2 mg of glufosinate ammonium and added to 6 mL of transformation mix. Vials were mixed by inverting and the top agar with transformed protoplasts was poured on selective minimal medium (MM)-plates.

Plates were incubated at +30° C. until transformed colonies were visible. Colonies from transformation plates were picked on the selective MM-plates, diluted to single-nucleated colonies and the insertion of the expression constructs was verified with PCR from the genomic DNA of the selected clones. Sense primer used for the checking of the expression cassettes was SEQ ID NO: 13, and the gene-specific antisense primer for *Aspergillus nidulans* AN1599 was SEQ ID NO: 14, for AN3250 SEQ ID NO: 15, and for AN6814 SEQ ID NO: 16. PCR-confirmed positive clones were grown on potato dextrose plates [37 g of Difco™ Potato Dextrose Agar per liter of dH$_2$O] until the spore collection. Spores of the transformant fungi were collected into 0.8% NaCl, 0.025% Tween-20 and 20% glycerol, and stored at −80° C.

Example 4

Real-Time PCR Analysis to Check the Expression of the Integrated Transcriptional Activators and Two Target Genes from Each Cluster Transformant spores collected from potato dextrose plates were inoculated in YES-media and grown to confluency in shaking flasks at +30° C. 250 rpm. Mycelium was harvested to sterile Miracloth (#475855, Calbiochem) by vacuum filtration, rinsed with +37° C. dH$_2$O, and three 100 µL batches of each culture were scooped into 1.5 mL microfuge tubes, flash frozen in liquid nitrogen and stored at −80° C. until RNA extraction.

Three RNA extractions were done from each transformant culture to have statistical variation within the sample preparation. RNA was extracted from 100 µL of frozen mycelium, which was homogenized in 450 µL RLT-buffer (RNeasy® Plant Mini Kit, Cat #74904, Qiagen) supplemented with b-mercaptoethanol using pestle and motor mixer (VWR™ Disposable Pestle, Cat #47747-358, Pellet Mixer, Cat #47747-370). Samples were further homogenized with QiaShredder column (RNeasy® Plant Mini Kit, Cat #74904, Qiagen), and the RNA extraction protocol was continued following RNeasy® Plant mini Kit-protocol. Genomic DNA was removed from the samples using RNase-Free DNase Set (Cat #79254, Qiagen) following the DNase Digestion of RNA before RNA Cleanup-protocol. RNA was quantified spectrophotometrically using Nanodrop (Thermo Scientific), and the quality of the RNA was checked with agarose gel electrophoresis.

cDNA synthesis was done following the protocol of Transcriptor First Strand cDNA Synthesis Kit (Cat #04 897 030 001, Roche) with 5 µg of total RNA as template. cDNA was stored at −20° C. until analysis. Each sample was tested in three replicates to see the variation in quantitative PCR reaction set-up. Real-time quantitative PCR analysis reactions were set up using the protocol for LightCycler® 480 SYBR Green I Master mix (Cat #04887352001, Roche), and analyzed in LightCycler® 480 Instrument (Roche). The 15 µL reactions were prepared in LightCycler® 480 white Multiwell Plate 96 (Cat #04729692001, Roche) using 0.5 µM concentration of the primers.

Each transformant strain was tested with qPCR to see, if the integrated transcriptional activators have higher expression levels, than the FGSC A4 wild type strain. In addition to checking the success of the transformant generation, the activation of the clustered genes was checked with the primers specific to the genes putatively encoding a terpene synthase, and one modifying enzyme from each cluster.

PCR parameters for AN1599, AN1594, AN1598, AN3250, AN3252 and AN3253 were: Pre-incubation: 5 minutes at 95° C. with a ramp rate of 4.4° C./s; Amplification for 50 cycles: 95° C. for 10 seconds with a ramp rate of 4.4° C./s, 60° C. for 10 seconds with a ramp rate of 2.2° C./s, 72° C. for 10 seconds with a ramp rate of 4.4° C./s; Melting curve: 95° C. for 5 seconds with a ramp rate of 4.4° C./s, 65° C. for 1 minute with a ramp rate of 4.4° C./s and then continuously to 97° C.; Cooling at 40° C. for 10 seconds with a ramp rate of 1.5° C./s. The primers used in quantitative PCR analysis were SEQ ID NO: 17 and SEQ ID NO: 18 for *Aspergillus nidulans* β-actin, SEQ ID NO: 19 and SEQ ID NO: 20 for AN1599, SEQ ID NO: 21 and SEQ ID NO: 22 for AN1594, SEQ ID NO: 23 and SEQ ID NO: 24 for AN1598, SEQ ID NO: 25 and SEQ ID NO: 26 for AN3250, SEQ ID NO: 27 and SEQ ID NO: 28 for AN3252, SEQ ID NO: 29 and SEQ ID NO: 30 for AN3253.

PCR parameters for AN6810, AN6814 and AN6807 were: Pre-incubation: 5 minutes at 95° C. with a ramp rate of 4.4° C./s; Amplification for 50 cycles: 95° C. for 10 seconds with a ramp rate of 4.4° C./s, 57° C. for 10 seconds with a ramp rate of 2.2° C./s, 72° C. for 10 seconds with a ramp rate of 4.4° C./s; Melting curve: 95° C. for 5 seconds with a ramp rate of 4.4° C./s, 65° C. for 1 minute with a ramp rate of 4.4° C./s and then continuously to 97° C.; Cooling at 40° C. for 10 seconds with a ramp rate of 1.5° C./s. Primers used in quantitative PCR analysis were SEQ ID NO: 31 and SEQ ID NO: 32 for AN6814, SEQ ID NO: 33 and SEQ ID NO: 34 for AN6810, SEQ ID NO: 35 and SEQ ID NO: 36 for AN6807. The expression levels were normalized to the levels of β-actin expression in each sample.

Figure 5:
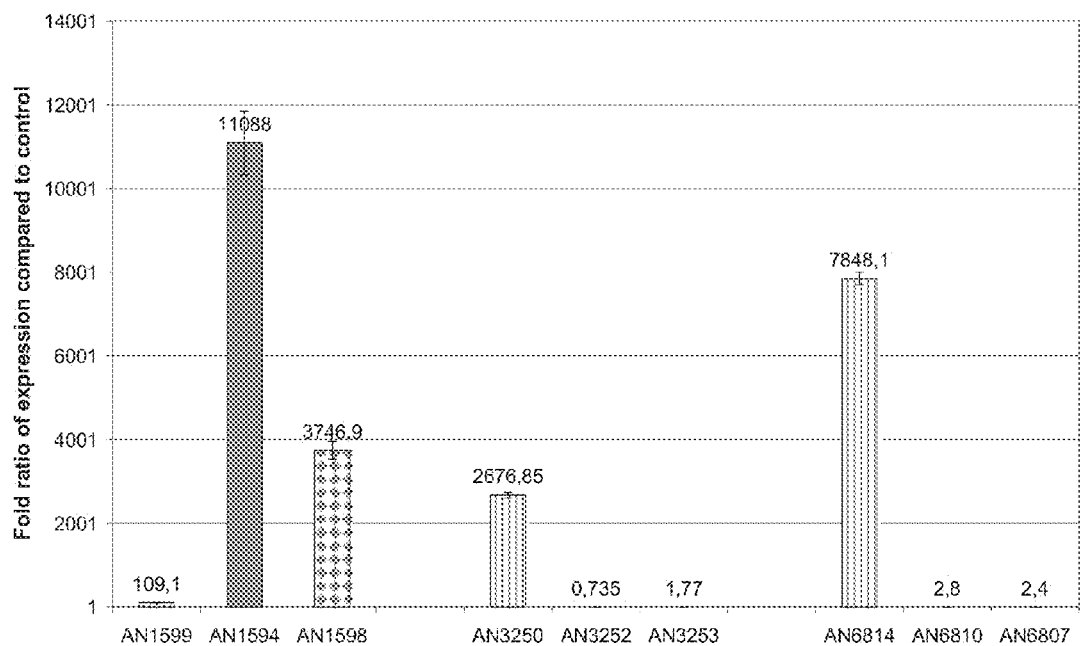
FIG. 5 Shows an elevated expression level for the overexpressed transcriptional activators AN1599, AN3250, and AN6814 (bars with vertical lines). Terpene synthase gene AN1594, AN3252, and AN6814 (solid bars) and a gene coding for a modifying enzyme from each cluster, AN1598, AN3253, AN6807 (bars with diamonds), are expressed in significantly higher levels only in cluster 1. Value shown on top of each bar represents the fold ratio difference of the *Aspergillus nidulans* transformant-strain compared to *Aspergillus nidulans* FGSC A4 wild type-strain. The expression level of the wild type strain is considered to be 1 for each gene. Error bars represent the standard deviation in the expression fold-ratios for three replicates of three individual samples from each strain.

Efficiencies for each primer set were calculated from serial dilutions of the template cDNA, and the expression fold ratios were quantified using pfaffl-equation (Pfaffl). The results are shown is FIG. 5.

Albeit the high expression of *Aspergillus nidulans* transcription factors AN3250 (2676.85-fold higher than the *Aspergillus nidulans* FGSC A4 control) and AN6814 (7848.1-fold higher than the control) in their corresponding transformant strains, the expression levels of the predicted target genes were not significantly elevated. In the *Aspergillus nidulans* AN1599-transformant strain, the approximately 100-fold expression of the transcription factor was sufficient to significantly activate the two predicted target genes AN1594 (11088-fold higher expression than in the control and AN1598 (3746.9-fold higher than in the *Aspergillus nidulans* FGSC A4 control). *Aspergillus nidulans* AN1599-transformant strain was chosen for the subsequent experiments.

Example 5

Identifying the Cluster Limits with Quantitative Real-Time PCR Analysis (qPCR)

Expression of 13 genes in the genomic area of AN1599 was quantified with qPCR in *Aspergillus nidulans* AN1599-transformant and FGSC A4 to see which of the genes respond to the over-expression of the transcription factor. Total RNA extraction and cDNA synthesis-protocol, and the primers for AN1594, AN1598, and AN1599 were the same as in Example 5. Expression of AN1588 was checked with primers SEQ ID NO: 37 and SEQ ID NO: 38, AN1589 with primers SEQ ID NO: 39 and SEQ ID NO: 40, AN1590 with primers SEQ ID NO: 41 and SEQ ID NO: 42, AN1591 with primers SEQ ID NO: 43 and SEQ ID NO: 44, AN1592 with primers SEQ ID NO: 45 and SEQ ID NO: 46, AN1593 with primers SEQ ID NO: 47 and SEQ ID NO: 48, AN1595 with primers SEQ ID NO: 49 and SEQ ID NO: 50, AN1596 with primers SEQ ID NO: 51 and SEQ ID NO: 52, AN1597 with primers SEQ ID NO: 53 and SEQ ID NO: 54, AN1600 with primers SEQ ID NO: 55 and SEQ ID NO: 56.

The PCR parameters were: Pre-incubation: 5 minutes at 95° C. with a ramp rate of 4.4° C./s; Amplification for 50 cycles: 95° C. for 10 seconds with a ramp rate of 4.4° C./s, 55° C. for 10 seconds with a ramp rate of 2.2° C./s, 72° C. for 10 seconds with a ramp rate of 4.4° C./s; Melting curve: 95° C. for 5 seconds with a ramp rate of 4.4° C./s, 65° C. for 1 minute with a ramp rate of 4.4° C./s and then continuously to 97° C.; Cooling at 40° C. for 10 seconds with a ramp rate of 1.5° C./s.

All expression values were normalized with β-actin expression and the fold-ratios of the *Aspergillus nidulans* AN1599-transformant were compared to those of the *Aspergillus nidulans* FGSC A4 wild type fungus. Primer efficiencies and the expression fold ratios were calculated as in Example 5. The results are shown is FIG. 6.

Genes belonging to the putative diterpene secondary metabolite cluster were identified with quantitative real-time PCR and DNA array expression analysis. The genes in the cluster are AN1592, AN1593, AN1594, AN1595, AN1596, AN1597, AN1598, AN1599, and putatively AN1591.

Further, homologies of the gene products within putative terpene cluster were estimated using NCBI BLASTp-program.

Table 1. shows the closest match obtained using deduced amino acid sequences in BLASTp (protein-protein BLAST) search with non-redundant protein sequences (nr) as database.

| Protein | Closest match | Identities (%) | Positives (%) | Coverage (%) |
|---|---|---|---|---|
| SEQ ID NO: 59 AN1591 | *Aspergillus niger* An07g04480 | 46 | 62 | 84 |
| SEQ ID NO: 61 AN1592 | GGPP-synthase *Neosartorya fisheri* NFIA_009870 | 85 | 91 | 100 |
| SEQ ID NO: 63 AN1593 | HMG-CoA reductase *Neosartorya fisheri* NFIA_009850 | 89 | 95 | 100 |

-continued

| Protein | Closest match | Identities (%) | Positives (%) | Coverage (%) |
|---|---|---|---|---|
| SEQ ID NO: 65 AN1594 | Hypothetical protein *Neosartorya fisheri* NFIA_009790 | 86 | 92 | 97 |
| SEQ ID NO: 67 AN1595 | Elongation factor 1 gamma *Neosartorya fisheri* NFIA_009800 | 89 | 95 | 92 |
| SEQ ID NO: 69 AN1596 | Conserved hypothetical protein *Aspergillus terreus* ATEG_00056 | 89 | 94 | 100 |
| SEQ ID NO: 71 AN1597 | *Neosartorya fisheri* NFIA_009820 | 89 | 95 | 91 |
| SEQ ID NO: 73 AN1598 | Putative Cytochrome P450 monooxygenase *Neosartorya fisheri* NFIA_009830 | 92 | 95 | 99 |
| SEQ ID NO: 74 AN1599 | C6 zinc finger domain protein *Neosartorya fisheri* NFIA_009840 | 79 | 84 | 99 |

Example 6

Identifying the Product of the Activated Secondary Metabolite Cluster in AN1599-Transformant with SPME-GC/MS The results of the expression analysis showed highly elevated transcription levels for seven of the predicted secondary metabolite cluster genes. Product was expected to be a diterpenoid compound. Diterpenoids are usually semi-volatile or volatile components, which can be efficiently separated and identified with Gas Chromatography. The method chosen for the analysis of the product in the activated strain was Solid Phase Microextraction-Gas Chromatography/Mass Spectrometry analysis (SPME-GC/MS), which detects semi-volatile and volatile components with minimal handling of the samples.

Conidia of AN1599-transformant and FGSC A4 were inoculated in 2 mL of YES-media supplemented with 3% gelatine and grown at +30° C. in 15 mL culture vials shaking 250 rpm for 44 hours. Different amounts of conidia were seeded to get the similar confluency of both AN1599-transformant and FGSC A4 wild-type control-samples at the end of culturing. The cultures with matching confluencies were subjected to SPME-GC/MS.

Figure 7:
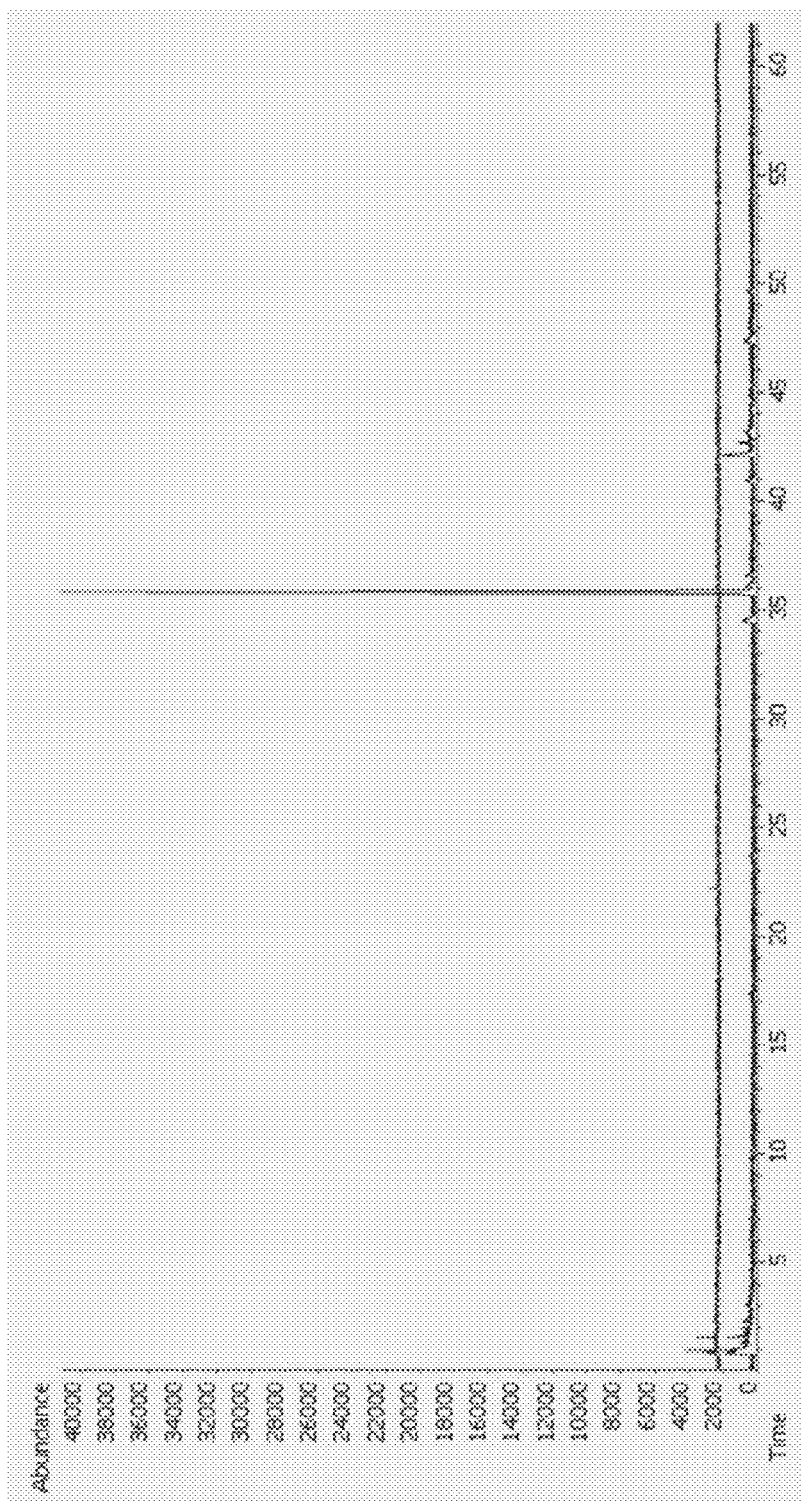
FIG. 7 is an SPME-Gas Chromatogram for FGSC A4 wild-type and AN1599-transformant fungus. Upper graph with the baseline of about 2000 shows the spectrum for FGSC A4 strain with no significant peaks. The lower graph of the AN1599 strain shows the major peak at about 36 minutes retention time.
Figure 8:
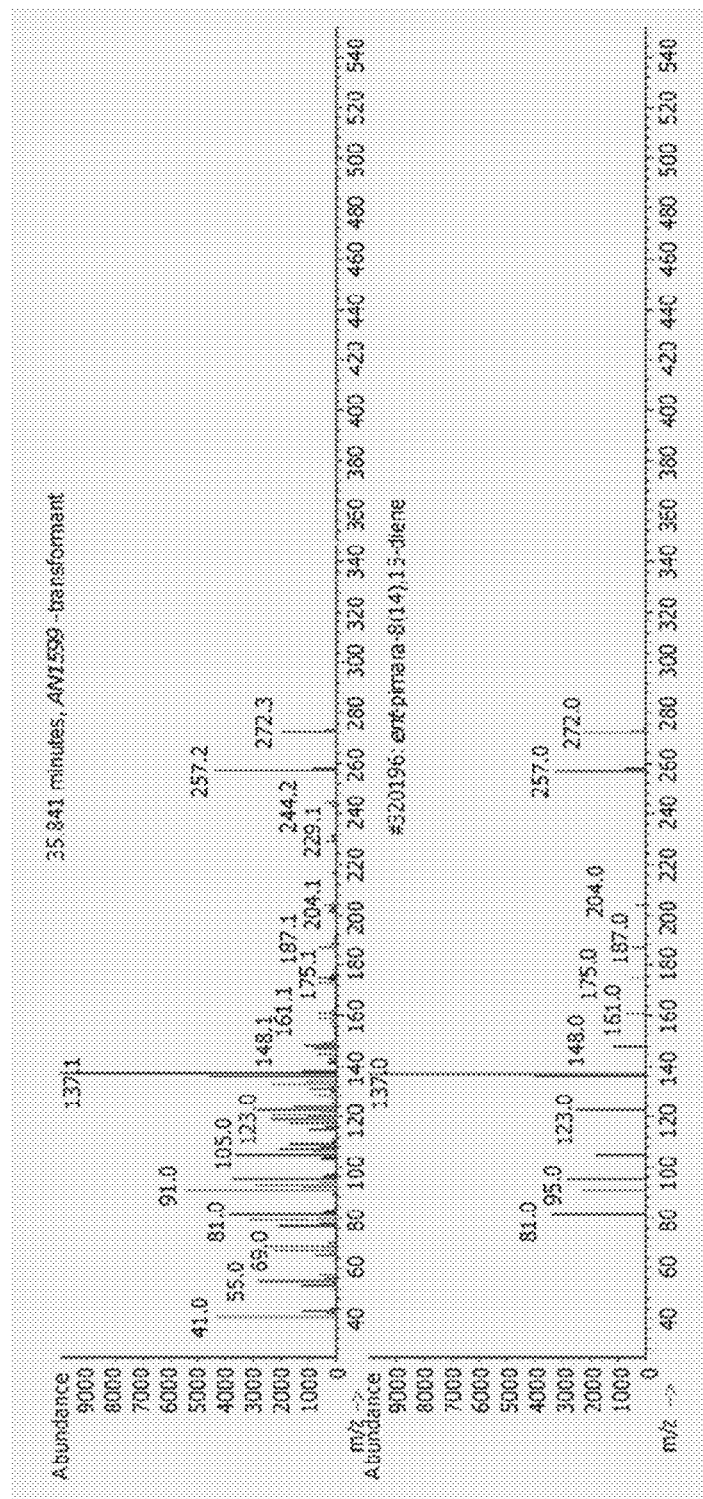
FIG. 8. Mass spectrum of the major peak separated in GC analysis for AN1599-transformant matches the PAL spectral library product ent-pimara-8(14),15-diene with 96% similarity.

Samples were transferred to air-tight SPME-vials. The extraction was done with 100 μm PDMS fibre at +80° C. for 1 hour. After extraction, the analytes were desorbed during 5 min at +250° C. in the injector of the gas chromatography. Analytes were separated on Ultra 2 capillary column of 25 m×0.2 mm with a phase thickness 0.33 μm. The temperature program was: +40° C., holding 1 min, 9° C./min increased up to +130° C., followed by 2° C./min increased up to +230° C., holding 1 min. MS was operated in electron-impact mode at 70 eV, in the scan range m/z 40-550. Compounds were identified by use of the PAL spectral library. The result is shown in FIG. 7 and FIG. 8.

The SPME-gas chromatogram showed a major peak at 35,841 minute retention time for AN1599-transformant fungus. This peak was not present in the FGSC A4 control. This peak was further analyzed by its mass spectrum to be ent-pimara-8(14),15-diene with 96% quality. The analysis verified that AN1599 activates an ent-pimara-8(14),15-diene diterpene cluster in the transformant fungus.

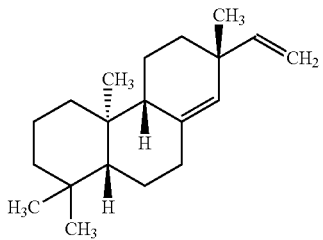

Chemical structure of ent-pimara-8(14),15-diene. Molecular formula $C_{20}H_{32}$, molecular mass 272,46808 g/mol, IUPAC names: (4a5,4b5,7S,10aS)-7-ethenyl-1,1,4a,7-tetramethyl-3,4,4b,5,6,9,10,10a-octahydro-2H-phenanthrene and 5β,9β,10α,13α-pimara-8(14),15-diene.

Example 7

Recovery of the Terpene Product and Further Identification of the Product with GC/MS Extraction Both *Aspergillus nidulans* AN1599-transformant and FGSC A4 strains were grown to confluency in 200 mL YES-media supplemented with 3% gelatin. Mycelia was filtered through sterile Miracloth, wrapped in aluminium foil, and frozen in liquid nitrogen. Mycelial pellets were stored at −80° C. until homogenized with mortar and pestle in liquid nitrogen. The powdered mycelia was weighed and 2 g of mycelia was extracted with 20 mL of hexane:ethyl acetate (1:1) in 100 mL glass Erlenmeyer flasks in ultrasonic water bath for 1 hour in room temperature. Solvent phase of hexane:ethyl acetate-extract was separated by centrifuging the samples at 1500 rpm for 5 minutes at +4° C.

GC-MS Assay of Diterpenes

Figure 9:
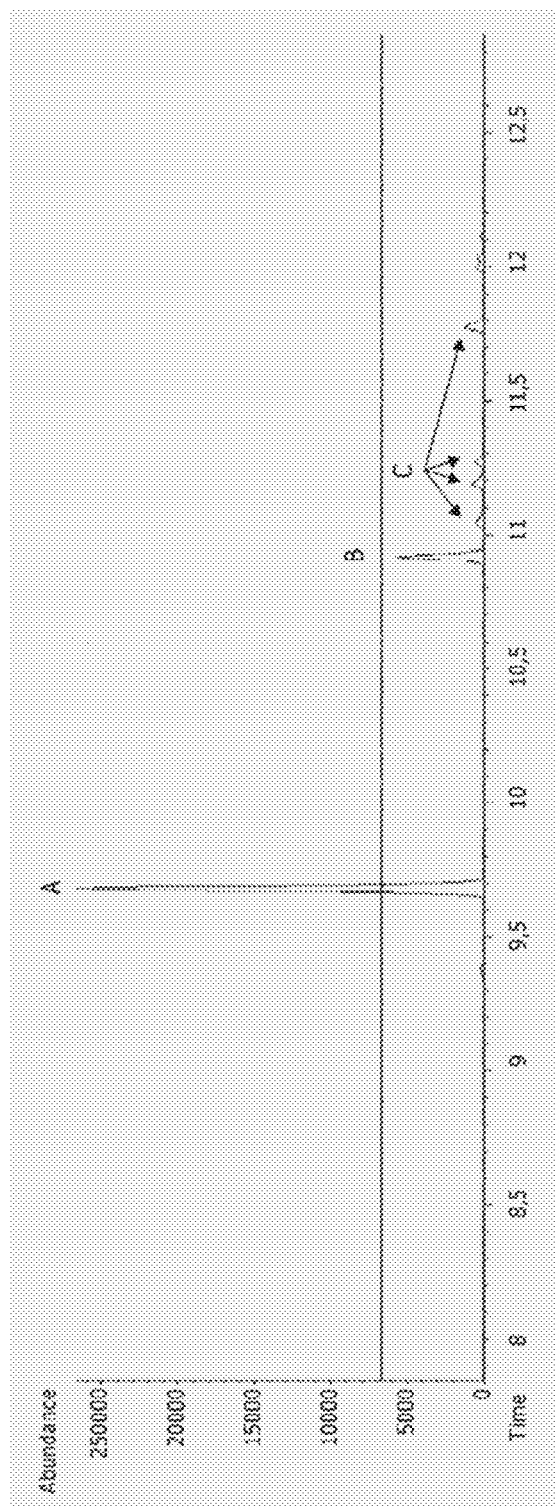
FIG. 9. shows GC/MS data of the extracts from FGSC A4 and AN1599 transformant strains.

1 µl volume of the extract was injected in a split mode (split ratio 10:1) into Agilent 6890 gas chromatography connected to Mass Selective Detector. Analytes were separated on HP-1 capillary column of dimensions 25 m×0.32 mm×0.17 µm. The temperature program began at 100° C., holding 0.5 min and then increased by rate of 10° C./min to final temperature of 320° C., holding 25 min. The flow rate of carrier gas (He) was 1.3 mL/min (constant flow mode). The temperatures of the injector and MS source were 260° C. and 230° C., respectively. MS was operated in electron-impact mode at 70 eV with full scan mode m/z 40-550. The result is shown as FIG. 9. The identification was made with PAL spectral library.

Example 8

DNA Array Expression Analysis

Both AN1599-transformant and FGSC A4 strains were subjected to DNA array expression analysis to verify the results of the quantitative real-time PCR and to get a broader understanding of the transcriptional changes in the AN1599-transformant fungus. DNA array expression analysis enables the screening of the transcriptional levels of all known genes of *Aspergillus nidulans*.

Chip Design

Sequence source for the 10597 transcripts in the DNA array design was: ftp.ensemblgenomes.org/pub/fungi/release4/fasta/*aspergillus_nidulans*/cdna/*Aspergillus_nidulans*.CADRE2.4.cdna.all.fa.gz. Sequence source for the whole genome was: ftp.ensemblgenomes.org/pub/fungi/release-4/embl/*aspergillus_nidulans*/*Aspergillus_nidulans*.0.dat.gz DNA array chip was custom designed and the chip manufacturing was carried out by Nimblegen using Custom Eukaryotic 12×135K Array format. Expression portion was designed by selecting 6 probes per transcript for 10546 out of 10597 transcripts (51 not found, 18 less than 6 probes per transcript, 114 duplicate probes/exemplars).

Sample Preparation for DNA Array Gene Expression Analysis.

Three 50 mL cultures were inoculated for both FGSC A4 and AN1599-transformant strain. The cultures were grown over night at +37° C. shaking incubator at 250 rpm in YES-medium supplemented with gelatine. Each culture flask was monitored for the pH changes during growth and the samples for the DNA array were taken from cultures at pH-values 5.76 to 5.94. This pH-range corresponds to the early exponential growth phase of *Aspergillus nidulans* (data not shown). FGSC A4 reached the exponential growth phase in 21.5 hours and the AN1599-transformant strain in 26 hours. Mycelia were filtered through sterile Miracloth and three 100 µL samples of wet mycelia were scooped to microfuge tubes from two separate culture flasks of each strain giving a total of six replicates for each strain, 12 samples altogether. Mycelia were frozen in liquid nitrogen and the total RNA was purified as in example 5. RNA quality was assessed with the standard protocol of Agilent 2100 Bioanalyzer by Agilent Technologies. 30-50 µg of total RNA was sent to RocheNimblegen for cDNA synthesis, probe hybridization, scan and preliminary analysis.

Example 9

Analysis of the DNA Array

Figure 6:
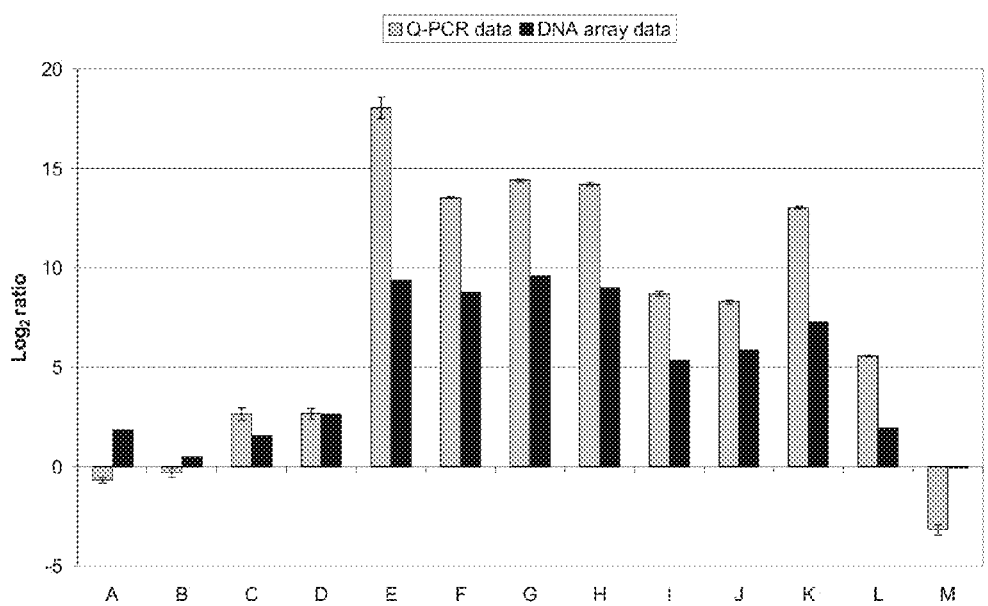
FIG. 6 shows expression levels of 13 genes in the AN1599 genomic area. Putative terpene cluster genes show significantly elevated expression levels in both qPCR and DNA array analysis. Expression of eight target genes is significantly elevated in the *Aspergillus nidulans* FGSC A4 expressing the $Zn(II)_2Cys_6$-type transcription factor, AN1599 (SEQ ID NO: 74), under strong constitutive promoter. The expression level of the wild type strain is considered to be 1 for each gene. Error bars for qPCR data represent SEM, Standard Error of the Mean, for three replicates of three individual samples from each strain. The significance level for each gene expression fold ratio of DNA array data was 99% with p-values ≤0.01 calculated with student's T-test using ArrayStar software.

DNA array data was analyzed with ArrayStar program from DNASTAR. Expression fold changes were calculated using 99% significance level measured with Student's T-test. P-values for all the fold change differences were ≤0.01. The expression profile of the terpene biosynthetic gene cluster is represented in FIG. 6 with quantitative real-time PCR results. The results of the DNA array were consistent with the qPCR data for the cluster genes. DNA array expression analysis revealed a total of 66 genes with more than 5-fold upregulation in the AN1599-transformant compared to FGSC A4 control strain. These 66 genes included the seven terpene biosynthetic cluster genes (AN1592, AN1593, AN1594, AN1595, AN1596, AN1597 and AN1598). 75 genes were more than 5-fold downregulated in the transformant strain. Interestingly, many of the highly downregulated genes were identified as other secondary metabolite biosynthesis genes with BLASTp and pfam-homology searches, such as genes coding for proteins of polyketide and nonribosomal peptide biosynthetic pathways. None of the other terpene clusters showed any significant change in the expression levels in the transformant compared to the control.

This proves the hypothesis of the specific upregulation of the target diterpene cluster genes, and shows that other possibly competing secondary biosynthetic pathways stay either silent or are further downregulated when the biosynthetic pathway for ent-pimara-8(14),15-diene is activated. In addition, expression of many transporter and transferase-genes were upregulated in the AN1599-transformant. This can be beneficial for the production of the diterpene compound and for the wellbeing of the fungus itself by protecting it from the accumulation of harmful side products. The holistic transcriptional regulation in the AN1599-transformant due to the cluster activation supports the specific production of ent-pimara-8(14),15-diene.

Figure 10:
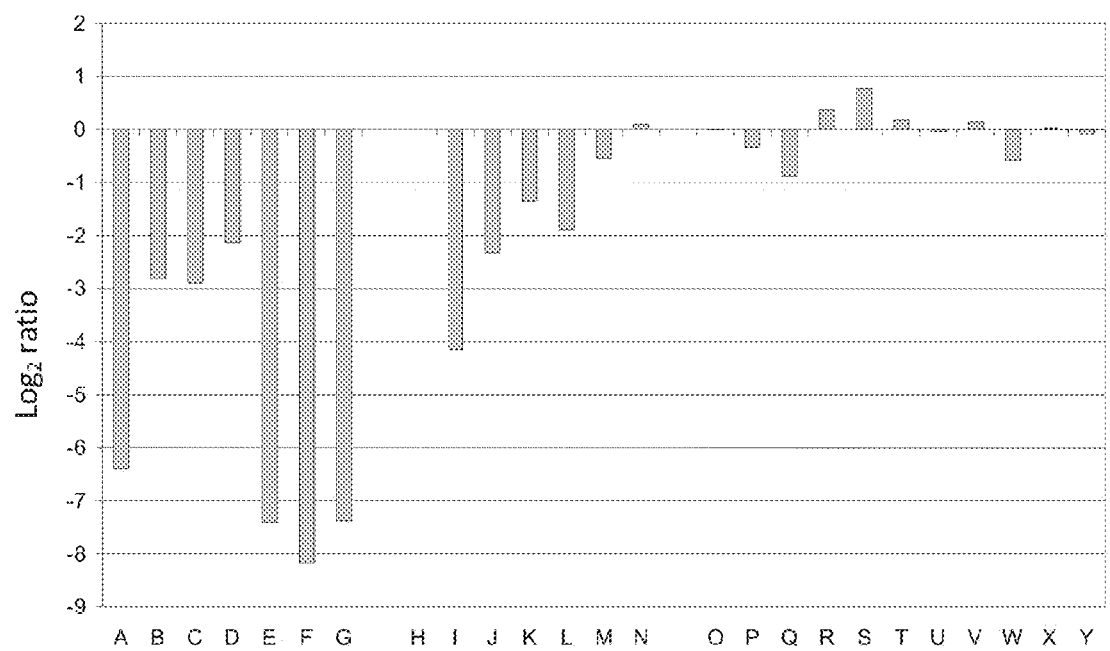
FIG. 10. The changes in the gene expression levels of other secondary metabolite clusters can be seen with the DNA array analysis.

FIG. 10 shows the holistic effect of the transcriptional regulation in the AN1599-transformant, where other secondary metabolite clusters are either downregulated or stay at the level of the control strain.

Example 10

Sequence Data for the Whole Genomic Area of the Terpene Biosynthetic Gene Cluster The genomic sequence for the identified terpene biosynthetic gene cluster, SEQ ID NO: 57, has been adapted from NCBI webpage TPA_reasm: *Aspergillus nidulans* FGSC A4 chromosome VII, sequence coordinates 1222669 to 1249423. This sequence covers 1499 base long promoter region for the first putative cluster gene, AN1591, and a 1499 base long terminator region for the last putative cluster gene, AN1599. The whole genomic sequence is 26775 bases long and it covers genes AN1591 (SEQ ID NO: 58), AN1592 (SEQ ID NO: 59), AN1593 (SEQ ID NO: 60), AN1594 (SEQ ID NO: 61), AN1595 (SEQ ID NO: 62), AN1596 (SEQ ID NO: 63), AN1597 (SEQ ID NO: 64), AN1598 (SEQ ID NO: 65), and AN1599 (SEQ ID NO: 1).

REFERENCES

Arvas et al., Comparison of protein coding gene contents of the fungal phyla Pezizomycotina and Saccharomycotina, BMC Genomics, 2007, Sep. 17; 8:325.

Altschul et al., Nucleic Acids Res., 1997, Sep. 1; 25(17): 3389-402, Gapped BLAST and PSI-BLAST: a new generation of protein database search programs.

Arnaud M B et al., "Aspergillus Genome Database" www.aspergillusgenome.org/(10.9.2010)

Bok J W, Hoffmeister D, Maggio-Hall L A, Murillo R, Glasner J D, Keller N P. Genomic mining for *Aspergillus* natural products. Chem Biol. 2006 January;13(1):31-7

Chiou C H, Miller M et al (2002) Chromosomal location plays a role in regulation of aflatoxin gene expression in *Aspergillus parasiticus*. Appl Environ Microbiol 68(1): 306-315

Current Protocols in Molecular Biology, John Wiley and Sons, Inc., 2004.

Davis M A, Hynes M J (1991) Regulatory circuits in *Aspergillus nidulans*. In: Bennett J W (ed) More gene manipulations in fungi. Academic, New York, pp 151-189

Galagan et al., J. E., Sequencing of *Aspergillus nidulans* and comparative analysis with *A. fumigatus* and *A. oryzae*, Nature 438 (7071), 1105-1115 (2005).

Jones et al., Molecular Biology of the Cell, Vol. 18, 2123-2136, June 2007

Kaminskyj S., Protocol by Susan G. W. Kaminskyj, Dept. Biology, Univ. Saskatchewan, 112 Science Place, Saskatoon, Saskatchewan, CANADA S7N 5E2, adapted from the Fungal Genetics Stock Center webpage, www.fgsc.net/fgn48/Kaminskyj.htm Kuorelahti et al., Molecular Microbiology (2006) 61(4), 1060-1068.

Lubertozzi, David; Keasling, Jay D, Journal of Industrial Microbiology & Biotechnology (2008), 35(10), 1191-1198 CODEN: JIMBFL; ISSN: 1367-5435

Miller B L, Miller K Y et al (1987) Position-dependent and position-independent mechanisms regulate cell-specific expression of the spoc1 gene-cluster of *Aspergillus-Nidulans*. Mol Cell Biol 7 (1):427-434

Mulder et al., Nucleic Acids Res., 2005, Jan. 1; 33(Database issue):D201-5, InterPro, progress and status in 2005.

Osbourn A, Secondary metabolic gene clusters: ecolutionary toolkits for chemical innovation. Trends in Genetics 26 (2010) 449-457.

Palmer J M, Keller N P. Curr Opin Microbiol. 2010 August; 13(4):431-6. Epub 2010 Jun. 2.

Pfaffl M. W., A new mathematical model for relative quantification in real-time RT-PCR., Nucleic Acids Res. 2001, 29(9):e45. Microsoft Excel spread sheet for the calculations was adapted from pathmicro.med.sc.edu/per/real-time-home.htmwit Ro D-K., Ouellet M., Paradise E. M., Burd H., Eng D, Paddon C. J., Newman J. D. and Keasling J. D., Induction of multiple pleiotropic drug resistance genes in yeast engineered to produce an increased level of anti-malarial drug precursor, artemisinic acid, BMC Biotechnology 2008, 8:83

Roze L V et al. (2007) The initiation and pattern of spread of histone H4 acetylation parallel the order of transcriptional activation of genes in the aflatoxin gene cluster. Mol. Microbiol. 66, 713-726.

Sakai K., Kinoshita H., Shimizu T., Nihira T. Construction of citrinin gene cluster exparession system in heterologous *Aspergillus oryzae*, J. Biosci. Bioeng (2008) 106(5), 466-472

Verdoes J. C., Punt P. J. et al. (1995) Molecular-genetic strain improvement for the overproduction of fungal proteins by filamentous fungi. Appl Microbiol Biotechnol 43(2):195-205

The invention claimed is:

1. A method for producing terpenes in fungi, comprising the steps of:
   (a) providing a nucleic acid encoding a transcription factor, wherein said transcription factor activates a terpene biosynthetic gene cluster, and wherein said transcription factor comprises a polypeptide having at least 90% sequence identity to SEQ ID NO: 74;
   (b) operably linking said nucleic acid to a promoter, to produce an expression construct;
   (c) transforming said expression construct into a host cell carrying a terpene biosynthetic gene cluster; and
   (d) cultivating said host cell under conditions which allow expression of the transcription factor, and which allow activation of the terpene biosynthetic gene cluster by the transcription factor.

2. The method of claim 1, wherein said terpene is ent-pimara-8(14),15-diene, or a derivative thereof.

3. The method of claim 1, wherein said transcription factor comprises a polypeptide having at least 95% sequence identity to SEQ ID NO: 74.

4. The method of claim 1, wherein the host cell is *Aspergillus nidulans*.

5. The method of claim 1, wherein the terpenes are diterpenoids.

6. A host fungus comprising a terpene biosynthetic gene cluster comprising the genes encoding:
   (a) a polypeptide having at least 90% identity to SEQ ID NO: 65, a polypeptide having at least 90% identity to SEQ ID NO: 63, a polypeptide having at least 90% identity to SEQ ID NO: 61 and
   (b) a polypeptide having at least 90% identity to SEQ ID NO: 67, a polypeptide having at least 94% identity to SEQ ID NO: 73, a polypeptide having at least 90% identity to SEQ ID NO: 69, a polypeptide having at least 90% identity to SEQ ID NO: 71, and wherein said host fungus has been transformed with an expression construct comprising a nucleic acid encoding a transcription factor, wherein said nucleic acid is operably linked to a promoter, and wherein said transcription factor comprises a polypeptide having at least 90% sequence identity to SEQ ID NO: 74.

7. The production host of claim 6, wherein the terpene biosynthetic gene cluster further comprises a nucleic acid sequence encoding a polypeptide having at least 90% identity to SEQ ID NO: 59.

8. A method for producing terpenes in fungi, comprising the steps of:
(a) providing a nucleic acid encoding a transcription factor, wherein said transcription factor activates a terpene biosynthetic gene cluster, and wherein said transcription factor comprises a polypeptide having at least 90% sequence identity to SEQ ID NO: 74;
(b) operably linking said nucleic acid to a promoter, to produce an expression construct;
(c) transforming said expression construct into a host cell carrying a terpene biosynthetic gene cluster;
(d) cultivating said host cell under conditions which allow expression of the transcription factor, and which allow activation of the terpene biosynthetic gene cluster by the transcription factor; and
(e) recovering the terpene product.

9. A method for producing terpenes, said method comprising cultivating a host fungus which comprises a terpene biosynthetic gene cluster comprising the genes encoding:
(a) a polypeptide having at least 90% identity to SEQ ID NO: 65, a polypeptide having at least 90% identity to SEQ ID NO: 63, a polypeptide having at least 90% identity to SEQ ID NO: 61 and
(b) a polypeptide having at least 90% identity to SEQ ID NO: 67, a polypeptide having at least 94% identity to SEQ ID NO: 73, a polypeptide having at least 90% identity to SEQ ID NO: 69, a polypeptide having at least 90% identity to SEQ ID NO: 71,
and wherein said host fungus has been transformed with an expression construct comprising a nucleic acid encoding a transcription factor, wherein said nucleic acid is operably linked to a promoter, and wherein said transcription factor comprises a polypeptide having at least 90% sequence identity to SEQ ID NO: 74.

10. The method of claim 9, wherein the terpene biosynthetic gene cluster further comprises a nucleic acid sequence encoding a polypeptide having at least 90% identity to SEQ ID NO: 59.

11. The method of claim 9, wherein said method further comprises the step of recovering the terpene product.

* * * * *

SEQUENCE LISTING

```
<160> NUMBER OF SEQ ID NOS: 74

<210> SEQ ID NO 1
<211> LENGTH: 2565
<212> TYPE: DNA
<213> ORGANISM: Aspergillus nidulans

<400> SEQUENCE: 1
atgtacccgt ggagttcgac aggaacgtca ccgttttcgc atcccgacaa tgaaggcgcg      60
gaatcggggg atatgagcat gggggaagag cagcagcaac cccaccagag gcgccagaaa     120
ttgtgagtaa aatgtgtcgc aaccgatgag accccgact tcgagaggaa tgtatttaga      180
```

```
gatcaccaac cgacgttttc gacctaacag caacaacctg cgcgcatgcc agtcctgccg    240
cgcttcgaaa gtacgatgcg accagcctaa cccgggcatg ccctgtcttc ggtgccagaa    300
atcaggcaag ccgtgcgtgg atgccgccag tcaaccgggg aagcgacagc gccaacctat    360
caacagtatc ctggagatgg agtcgcgaat cgaaacgata ttgtcgtccg cagaattgca    420
ggacagcgct ggggacgggg agactgccca ttccaccgca ctccgttcgc cttcccagtt    480
gtcgcaccac atccaaccgt ttcagcacct ccccatggga ttcgcgatac cgttcaatgg    540
tgagtctgcg tagatccagt ctggaatcgt ggcgagttac tttcatcgct aacatggcca    600
ccttccgtct gcctaggagg aaattccggg acggaagatc tgaactcgag catccgatca    660
tggctgaatg acaacatcac cgacctggat gctcgtacca cagagacaat cttcagtcat    720
tatttgacca acatggtgcc cacctttccg gtcgtcgtct ttgcgacagg caccacggcg    780
gccgacgtcc gacggaacaa ccctattctt tttctagcta ttctcgacgt ggcctcgtcg    840
ggattctgtg cgcttgagac gcagcggaaa ctgcgaaagc tgattgttca agcgtacgtg    900
cattgcatgc tgcgaaccga acagtatact ctcggattgc tccaggccct gattgtatcc    960
gccacatggt atcgcacgat tgagcctgtc gagccggggg agcagatgga tatctaccag   1020
atcagccaca cagcagccaa tatggccttg atcatgaggc taggggagag tttgaatgcc   1080
aaatcttggg gggtcccat gtttcctcgg cgggagatga aaagggtcc tggaagcgcc    1140 tttcaggcgg actcgctgga agctcggcgc gtgtggcttg ggtgtcatta tatttgctcg   1200
aagtgagaaa gacataccca agagcgcggc agcgttaacc tagtctatgc agtacctcca   1260
tgtccctccg cgcccaaac atcatgagat ggacccgtct gatggacgaa tgtctggagg    1320
tattggaaaa ttccccggcg gcccttctat cggacaggct tctgtgtcag catatccggc   1380
tgcagcatat cactgaagaa ttcgcgatgc atttgtccgc agaagaggct tcagctcccg   1440
cgaaatcccg agcgattcag atccaggtaa cccatcgtgc tttcaaacga cagctcagcg   1500
aatggcgtag gactgttggt gatggttggg atggtaactc ctccctgctt gtccttgatc   1560
gcctgcccag ccactgatgc ggattgtcta gagtccctcg agttttcgta ttatttctca   1620
tgcctgtaca taaacgaagt agcccactgc acagcgacga gtgatgatgt tcccgaagat   1680
aacgcccagc gcttgacgcc accaccaccg attgtggcaa tcgagccgca tgcgattacc   1740
gagtttatgg atacgataga taatatttt cgggtgttca cctcactgga tatgtcgacc   1800
attcgagccc tacccgcgat gtacctgatt cggataatct acacattcat catcctggtc   1860
aaactatact ttgcggcagc caaactacca gcgcaggacg ccgtgttgca agtcgacgga   1920
ctgcaggtct ctaggcgctt caatcgcgtg atccagatga ccgcaggatg gggcccgttg   1980
tggcctgcta cgaaactaac caccgtgttc accaagatgc ggtcgtggtt tgaaagcgga   2040
ggggataaca attgccagag gctgcagcag gccgcggcgt ggctcacggg atgggagctt   2100 aagccccccgt cccagggccg agacgctcac gccatgaaca tggccgaagt tgtctcggat   2160
gatggatcaa ttgtcgcttc cagctcacga ggtccggcat cctgggttcc gtcgctggcg   2220
tccacggacg tggatactct tgccttctcg cacgaacccc ccctcggcac tgagttttcg   2280
atagcccctc cacctttccg gtcaatgtct tgtgctacaa aatcatgttc tcctcaggcg   2340
ggagctgctg agtttatgca cgacgaggag gttccgcttg aaggccaacg tctgggggac   2400
ctcccgaata tagaccagat ggacgacgtg gcatggatt ggagccagta taccaacatg    2460
ggctttgact tgtacaatct agacgcgcca ttttgccaa accctccttc tggctttgat    2520
ccagacgcag caatgaagga taattgcgca gatagaaaca catga                   2565
```

<210> SEQ ID NO 2
<211> LENGTH: 1901
<212> TYPE: DNA
<213> ORGANISM: Aspergillus nidulans

<400> SEQUENCE: 2

| | | | | | |
|---|---|---|---|---|---|
| atggtcccca | acggcgagag | acggtggcga | tgccaagcgg | aaacgctagg ccgtaaagga | 60 |
| actagagatt | ccgctttgag | aggcggtgag | gggggcagaa | cggtggtaca gagggacctg | 120 |
| tttctggctc | tccgctgtcc | agcacaacgg | atttccagag | tagcgtcttt attgaataca | 180 |
| taaaggatat | tatacaaaat | agtggacagc | aacttatata | taatattatc tttaagttct | 240 |
| tatatagttg | agattcacgg | tatatattat | actgtataga | gtacaaattt atgcttctag | 300 |
| gtacttaaat | cggaacttac | taaatataaa | cagaggcctg | gcagcatatt aatttatttc | 360 |
| ggtttctcca | catttgtctt | acagaactcg | tcgatcagcg | aaaattcccc gcaaattgca | 420 |
| tgtgcactgg | gtaacgtgga | cgctgataac | tgtttgaatc | caccaccact acccaacagt | 480 |
| actgtcaacg | gtaagtgaag | caggggaaga | agccaaaat | gcaacgcaaa gcatgtgatc | 540 |
| agtgctatag | cagaaagaaa | aagtgtttga | tggacgcctg | ctcatccgtc tgcgttcgat | 600 |
| gcgagaagtt | gtccctcgct | tgcactgtat | tgcgccgagt | acggcggcct ggacggcccc | 660 |
| ctggacatgg | cctccctggg | gtagctaata | gattattggg | ggtttgggaa cgctcatcaa | 720 |
| cggaggggaa | ttcatgtctt | atttcagttg | atcatgagcg | agggaagccg ccgactgcgt | 780 |
| gtgatgctcc | agaggccaag | ctcagcgctc | ctgactctta | ccgactccct ccggaactgc | 840 |
| aggatagcga | cttttatctc | ctgagtgata | tctacatgtt | cggtccgacc tttgcgaggg | 900 |
| acctccatcg | agctttggag | tactgccatc | ggcactcccc | ccatctgctc gcagagatct | 960 |
| tccgcgccct | cggcagctgt | ctttcttggg | cacggcttgg | ggagctccca aagaccagg | 1020 |
| tcgatgttaa | gagcggcgcc | gtatcgattg | aaaagctgcg | gaatgcagag atcaagaacc | 1080 |
| tccacgatgc | tgttgcggtc | ctgatgctcg | ggcaagcact | ggccgcattt gactcacttg | 1140 |
| tcacatccac | cggggcgatg | tcgatcctac | gatgctcgct | ctccctgatt gcccgtggt | 1200 |
| atccggatat | tgctgaaata | cagctgcttg | agacgattgc | gattgctcca gtcttttggg | 1260 |
| acacagtctg | gtgcttactg | caccgcgaag | ttcccgttct | tcagcccttg gtcacttgga | 1320 |
| caagggttgt | cgatcgtgta | gcaggtctct | gcacttcttt | gctgccgata ctctacaatc | 1380 |
| tttgtgtctt | cggccagcgt | tggaaagacg | gagtcccaca | gccacagtgt atgctggaca | 1440 |
| gtattgaaca | acagattcgg | acgtggtctc | cagacgactc | ggcattgact ctgcagcgat | 1500 |
| acagcacgat | cgagatcctg | tccattcgca | cccaagccag | catgtatcgg acagcagccc | 1560 |
| tcctacttgt | ccattggatt | cgtcacccett | tggcgtcgcc | ggatcccacg tcaaccagcc | 1620 |
| ttgcgaatga | tattattagt | gctagagaag | aattttttcgc | gagcgccgga ccctctgcaa | 1680 |
| agttgcaaaa | cacgtctttt | ccgctatccc | tggctctgct | ggaagtaccg atttccccag | 1740 |
| acaggttctg | ggagagctcg | acttggcttc | gcactcggcc | tgcctgcgtt agacatctgt | 1800 |
| ccgcctttac | cggttatgtg | tgggaccagc | gatatgcagg | cttcgaaagc tcactctttg | 1860 |
| atctcgtcaa | gagcggccct | aatttgttc | ctgtgccgta | g | 1901 |

<210> SEQ ID NO 3
<211> LENGTH: 969
<212> TYPE: DNA
<213> ORGANISM: Aspergillus nidulans -continued

```
<400> SEQUENCE: 3
atgtttgaac tggagactcc gtctatcagc actctccagt gtcacatctt cgccgctgtt      60
tacctctgca atgcctcatt ccagaacatg gcgcatacca cgctgactat tgctgtgcgt     120
acggcccaaa ttctcggtct tcatctcgac ccacccgctg acctgccgcg accacagagg     180
gaactgcgta gatgcatctg gtggactctc tacgtggttg aaaccaagac ttgcatgaaa     240
cttggccgac catcatccgt gtccgaggtg acagaggcct gtcagctccc tgctgatgac     300
catgagcttg ctcggcagtc actgtcgaat attgcggctc gtggggacaa agtgacctgg     360
tttacctact gctgcctagt cacaactttg gtgctggcgg cgcatactgt ccactccagg     420
tactgggaca atgtgccgga ccttctggcg gcgaatggag caagaagttt gtacacagac     480
gccgcctctc tcaaacaggc ggcagaattt tttgcgttgc aaatgggcgt catcacagaa     540
tggttagaga ctgtccctga tgctatgaag acaggacgca gaggggcggg tgaaccttt    600 tcgacagacg gctctaagtt agacccagaa cgctatgcta caccatggtt gcagcgccaa     660
cggcttctgc tggagcatct ctaccataac atggtcatga atatctaccg atcctttatc     720
agttttcctt ctccgtcatg tccgccacct aatggcgttg tccaaaaaca tgcagtctcc     780
tgtgcgaagc atgcggctac catcacccat gtcctctgcg agacgttggc tactaatgac     840
ttcctcaaag gctggtacga ggcctatcag tggcaatgga acgcgatcct tcttttatgg     900
gtttcgtgct ggcttatccc actcactcag agagtgcggg cgcccgcgca gcattcgaca     960
cggcgataa                                                            969

<210> SEQ ID NO 4
<211> LENGTH: 30
<212> TYPE: DNA
<213> ORGANISM: Artificial Sequence
<220> FEATURE:
<223> OTHER INFORMATION: Primer

<400> SEQUENCE: 4
gcactagttc atgtgtttct atctgcgcaa                                       30

<210> SEQ ID NO 5
<211> LENGTH: 29
<212> TYPE: DNA
<213> ORGANISM: Artificial Sequence
<220> FEATURE:
<223> OTHER INFORMATION: Primer

<400> SEQUENCE: 5
gcactagtat gtacccgtgg agttcgaca                                        29

<210> SEQ ID NO 6
<211> LENGTH: 31
<212> TYPE: DNA
<213> ORGANISM: Artificial Sequence
<220> FEATURE:
<223> OTHER INFORMATION: Primer

<400> SEQUENCE: 6
gcactagtct acggcacagg aacaaaatta g                                     31

<210> SEQ ID NO 7
<211> LENGTH: 29
<212> TYPE: DNA
<213> ORGANISM: Artificial Sequence
<220> FEATURE:
<223> OTHER INFORMATION: Primer
```

-continued

<400> SEQUENCE: 7
ttgggcccat ggtccccaac ggcgagaga                                              29

<210> SEQ ID NO 8
<211> LENGTH: 30
<212> TYPE: DNA
<213> ORGANISM: Artificial Sequence
<220> FEATURE:
<223> OTHER INFORMATION: Primer

<400> SEQUENCE: 8
ttgggcccat gtttgaactg gagactccgt                                             30

<210> SEQ ID NO 9
<211> LENGTH: 30
<212> TYPE: DNA
<213> ORGANISM: Artificial Sequence
<220> FEATURE:
<223> OTHER INFORMATION: Primer

<400> SEQUENCE: 9
gcactagttt atcgccgtgt cgaatgctgc                                             30

<210> SEQ ID NO 10
<211> LENGTH: 9285
<212> TYPE: DNA
<213> ORGANISM: Aspergillus nidulans

<400> SEQUENCE: 10

| | | | | | |
|---|---|---|---|---|---|
| gcggccgcga | cagaagatga | tatttgaagga | gcacttttg | ggcttggctg | gagctagtgg | 60 |
| aggtcaacaa | tgaatgccta | ttttggttta | gtcgtccagg | cggtgagcac | aaaatttgtg | 120 |
| tcgtttgaca | agatggttca | tttaggcaac | tggtcagatc | agccccactt | gtagcagtag | 180 |
| cggcggcgct | cgaagtgtga | ctcttattag | cagacaggaa | cgaggacatt | attatcatct | 240 |
| gctgcttggt | gcacgataac | ttggtgcgtt | tgtcaagcaa | ggtaagtgaa | cgacccggtc | 300 |
| ataccttctt | aagttcgccc | ttcctcccctt | tatttcagat | tcaatctgac | ttacctattc | 360 |
| tacccaagca | aagcttcgat | taggaagtaa | ccatgagccc | agaacgacgc | ccggccgaca | 420 |
| tccgccgtgc | caccgaggcg | gacatgccgg | cggtctgcac | catcgtcaac | cactacatcg | 480 |
| agacaagcac | ggtcaacttc | cgtaccgagc | cgcaggaacc | gcaggagtgg | acggacgacc | 540 |
| tcgtccgtct | gcgggagcgc | tatccctggc | tcgtcgccga | ggtggacggc | gaggtcgccg | 600 |
| gcatcgccta | cgcgggtccc | tggaaggcac | gtaacgccta | cgactggacg | gccgagtcga | 660 |
| ccgtgtacgt | ctcccccgc | caccagcgga | cgggactggg | ctccacgctc | tacacccacc | 720 |
| tgctgaagtc | cctggaggca | cagggcttca | agagcgtggt | cgctgtcatc | gggctgcccca | 780 |
| acgacccgag | cgtgcgcatg | cacgaggcgc | tcggatatgc | ccccgcggc | atgctgcggg | 840 |
| cggccggctt | caagcacggg | aactggcatg | acgtgggttt | ctggcagctg | gacttcagcc | 900 |
| tgccggtacc | gcccgtccg | gtcctgcccg | tcaccgagat | ctgatccgtc | accgggatcc | 960 |
| acttaagcgg | ccgcccttgt | atctctacac | acaggctcaa | atcaataaga | agaacggttc | 1020 |
| gtcttttcg | tttatatctt | gcatcgtccc | aaagctattg | gcgggatatt | ctgtttgcag | 1080 |
| ttggctgact | tgaagtaatc | tctgcagatc | tttcgacact | gaaatacgtc | gagcctgctc | 1140 |
| cgcttggaag | cggcgaggag | cctcgtcctg | tcacaactac | caacatggag | tacgataagg | 1200 |
| gccagttccg | ccagctcatt | aagagccagt | tcatgggcgt | tggcatgatg | gccgtcatgc | 1260 |

```
atctgtactt caagtacacc aacgctcttc tgatccagtc gatcatccgc tgaaggcgct    1320
ttcgaatctg gttaagatcc acgtcttcgg gaagccagcg actggtgacc tccagcgtcc    1380
ctttaaggct gccaacagct ttctcagcca gggccagccc aagaccgaca aggcctccct    1440
ccagaacgcc gagaagaact ggaggggtgg tgtcaaggag gagtaagctc cttattgaag    1500
tcggaggacg gagcggtgtc aagaggatat tcttcgactc tgtattatag ataagatgat    1560
gaggaattgg aggtagcata gcttcatttg gatttgcttt ccaggctgag actctagctt    1620
ggagcataga gggtcctttg gctttcaata ttctcaagta tctcgagttt gaacttattc    1680
cctgtgaacc ttttattcac caatgagcat tggaatgaac atgaatctga ggactgcaat    1740
cgccatgagg ttttcgaaat acatccggat gtcgaaggct tggggcacct gcgttggttg    1800
aatttagaac gtggcactat tgatcatccg atagctctgc aaaggcgtt gcacaatgca     1860 agtcaaacgt tgctagcagt tccaggtgga atgttatgat gagcattgta ttaaatcagg    1920
agatatagca tgatctctag ttagctcacc acaaaagtca gacggcgtaa ccaaaagtca    1980
cacaacacaa gctgtaagga tttcggcacg gctacggaag acgagaagc cacttcagt     2040 ggactcgagt accatttaat tctatttgtg tttgatcgag acctaataca gccctacaa     2100 cgaccatcaa agtcgtatag ctaccagtga ggaagtggac tcaaatcgac ttcagcaaca    2160
tctcctggat aaactttaag cctaaactat acagaataag ataggtggag agcttatacc    2220
gagctcccaa atctgtccag atcatggttg accggtgcct ggatcttcct atagaatcat    2280
ccttattcgt tgacctagct gattctggag tgacccagag ggtcatgact tgagcctaaa    2340
atccgccgcc tccaccattt gtagaaaaat gtgacgaact cgtgagctct gtacagtgac    2400
cggtgactct ttctggcatg cggagagacg gacggacgca gagagaaggg ctgagtaata    2460
agccactggc cagacagctc tggcggctct gaggtgcagt ggatgattat taatccggga    2520
ccggccgccc ctccgccccg aagtggaaag gctggtgtgc ccctcgttga ccaagaatct    2580
attgcatcat cggagaatat ggagcttcat cgaatcaccg gcagtaagcg aaggagaatg    2640
tgaagccagg ggtgtatagc cgtcggcgaa atagcatgcc attaacctag gtacagaagt    2700
ccaattgctt ccgatctggt aaaagattca cgagatagta ccttctccga agtaggtaga    2760
gcgagtaccc ggcgcgtaag ctccctaatt ggcccatccg gcatctgtag ggcgtccaaa    2820
tatcgtgcct ctcctgcttt gcccggtgta tgaaaccgga aaggccgctc aggagctggc    2880
cagcggcgca gaccgggaac acaagctggc agtcgaccca tccggtgctc tgcactcgac    2940
ctgctgaggt ccctcagtcc ctggtaggca gcttttgcccc gtctgtccgc ccggtgtgtc    3000
ggcggggttg acaaggtcgt tgcgtcagtc caacatttgt tgccatattt tcctgctctc    3060
cccaccagct gctctttcct tttctcttc ttttcccatc ttcagtatat tcatcttccc     3120
atccaagaac ctttatttcc cctaagtaag tactttgcta catccatact ccatccttcc    3180
catcccttat tccttgaac ctttcagttc gagctttccc acttcatcgc agcttgacta    3240
acagctaccc cgcttgagca gacatcaggg cccatcgatt cgatatcact agtatgtacc    3300
cgtggagttc gacaggaacg tcaccgttt cgcatcccga caatgaaggc gcggaatcgg    3360
gggatatgag catgggggaa gagcagcagc aaccccacca gaggcgccag aaattgtgag    3420
taaaatgtgt cgcaaccgat gagaccccg acttcgagag gaatgtattt agagatcacc     3480
aaccgacgtt ttcgacctaa cagcaacaac ctgcgcgcat gccagtcctg ccgcgcttcg    3540
aaagtacgat gcgaccagcc taacccgggc atgccctgtc ttcggtgcca gaaatcaggc    3600
aagccgtgcg tggatgccgc cagtcaaccg gggaagcgac agcgccaacc tatcaacagt    3660
```

```
atcctggaga tggagtcgcg aatcgaaacg atattgtcgt ccgcagaatt gcaggacagc   3720
gctggggacg gggagactgc ccattccacc gcactccgtt cgccttccca gttgtcgcac   3780
cacatccaac cgtttcagca cctccccatg ggattcgcga taccgttcaa tggtgagtct   3840
gcgtagatcc agtctggaat cgtggcgagt tactttcatc gctaacatgg ccaccttccg   3900
tctgcctagg aggaaattcc gggacggaag atctgaactc gagcatccga tcatggctga   3960
atgacaacat caccgacctg gatgctcgta ccacagagac aatcttcagt cattatttga   4020
ccaacatggt gcccaccttt ccggtcgtcg tctttgcgac aggcaccacg gcggccgacg   4080
tccgacggaa caaccctatt cttttttctag ctattctcga cgtggcctcg tcgggattct   4140
gtgcgcttga gacgcagcgg aaactgcgaa agctgattgt caagcgtac gtgcattgca   4200 tgctgcgaac cgaacagtat actctcggat tgctccaggc cctgattgta ccgccacat   4260 ggtatcgcac gattgagcct gtcgagccgg gggagcagat ggatatctac cagatcagcc   4320
acacagcagc caatatggcc ttgatcatga ggctagggga gagtttgaat gccaaatctt   4380
gggggggtcc catgtttcct cggcgggaga tgaaaaaggg tcctggaagc gccttcagg   4440 cggactcgct ggaagctcgg cgcgtgtggc ttgggtgtca ttatatttgc tcgaagtgag   4500
aaagacatac ccaagagcgc ggcagcgtta acctagtcta tgcagtacct ccatgtccct   4560
ccgcgcccca acatcatga gatggacccg tctgatggac gaatgtctgg aggtattgga   4620
aaattccccg gcggcccttc tatcggacag gcttctgtgt cagcatatcc ggctgcagca   4680
tatcactgaa gaattcgcga tgcatttgtc cgcagaagag gcttcagctc ccgcgaaatc   4740
ccgagcgatt cagatccagg taacccatcg tgctttcaaa cgacagctca gcgaatggcg   4800
taggactgtt ggtgatggtt gggatggtaa ctcctccctg cttgtccttg atcgcctgcc   4860
cagccactga tgcggattgt ctagagtccc tcgagttttc gtattatttc tcatgcctgt   4920
acataaacga agtagcccac tgcacagcga cgagtgatga tgttcccgaa gataacgccc   4980
agcgcttgac gccaccacca ccgattgtgg caatcgagcc gcatgcgatt accgagttta   5040
tggatacgat agataatatt tttcgggtgt tcacctcact ggatatgtcg accattcgag   5100
ccctacccgc gatgtacctg attcggataa tctacacatt catcatcctg gtcaaactat   5160
actttgcggc agccaaacta ccagcgcagg acgccgtgtt gcaagtcgac ggactgcagg   5220
tctctaggcg cttcaatcgc gtgatccaga tgaccgcagg atggggcccg ttgtggcctg   5280
ctacgaaact aaccaccgtg ttcaccaaga tgcggtcgtg gtttgaaagc ggaggggata   5340
acaattgcca gaggctgcag caggccgcgg cgtggctcac gggatgggag cttaagcccc   5400
cgtcccaggg ccgagacgct cacgccatga acatggccga agttgtctcg gatgatggat   5460
caattgtcgc ttccagctca cgaggtccgg catcctgggt tccgtcgctg gcgtccacgg   5520
acgtggatac tcttgccttc tcgcacgaac ccccctcgg cactgagttt tcgatagccc   5580 ctccacccttt ccggtcaatg tcttgtgcta caaaatcatg ttctcctcag gcgggagctg   5640
ctgagtttat gcacgacgag gaggttccgc ttgaaggcca acgtctgggg gacctcccga   5700
atatagacca gatggacgac gtgggcatgg attggagcca gtataccaac atgggctttg   5760
acttgtacaa tctagacgcg ccattttttgc caaaccctcc ttctggcttt gatccagacg   5820
cagcaatgaa ggataattgc gcagatagaa acacatgaac tagtccgcgg ggatccactt   5880
aacgttactg aaatcatcaa acagcttgac gaatctggat ataagatcgt tggtgtcgat   5940
gtcagctccg gagttgagac aaatggtgtt caggatctcg ataagatacg ttcatttgtc   6000
```

```
caagcagcaa agagtgcctt ctagtgattt aatagctcca tgtcaacaag aataaaacgc    6060
gttttcgggt ttacctcttc cagatacagc tcatctgcaa tgcattaatg cattgactgc    6120
aacctagtaa cgccttcagg ctccggcgaa gagaagaata gcttagcaga gctattttca    6180 tttttcgggag acgagatcaa gcagatcaac ggtcgtcaag agacctacga gactgaggaa   6240
tccgctcttg gctccacgcg actatatatt tgtctctaat tgtactttga catgctcctc    6300
ttctttactc tgatagcttg actatgaaaa ttccgtcacc agccctgggt tcgcaaagat    6360
aattgcatgt ttcttccttg aactctcaag cctacaggac acacattcat cgtaggtata    6420
aacctcgaaa tcattcctac taagatggta tacaatagta accatgcatg gttgcctagt    6480
gaatgctccg taacacccaa tacgccggcc gaaacttttt tacaactctc ctatgagtcg    6540
tttacccaga atgcacaggt acacttgttt agaggtaatc cttcttttcta gaagtcctcg   6600 tgtactgtgt aagcgcccac tccacatctc cactcgacct gcaggcatgc aagcttggca    6660
ctggccgtcg ttttacaacg tcgtgactgg gaaaaccctg gcgttaccca acttaatcgc    6720
cttgcagcac atcccccttt cgccagctgg cgtaatagcg aagaggcccg caccgatcgc    6780
ccttcccaac agttgcgcag cctgaatggc gaatggcgcc tgatgcggta ttttctcctt    6840
acgcatctgt gcggtatttc acaccgcata tggtgcactc tcagtacaat ctgctctgat    6900
gccgcatagt taagccagcc ccgacacccg ccaacacccg ctgacgcgcc ctgacgggct    6960
tgtctgctcc cggcatccgc ttacagacaa gctgtgaccg tctccgggag ctgcatgtgt    7020
cagaggtttt caccgtcatc accgaaacgc gcgagacgaa agggcctcgt gatacgccta    7080 ttttttatagg ttaatgtcat gataataatg gtttcttaga cgtcaggtgg cacttttcgg   7140
ggaaatgtgc gcggaacccc tatttgttta ttttctaaa tacattcaaa tatgtatccg    7200
ctcatgagac aataaccctg ataaatgctt caataatatt gaaaaggaa gagtatgagt    7260 attcaacatt tccgtgtcgc ccttattccc ttttttgcgg cattttgcct tcctgttttt    7320
gctcacccag aaacgctggt gaaagtaaaa gatgctgaag atcagttggg tgcacgagtg    7380
ggttacatcg aactggatct caacagcggt aagatccttg agagttttcg ccccgaagaa    7440
cgttttccaa tgatgagcac ttttaaagtt ctgctatgtg gcgcggtatt atcccgtatt    7500
gacgccgggc aagagcaact cggtcgccgc atacactatt ctcagaatga cttggttgag    7560
tactcaccag tcacagaaaa gcatcttacg gatggcatga cagtaagaga attatgcagt    7620
gctgccataa ccatgagtga taacactgcg gccaacttac ttctgacaac gatcggagga    7680
ccgaaggagc taaccgcttt tttgcacaac atggggggatc atgtaactcg ccttgatcgt    7740
tgggaaccgg agctgaatga agccatacca aacgacgagc gtgacaccac gatgcctgta    7800
gcaatggcaa caacgttgcg caaactatta actggcgaac tacttactct agcttcccgg    7860
caacaattaa tagactggat ggaggcggat aaagttgcag gaccacttct gcgctcggcc    7920
cttccggctg gctggtttat tgctgataaa tctggagccg gtgagcgtgg gtctcgcggt    7980
atcattgcag cactggggcc agatggtaag ccctcccgta tcgtagttat ctacacgacg    8040
gggagtcagg caactatgga tgaacgaaat agacagatcg ctgagatagg tgcctcactg    8100
attaagcatt ggtaactgtc agaccaagtt tactcatata tactttagat tgatttaaaa    8160
cttcattttt aatttaaaag gatctaggtg aagatccttt ttgataatct catgaccaaa    8220
atcccttaac gtgagttttc gttccactga gcgtcagacc ccgtagaaaa gatcaaagga    8280
tcttcttgag atcctttttt tctgcgcgta atctgctgct tgcaaacaaa aaaaccaccg    8340
ctaccagcgg tggtttgttt gccggatcaa gagctaccaa ctctttttcc gaaggtaact    8400
```

```
ggcttcagca gagcgcagat accaaatact gtccttctag tgtagccgta gttaggccac    8460
cacttcaaga actctgtagc accgcctaca tacctcgctc tgctaatcct gttaccagtg    8520
gctgctgcca gtggcgataa gtcgtgtctt accgggttgg actcaagacg atagttaccg    8580
gataaggcgc agcggtcggg ctgaacgggg ggttcgtgca cacagcccag cttggagcga    8640
acgacctaca ccgaactgag atacctacag cgtgagctat gagaaagcgc cacgcttccc    8700
gaagggagaa aggcggacag gtatccggta agcggcaggg tcggaacagg agagcgcacg    8760
agggagcttc caggggggaaa cgcctggtat ctttatagtc ctgtcgggtt cgccacctc    8820 tgacttgagc gtcgattttt gtgatgctcg tcaggggggc ggagcctatg aaaaacgcc    8880 agcaacgcgg cctttttacg gttcctggcc ttttgctggc cttttgctca catgttcttt    8940
cctgcgttat cccctgattc tgtggataac cgtattaccg cctttgagtg agctgatacc    9000
gctcgccgca gccgaacgac cgagcgcagc gagtcagtga gcgaggaagc ggaagagcgc    9060
ccaatacgca aaccgcctct ccccgcgcgt tggccgattc attaatgcag ctggcacgac    9120
aggtttcccg actggaaagc gggcagtgag cgcaacgcaa ttaatgtgag ttagctcact    9180
cattaggcac cccaggcttt acactttatg cttccggctc gtatgttgtg tggaattgtg    9240
agcggataac aatttcacac aggaaacagc tatgaccatg attac              9285

<210> SEQ ID NO 11
<211> LENGTH: 8601
<212> TYPE: DNA
<213> ORGANISM: Aspergillus nidulans

<400> SEQUENCE: 11
gcggccgcga cagaagatga tattgaagga gcactttttg ggcttggctg gagctagtgg      60
aggtcaacaa tgaatgccta ttttggttta gtcgtccagg cggtgagcac aaaatttgtg     120
tcgtttgaca agatggttca tttaggcaac tggtcagatc agccccactt gtagcagtag     180
cggcggcgct cgaagtgtga ctcttattag cagacaggaa cgaggacatt attatcatct     240
gctgcttggt gcacgataac ttggtgcgtt tgtcaagcaa ggtaagtgaa cgacccggtc     300
ataccttctt aagttcgccc ttcctcccttt tatttcagat tcaatctgac ttacctattc     360
tacccaagca aagcttcgat taggaagtaa ccatgagccc agaacgacgc ccggccgaca     420
tccgccgtgc caccgaggcg gacatgccgg cggtctgcac catcgtcaac cactacatcg     480
agacaagcac ggtcaacttc cgtaccgagc cgcaggaacc gcaggagtgg acggacgacc     540
tcgtccgtct gcgggagcgc tatccctggc tcgtcgccga ggtggacggc gaggtcgccg     600
gcatcgccta cgcgggtccc tggaaggcac gtaacgccta cgactggacg gccgagtcga     660
ccgtgtacgt ctccccccgc caccagcgga cgggactggg ctccacgctc tacacccacc     720
tgctgaagtc cctggaggca cagggcttca agagcgtggt cgctgtcatc gggctgccca     780 acgaccgag cgtgcgcatg cacgaggcgc tcggatatgc ccccgcggc atgctgcggg     840 cggccggctt caagcacggg aactggcatg acgtgggttt ctggcagctg gacttcagcc     900
tgccggtacc gccccgtccg gtcctgcccg tcaccgagat ctgatccgtc accgggatcc     960
acttaagcgg ccgcccttgt atctctacac acaggctcaa atcaataaga agaacggttc    1020 gtcttttttcg tttatatctt gcatcgtccc aaagctattg gcgggatatt ctgtttgcag    1080
ttggctgact tgaagtaatc tctgcagatc tttcgacact gaaatacgtc gagcctgctc    1140
cgcttggaag cggcgaggag cctcgtcctg tcacaactac caacatggag tacgataagg    1200
```

```
gccagttccg ccagctcatt aagagccagt tcatgggcgt tggcatgatg ccgtcatgc     1260 atctgtactt caagtacacc aacgctcttc tgatccagtc gatcatccgc tgaaggcgct    1320
ttcgaatctg gttaagatcc acgtcttcgg gaagccagcg actggtgacc tccagcgtcc    1380
ctttaaggct gccaacagct ttctcagcca gggccagccc aagaccgaca aggcctccct    1440
ccagaacgcc gagaagaact ggaggggtgg tgtcaaggag gagtaagctc cttattgaag    1500
tcggaggacg gagcggtgtc aagaggatat tcttcgactc tgtattatag ataagatgat    1560
gaggaattgg aggtagcata gcttcatttg gatttgcttt ccaggctgag actctagctt    1620
ggagcataga gggtcctttg gctttcaata ttctcaagta tctcgagttt gaacttattc    1680
cctgtgaacc ttttattcac caatgagcat tggaatgaac atgaatctga ggactgcaat    1740
cgccatgagg ttttcgaaat acatccggat gtcgaaggct tggggcacct gcgttggttg    1800
aatttagaac gtggcactat tgatcatccg atagctctgc aaagggcgtt gcacaatgca    1860
agtcaaacgt tgctagcagt tccaggtgga atgttatgat gagcattgta ttaaatcagg    1920
agatatagca tgatctctag ttagctcacc acaaaagtca gacggcgtaa ccaaaagtca    1980
cacaacacaa gctgtaagga tttcggcacg gctacggaag acggagaagc caccttcagt    2040
ggactcgagt accatttaat tctatttgtg tttgatcgag acctaataca gccctacaa    2100 cgaccatcaa agtcgtatag ctaccagtga ggaagtggac tcaaatcgac ttcagcaaca    2160
tctcctggat aaactttaag cctaaactat acagaataag ataggtggag agcttatacc    2220
gagctcccaa atctgtccag atcatggttg accggtgcct ggatcttcct atagaatcat    2280
ccttattcgt tgacctagct gattctggag tgacccagag ggtcatgact tgagcctaaa    2340
atccgccgcc tccaccattt gtagaaaaat gtgacgaact cgtgagctct gtacagtgac    2400
cggtgactct ttctggcatg cggagagacg dacggacgca gagagaaggg ctgagtaata    2460
agccactggc cagacagctc tggcggctct gaggtgcagt ggatgattat taatccggga    2520
ccggccgccc ctccgcccg aagtggaaag gctggtgtgc ccctcgttga ccaagaatct    2580
attgcatcat cggagaatat ggagcttcat cgaatcaccg gcagtaagcg aaggagaatg    2640
tgaagccagg ggtgtatagc cgtcggcgaa atagcatgcc attaacctag gtacagaagt    2700
ccaattgctt ccgatctggt aaaagattca cgagatagta ccttctccga agtaggtaga    2760
gcgagtaccc ggcgcgtaag ctccctaatt ggcccatccg gcatctgtag ggcgtccaaa    2820
tatcgtgcct ctcctgcttt gcccggtgta tgaaaccgga aaggccgctc aggagctggc    2880
cagcggcgca gaccgggaac acaagctggc agtcgaccca tccggtgctc tgcactcgac    2940
ctgctgaggt ccctcagtcc ctggtaggca gctttgcccc gtctgtccgc ccggtgtgtc    3000
ggcggggttg acaaggtcgt tgcgtcagtc caacatttgt tgccatattt tcctgctctc    3060
cccaccagct gctctttct tttctctttc ttttcccatc ttcagtatat tcatcttccc     3120
atccaagaac ctttatttcc cctaagtaag tactttgcta catccatact ccatccttcc    3180
catcccttat tcctttgaac ctttcagttc gagctttccc acttcatcgc agcttgacta    3240
acagctaccc cgcttgagca gacatcaggg cccatggtcc ccaacggcga gagacggtgg    3300
cgatgccaag cggaaacgct aggccgtaaa ggaactagag attccgcttt gagaggcggt    3360
gaggggggca gaacggtggt acagagggac ctgtttctgg ctctccgctg tccagcacaa    3420
cggatttcca gagtagcgtc tttattgaat acataaagga tattatacaa aatagtggac    3480
agcaacttat atataatatt atctttaagt tcttatatag ttgagattca cggtatatat    3540
tatactgtat agagtacaaa tttatgcttc taggtactta aatcggaact tactaaatat    3600
```

```
aaacagaggc ctggcagcat attaatttat ttcggtttct ccacattttg cttacagaac  3660
tcgtcgatca gcgaaaattc cccgcaaatt gcatgtgcac tgggtaacgt ggacgctgat  3720
aactgtttga atccaccacc actacccaac agtactgtca acggtaagtg aagcagggga  3780
agaaagccaa aatgcaacgc aaagcatgtg atcagtgcta tagcagaaag aaaaagtgtt  3840
tgatggacgc ctgctcatcc gtctgcgttc gatgcgagaa gttgtccctc gcttgcactg  3900
tattgcgccg agtacggcgg cctggacggc cccctggaca tggcctccct ggggtagcta  3960
atagattatt gggggtttgg gaacgctcat caacggaggg gaattcatgt cttatttcag  4020
ttgatcatga gcgagggaag ccgccgactg cgtgtgatgc tccagaggcc aagctcagcg  4080
ctcctgactc ttaccgactc cctccggaac tgcaggatag cgactttat ctcctgagtg  4140 atatctacat gttcggtccg acctttgcga gggacctcca tcgagctttg gagtactgcc  4200
atcggcactc cccccatctg ctcgcagaga tcttccgcgc cctcggcagc tgtctttctt  4260
gggcacggct tggggagctc ccagaagacc aggtcgatgt taagagcggc gccgtatcga  4320
ttgaaaagct gcggaatgca gagatcaaga acctccacga tgctgttgcg gtcctgatgc  4380
tcgggcaagc actggccgca tttgactcac ttgtcacatc caccggggcg atgtcgatcc  4440
tacgatgctc gctctccctg atttgcccgt ggtatccgga tattgctgaa atacagctgc  4500
ttgagacgat tgcgattgct ccagtctttt gggacacagt ctggtgctta ctgcaccgcg  4560
aagttcccgt tcttcagccc ttggtcactt ggacaagggt tgtcgatcgt gtagcaggtc  4620
tctgcacttc tttgctgccg atactctaca atctttgtgt cttcggccag cgttggaaag  4680
acggagtccc acagccacag tgtatgctgg acagtattga caacagatt cggacgtggt  4740 ctccagacga ctcggcattg actctgcagc gatacagcac gatcgagatc ctgtccattc  4800
gcacccaagc cagcatgtat cggacagcag ccctcctact tgtccattgg attcgtcacc  4860
ctttggcgtc gccggatccc acgtcaacca gccttgcgaa tgatattatt agtgctagag  4920
aagaattttt cgcgagcgcc ggaccctctg caaagttgca aaacacgtct tttccgctat  4980
ccctggctct gctggaagta ccgatttccc cagacaggtt ctgggagagc tcgacttggc  5040
ttcgcactcg gcctgcctgc gttagacatc tgtccgcctt taccggttat gtgtgggacc  5100
agcgatatgc aggcttcgaa agctcactct ttgatctcgt caagagcggc cctaattttg  5160
ttcctgtgcc gtagactagt ccgcggggat ccacttaacg ttactgaaat catcaaacag  5220
cttgacgaat ctggatataa gatcgttggt gtcgatgtca gctccggagt tgagacaaat  5280
ggtgttcagg atctcgataa gatacgttca tttgtccaag cagcaaagag tgccttctag  5340
tgatttaata gctccatgtc aacaagaata aaacgcgttt tcgggtttac ctcttccaga  5400
tacagctcat ctgcaatgca ttaatgcatt gactgcaacc tagtaacgcc ttcaggctcc  5460
ggcgaagaga agaatagctt agcagagcta ttttcatttt cgggagacga gatcaagcag  5520
atcaacggtc gtcaagagac ctacgagact gaggaatccg ctcttggctc cacgcgacta  5580
tatatttgtc tctaattgta ctttgacatg ctcctcttct ttactctgat agcttgacta  5640
tgaaaattcc gtcaccagcc ctgggttcgc aaagataatt gcatgttct tccttgaact  5700 ctcaagccta caggacacac attcatcgta ggtataaacc tcgaaatcat tcctactaag  5760
atggtataca atagtaacca tgcatggttg cctagtgaat gctccgtaac acccaatacg  5820
ccggccgaaa cttttttaca actctcctat gagtcgttta cccagaatgc acaggtacac  5880
ttgtttagag gtaatccttc tttctagaag tcctcgtgta ctgtgtaagc gcccactcca  5940
```

```
catctccact cgacctgcag gcatgcaagc ttggcactgg ccgtcgtttt acaacgtcgt      6000
gactgggaaa accctggcgt tacccaactt aatcgccttg cagcacatcc ccctttcgcc      6060
agctggcgta atagcgaaga ggcccgcacc gatcgccctt cccaacagtt gcgcagcctg      6120
aatggcgaat ggcgcctgat gcggtatttt ctccttacgc atctgtgcgg tatttcacac      6180
cgcatatggt gcactctcag tacaatctgc tctgatgccg catagttaag ccagccccga      6240
cacccgccaa cacccgctga cgcgccctga cgggcttgtc tgctcccggc atccgcttac      6300
agacaagctg tgaccgtctc cgggagctgc atgtgtcaga ggttttcacc gtcatcaccg      6360
aaacgcgcga gacgaaaggg cctcgtgata cgcctatttt tataggttaa tgtcatgata      6420
ataatggttt cttagacgtc aggtggcact tttcggggaa atgtgcgcgg aacccctatt      6480
tgtttatttt tctaaataca ttcaaatatg tatccgctca tgagacaata accctgataa      6540
atgcttcaat aatattgaaa aaggaagagt atgagtattc aacatttccg tgtcgccctt      6600
attccctttt ttgcggcatt ttgccttcct gttttgctc acccagaaac gctggtgaaa       6660
gtaaaagatg ctgaagatca gttgggtgca cgagtgggt acatcgaact ggatctcaac       6720
agcggtaaga tccttgagag ttttcgcccc gaagaacgtt ttccaatgat gagcactttt      6780
aaagttctgc tatgtggcgc ggtattatcc cgtattgacg ccgggcaaga gcaactcggt      6840
cgccgcatac actattctca gaatgacttg gttgagtact caccagtcac agaaaagcat      6900
cttacgatgg catgacagt aagagaatta tgcagtgctg ccataaccat gagtgataac       6960
actgcggcca acttacttct gacaacgatc ggaggaccga aggagctaac cgcttttttg      7020
cacaacatgg gggatcatgt aactcgcctt gatcgttggg aaccggagct gaatgaagcc      7080
ataccaaacg acgagcgtga caccacgatg cctgtagcaa tggcaacaac gttgcgcaaa      7140
ctattaactg gcgaactact tactctagct tcccggcaac aattaataga ctggatggag      7200
gcggataaag ttgcaggacc acttctgcgc tcggcccttc cggctggctg gtttattgct      7260
gataaatctg gagccggtga gcgtgggtct cgcggtatca ttgcagcact ggggccagat      7320
ggtaagccct cccgtatcgt agttatctac acgacgggga gtcaggcaac tatggatgaa      7380
cgaaatagac agatcgctga gataggtgcc tcactgatta gcattggta actgtcagac       7440 caagtttact catatatact ttagattgat ttaaaacttc atttttaatt taaaaggatc      7500
taggtgaaga tcctttttga taatctcatg accaaaatcc cttaacgtga gttttcgttc      7560
cactgagcgt cagaccccgt agaaaagatc aaaggatctt cttgagatcc ttttttttctg      7620 cgcgtaatct gctgcttgca acaaaaaaa ccaccgctac cagcggtggt ttgtttgccg       7680
gatcaagagc taccaactct ttttccgaag gtaactggct tcagcagagc gcagatacca      7740
aatactgtcc ttctagtgta gccgtagtta ggccaccact tcaagaactc tgtagcaccg      7800
cctacatacc tcgctctgct aatcctgtta ccagtggctg ctgccagtgg cgataagtcg      7860
tgtcttaccg ggttggactc aagacgatag ttaccggata aggcgcagcg gtcgggctga      7920
acggggggtt cgtgcacaca gcccagcttg gagcgaacga cctacaccga actgagatac      7980
ctacagcgtg agctatgaga aagcgccacg cttcccgaag ggagaaaggc ggacaggtat      8040
ccggtaagcg gcagggtcgg aacaggagag cgcacgaggg agcttccagg gggaaacgcc      8100
tggtatcttt atagtcctgt cgggtttcgc cacctctgac ttgagcgtcg attttttgtga     8160 tgctcgtcag gggggcggag cctatggaaa aacgccagca acgcggcctt tttacggttc      8220 ctggccttttt gctggccttt tgctcacatg ttctttcctg cgttatcccc tgattctgtg     8280
gataaccgta ttaccgcctt tgagtgagct gataccgctc gccgcagccg aacgaccgag      8340
```

```
cgcagcgagt cagtgagcga ggaagcggaa gagcgcccaa tacgcaaacc gcctctcccc    8400
gcgcgttggc cgattcatta atgcagctgg cacgacaggt ttcccgactg gaaagcgggc    8460
agtgagcgca acgcaattaa tgtgagttag ctcactcatt aggcaccccca ggctttacac    8520
```

```
agtgagcgca acgcaattaa tgtgagttag ctcactcatt aggcacccca ggctttacac    8520
tttatgcttc cggctcgtat gttgtgtgga attgtgagcg ataacaatt tcacacagga    8580 aacagctatg accatgatta c                                              8601
```

<210> SEQ ID NO 12
<211> LENGTH: 7669
<212> TYPE: DNA
<213> ORGANISM: Aspergillus nidulans

<400> SEQUENCE: 12

```
gcggccgcga cagaagatga tattgaagga gcacttttg gcttggctg gagctagtgg      60 aggtcaacaa tgaatgccta ttttggttta gtcgtccagg cggtgagcac aaaatttgtg    120
tcgtttgaca agatggttca tttaggcaac tggtcagatc agccccactt gtagcagtag    180
cggcggcgct cgaagtgtga ctcttattag cagacaggaa cgaggacatt attatcatct    240
gctgcttggt gcacgataac ttggtgcgtt tgtcaagcaa ggtaagtgaa cgacccggtc    300
ataccttctt aagttcgccc ttcctccctt tatttcagat tcaatctgac ttacctattc    360
tacccaagca aagcttcgat taggaagtaa ccatgagccc agaacgacgc ccggccgaca    420
tccgccgtgc caccgaggcg gacatgccgg cggtctgcac catcgtcaac cactacatcg    480
agacaagcac ggtcaacttc cgtaccgagc cgcaggaacc gcaggagtgg acggacgacc    540
tcgtccgtct gcgggagcgc tatccctggc tcgtcgccga ggtggacggc gaggtcgccg    600
gcatcgccta cgcgggtccc tggaaggcac gtaacgccta cgactggacg gccgagtcga    660
ccgtgtacgt ctccccccgc caccagcgga cgggactggg ctccacgctc tacacccacc    720
tgctgaagtc cctggaggca cagggcttca gagcgtggt cgctgtcatc gggctgccca    780
acgacccgag cgtgcgcatg cacgaggcgc tcggatatgc ccccgcggc atgctgcggg    840 cggccggctt caagcacggg aactggcatg acgtgggttt ctggcagctg gacttcagcc    900
tgccggtacc gccccgtccg gtcctgcccg tcaccgagat ctgatccgtc accgggatcc    960
acttaagcgg ccgcccttgt atctctacac acaggctcaa atcaataaga gaacggttc    1020 gtcttttcg tttatatctt gcatcgtccc aaagctattg cgggatatt ctgtttgcag     1080 ttggctgact tgaagtaatc tctgcagatc tttcgacact gaaatacgtc gagcctgctc    1140
cgcttggaag cggcgaggag cctcgtcctg tcacaactac caacatggag tacgataagg    1200
gccagttccg ccagctcatt aagagccagt tcatgggcgt tggcatgatg gccgtcatgc    1260
atctgtactt caagtacacc aacgctcttc tgatccagtc gatcatccgc tgaaggcgct    1320
ttcgaatctg gttaagatcc acgtcttcgg gaagccagcg actggtgacc tccagcgtcc    1380
ctttaaggct gccaacagct ttctcagcca gggccagccc aagaccgaca aggcctccct    1440
ccagaacgcc gagaagaact ggaggggtgg tgtcaaggag gagtaagctc cttattgaag    1500
tcggaggacg gagcggtgtc aagaggatat tcttcgactc tgtattatag ataagatgat    1560
gaggaattgg aggtagcata gcttcatttg gatttgcttt ccaggctgag actctagctt    1620
ggagcataga gggtcctttg gctttcaata ttctcaagta tctcgagttt gaacttattc    1680
cctgtgaacc ttttattcac caatgagcat tggaatgaac atgaatctga ggactgcaat    1740
cgccatgagg ttttcgaaat acatccggat gtcgaaggct tggggcacct gcgttggttg    1800
```

```
aatttagaac gtggcactat tgatcatccg atagctctgc aaagggcgtt gcacaatgca    1860
agtcaaacgt tgctagcagt tccaggtgga atgttatgat gagcattgta ttaaatcagg    1920
agatatagca tgatctctag ttagctcacc acaaaagtca gacggcgtaa ccaaaagtca    1980
cacaacacaa gctgtaagga tttcggcacg gctacggaag acggagaagc caccttcagt    2040
ggactcgagt accatttaat tctatttgtg tttgatcgag acctaataca gcccctacaa    2100
cgaccatcaa agtcgtatag ctaccagtga ggaagtggac tcaaatcgac ttcagcaaca    2160
tctcctggat aaactttaag cctaaactat acagaataag ataggtggag agcttatacc    2220
gagctcccaa atctgtccag atcatggttg accggtgcct ggatcttcct atagaatcat    2280
ccttattcgt tgacctagct gattctggag tgacccagag ggtcatgact tgagcctaaa    2340
atccgccgcc tccaccattt gtagaaaaat gtgacgaact cgtgagctct gtacagtgac    2400
cggtgactct ttctggcatg cggagagacg gacggacgca gagagaaggg ctgagtaata    2460
agccactggc cagacagctc tggcggctct gaggtgcagt ggatgattat taatccggga    2520
ccggccgccc ctccgccccg aagtggaaag gctggtgtgc ccctcgttga ccaagaatct    2580
attgcatcat cggagaatat ggagcttcat cgaatcaccg gcagtaagcg aaggagaatg    2640
tgaagccagg ggtgtatagc cgtcggcgaa atagcatgcc attaacctag gtacagaagt    2700
ccaattgctt ccgatctggt aaaagattca cgagatagta ccttctccga agtaggtaga    2760
gcgagtaccc ggcgcgtaag ctccctaatt ggcccatccg gcatctgtag ggcgtccaaa    2820
tatcgtgcct ctcctgcttt gcccggtgta tgaaaccgga aaggccgctc aggagctggc    2880
cagcggcgca gaccgggaac acaagctggc agtcgaccca tccggtgctc tgcactcgac    2940
ctgctgaggt ccctcagtcc ctggtaggca gctttgcccc gtctgtccgc ccggtgtgtc    3000
ggcggggttg acaaggtcgt tgcgtcagtc caacatttgt tgccatattt tcctgctctc    3060
cccaccagct gctcttttct tttctctttc ttttcccatc ttcagtatat tcatcttccc    3120
atccaagaac ctttatttcc cctaagtaag tactttgcta catccatact ccatccttcc    3180
catcccttat tcctttgaac ctttcagttc gagctttccc acttcatcgc agcttgacta    3240
acagctaccc cgcttgagca gacatcaggg cccatgtttg aactggagac tccgtctatc    3300
agcactctcc agtgtcacat cttcgccgct gtttacctct gcaatgcctc attccagaac    3360
atggcgcata ccacgctgac tattgctgtg cgtacggccc aaattctcgg tcttcatctc    3420
gacccacccg ctgacctgcc gcgaccacag agggaactgc gtagatgcat ctggtggact    3480
ctctacgtgg ttgaaaccaa gacttgcatg aaacttggcc gaccatcatc cgtgtccgag    3540
gtgacagagg cctgtcagct ccctgctgat gaccatgagc ttgctcggca gtcactgtcg    3600
aatattgcgg ctcgtgggga caaagtgacc tggtttacct actgctgcct agtcacaact    3660
ttggtgctgg cggcgcatac tgtccactcc aggtactggg acaaatgtgc cgaccttctg    3720
gcggcgaatg gagcaagaag tttgtacaca cgccgcct ctctcaaaca ggcggcagaa    3780 tttttttgcgt tgcaaatggg cgtcatcaca gaatggttag agactgtccc tgatgctatg    3840
aagacaggac gcagaggggc gggtgaacct ttttcgacag acggctctaa gttagaccca    3900
gaacgctatg ctacaccatg gttgcagcgc caacggcttc tgctggagca tctctaccat    3960
aacatggtca tgaatatcta ccgatccttt atcagttttc cttctccgtc atgtccgcca    4020
cctaatggcg ttgtccaaaa acatgcagtc tcctgtgcga agcatgcggc taccatcacc    4080
catgtcctct gcgagacgtt ggctactaat gacttcctca aaggctggta cgaggcctat    4140
cagtggcaat ggaacgcgat ccttcttttta tgggtttcgt gctggcttat cccactcact    4200
```

```
cagagagtgc gggcgcccgc gcagcattcg acacggcgat aaactagtcc gcggggatcc    4260
acttaacgtt actgaaatca tcaaacagct tgacgaatct ggatataaga tcgttggtgt    4320
cgatgtcagc tccggagttg agacaaatgg tgttcaggat ctcgataaga tacgttcatt    4380
tgtccaagca gcaaagagtg ccttctagtg atttaatagc tccatgtcaa caagaataaa    4440
acgcgttttc gggtttacct cttccagata cagctcatct gcaatgcatt aatgcattga    4500
ctgcaaccta gtaacgcctt caggctccgg cgaagagaag aatagcttag cagagctatt    4560
ttcattttcg ggagacgaga tcaagcagat caacggtcgt caagagacct acgagactga    4620
ggaatccgct cttggctcca cgcgactata tatttgtctc taattgtact ttgacatgct    4680
cctcttcttt actctgatag cttgactatg aaaattccgt caccagccct gggttcgcaa    4740
agataattgc atgtttcttc cttgaactct caagcctaca ggacacacat tcatcgtagg    4800
tataaacctc gaaatcattc ctactaagat ggtatacaat agtaaccatg catggttgcc    4860
tagtgaatgc tccgtaacac ccaatacgcc ggccgaaact ttttttacaac tctcctatga    4920
gtcgtttacc cagaatgcac aggtacactt gtttagaggt aatccttctt tctagaagtc    4980
ctcgtgtact gtgtaagcgc ccactccaca tctccactcg acctgcaggc atgcaagctt    5040
ggcactggcc gtcgttttac aacgtcgtga ctgggaaaac cctggcgtta cccaacttaa    5100
tcgccttgca gcacatcccc ctttcgccag ctggcgtaat agcgaagagg cccgcaccga    5160
tcgcccttcc caacagttgc gcagcctgaa tggcgaatgg cgcctgatgc ggtattttct    5220
ccttacgcat ctgtgcggta tttcacaccg catatggtgc actctcagta caatctgctc    5280
tgatgccgca tagttaagcc agccccgaca cccgccaaca cccgctgacg cgccctgacg    5340
ggcttgtctg ctcccggcat ccgcttacag acaagctgtg accgtctccg ggagctgcat    5400
gtgtcagagg ttttcaccgt catcaccgaa acgcgcgaga cgaaagggcc tcgtgatacg    5460
cctattttta taggttaatg tcatgataat aatggtttct tagacgtcag gtggcacttt    5520
tcggggaaat gtgcgcggaa cccctatttg tttatttttc taaatacatt caaatatgta    5580
tccgctcatg agacaataac cctgataaat gcttcaataa tattgaaaaa ggaagagtat    5640
gagtattcaa catttccgtg tcgcccttat tcccttttttt gcggcatttt gccttcctgt    5700
ttttgctcac ccagaaacgc tggtgaaagt aaaagatgct gaagatcagt tgggtgcacg    5760
agtgggttac atcgaactgg atctcaacag cggtaagatc cttgagagtt ttcgccccga    5820
agaacgtttt ccaatgatga gcacttttaa agttctgcta tgtggcgcgg tattatcccg    5880
tattgacgcc gggcaagagc aactcggtcg ccgcatacac tattctcaga atgacttggt    5940
tgagtactca ccagtcacag aaaagcatct tacggatggc atgacagtaa gagaattatg    6000
cagtgctgcc ataaccatga gtgataacac tgcggccaac ttacttctga caacgatcgg    6060
aggaccgaag gagctaaccg cttttttgca acatgggg gatcatgtaa ctcgccttga    6120
tcgttgggaa ccggagctga tgaagccat accaaacgac gagcgtgaca ccacgatgcc    6180
tgtagcaatg gcaacaacgt tgcgcaaact attaactggc gaactactta ctctagcttc    6240
ccggcaacaa ttaatagact ggatggaggc ggataaagtt gcaggaccac ttctgcgctc    6300
ggcccttccg gctggctggt ttattgctga taaatctgga gccggtgagc gtgggtctcg    6360
cggtatcatt gcagcactgg ggccagatgg taagccctcc cgtatcgtag ttatctacac    6420
gacgggagt caggcaacta tggatgaacg aaatagacag atcgctgaga taggtgcctc    6480
actgattaag cattggtaac tgtcagacca agtttactca tatatacttt agattgattt    6540
```

```
aaaacttcat ttttaattta aaaggatcta ggtgaagatc cttttttgata atctcatgac    6600 caaaatccct taacgtgagt tttcgttcca ctgagcgtca gacccccgtag aaaagatcaa    6660 aggatcttct tgagatcctt tttttctgcg cgtaatctgc tgcttgcaaa caaaaaaacc    6720
accgctacca gcggtggttt gtttgccgga tcaagagcta ccaactcttt ttccgaaggt    6780
aactggcttc agcagagcgc agataccaaa tactgtcctt ctagtgtagc cgtagttagg    6840
ccaccacttc aagaactctg tagcaccgcc tacatacctc gctctgctaa tcctgttacc    6900
agtggctgct gccagtggcg ataagtcgtg tcttaccggg ttggactcaa gacgatagtt    6960
accggataag gcgcagcggt cgggctgaac ggggggttcg tgcacacagc ccagcttgga    7020
gcgaacgacc tacaccgaac tgagatacct acagcgtgag ctatgagaaa gcgccacgct    7080
tcccgaaggg agaaaggcgg acaggtatcc ggtaagcggc agggtcggaa caggagagcg    7140
cacgagggag cttccagggg gaaacgcctg gtatctttat agtcctgtcg ggtttcgcca    7200
cctctgactt gagcgtcgat ttttgtgatg ctcgtcaggg gggcggagcc tatgaaaaa    7260 cgccagcaac gcggcctttt tacggttcct ggccttttgc tggccttttg ctcacatgtt    7320
ctttcctgcg ttatcccctg attctgtgga taaccgtatt accgcctttg agtgagctga    7380
taccgctcgc cgcagccgaa cgaccgagcg cagcgagtca gtgagcgagg aagcggaaga    7440
gcgcccaata cgcaaaccgc ctctccccgc gcgttggccg attcattaat gcagctggca    7500
cgacaggttt cccgactgga aagcgggcag tgagcgcaac gcaattaatg tgagttagct    7560
cactcattag gcaccccagg ctttacactt tatgcttccg gctcgtatgt tgtgtggaat    7620
tgtgagcgga taacaatttc acacaggaaa cagctatgac catgattac                7669

<210> SEQ ID NO 13
<211> LENGTH: 20
<212> TYPE: DNA
<213> ORGANISM: Artificial Sequence
<220> FEATURE:
<223> OTHER INFORMATION: Primer

<400> SEQUENCE: 13
ccatccttcc catcccttat                                                 20

<210> SEQ ID NO 14
<211> LENGTH: 20
<212> TYPE: DNA
<213> ORGANISM: Artificial Sequence
<220> FEATURE:
<223> OTHER INFORMATION: Primer

<400> SEQUENCE: 14
caattctgcg gacgacaata                                                 20

<210> SEQ ID NO 15
<211> LENGTH: 20
<212> TYPE: DNA
<213> ORGANISM: Artificial Sequence
<220> FEATURE:
<223> OTHER INFORMATION: Primer

<400> SEQUENCE: 15
gcatcgtgga ggttcttgat                                                 20

<210> SEQ ID NO 16
<211> LENGTH: 20
<212> TYPE: DNA
<213> ORGANISM: Artificial Sequence
```

```
<220> FEATURE:
<223> OTHER INFORMATION: Primer

<400> SEQUENCE: 16
tcccagtacc tggagtggac                                               20

<210> SEQ ID NO 17
<211> LENGTH: 20
<212> TYPE: DNA
<213> ORGANISM: Artificial Sequence
<220> FEATURE:
<223> OTHER INFORMATION: Primer

<400> SEQUENCE: 17
gtaaggatct gtacggcaac                                               20

<210> SEQ ID NO 18
<211> LENGTH: 20
<212> TYPE: DNA
<213> ORGANISM: Artificial Sequence
<220> FEATURE:
<223> OTHER INFORMATION: Primer

<400> SEQUENCE: 18
agatccacat ctgttggaag                                               20

<210> SEQ ID NO 19
<211> LENGTH: 19
<212> TYPE: DNA
<213> ORGANISM: Artificial Sequence
<220> FEATURE:
<223> OTHER INFORMATION: Primer

<400> SEQUENCE: 19
gaatggcgta ggactgttg                                                19

<210> SEQ ID NO 20
<211> LENGTH: 22
<212> TYPE: DNA
<213> ORGANISM: Artificial Sequence
<220> FEATURE:
<223> OTHER INFORMATION: Primer

<400> SEQUENCE: 20
cgtatccata aactcggtaa tc                                            22

<210> SEQ ID NO 21
<211> LENGTH: 20
<212> TYPE: DNA
<213> ORGANISM: Artificial Sequence
<220> FEATURE:
<223> OTHER INFORMATION: Primer

<400> SEQUENCE: 21
tggaggtctt gacagagatg                                               20

<210> SEQ ID NO 22
<211> LENGTH: 20
<212> TYPE: DNA
<213> ORGANISM: Artificial Sequence
<220> FEATURE:
<223> OTHER INFORMATION: Primer

<400> SEQUENCE: 22
ctccattgtg caggtaattc                                               20
```

<210> SEQ ID NO 23
<211> LENGTH: 20
<212> TYPE: DNA
<213> ORGANISM: Artificial Sequence
<220> FEATURE:
<223> OTHER INFORMATION: Primer

<400> SEQUENCE: 23
gaccactctc aacaagatgc                                                    20

<210> SEQ ID NO 24
<211> LENGTH: 18
<212> TYPE: DNA
<213> ORGANISM: Artificial Sequence
<220> FEATURE:
<223> OTHER INFORMATION: Primer

<400> SEQUENCE: 24
ctgaaatgcg ttcctttg                                                      18

<210> SEQ ID NO 25
<211> LENGTH: 20
<212> TYPE: DNA
<213> ORGANISM: Artificial Sequence
<220> FEATURE:
<223> OTHER INFORMATION: Primer

<400> SEQUENCE: 25
aacacgtctt ttccgctatc                                                    20

<210> SEQ ID NO 26
<211> LENGTH: 20
<212> TYPE: DNA
<213> ORGANISM: Artificial Sequence
<220> FEATURE:
<223> OTHER INFORMATION: Primer

<400> SEQUENCE: 26
gatcaaagag tgagctttcg                                                    20

<210> SEQ ID NO 27
<211> LENGTH: 20
<212> TYPE: DNA
<213> ORGANISM: Artificial Sequence
<220> FEATURE:
<223> OTHER INFORMATION: Primer

<400> SEQUENCE: 27
tcgcagagtg caaaagatag                                                    20

<210> SEQ ID NO 28
<211> LENGTH: 20
<212> TYPE: DNA
<213> ORGANISM: Artificial Sequence
<220> FEATURE:
<223> OTHER INFORMATION: Primer

<400> SEQUENCE: 28
tctgtgacat cgacaaacac                                                    20

<210> SEQ ID NO 29
<211> LENGTH: 20
<212> TYPE: DNA
<213> ORGANISM: Artificial Sequence
<220> FEATURE:
<223> OTHER INFORMATION: Primer

<400> SEQUENCE: 29
agtactggga tttggctacg                                               20

<210> SEQ ID NO 30
<211> LENGTH: 20
<212> TYPE: DNA
<213> ORGANISM: Artificial Sequence
<220> FEATURE:
<223> OTHER INFORMATION: Primer

<400> SEQUENCE: 30
atgcaccaga tagttcttcg                                               20

<210> SEQ ID NO 31
<211> LENGTH: 19
<212> TYPE: DNA
<213> ORGANISM: Artificial Sequence
<220> FEATURE:
<223> OTHER INFORMATION: Primer

<400> SEQUENCE: 31
aacatgcagt ctcctgtgc                                                19

<210> SEQ ID NO 32
<211> LENGTH: 20
<212> TYPE: DNA
<213> ORGANISM: Artificial Sequence
<220> FEATURE:
<223> OTHER INFORMATION: Primer

<400> SEQUENCE: 32
acgaaaccca taaagaagg                                                20

<210> SEQ ID NO 33
<211> LENGTH: 25
<212> TYPE: DNA
<213> ORGANISM: Artificial Sequence
<220> FEATURE:
<223> OTHER INFORMATION: Primer

<400> SEQUENCE: 33
ggctgaaagt aatctatcag aaaag                                         25

<210> SEQ ID NO 34
<211> LENGTH: 19
<212> TYPE: DNA
<213> ORGANISM: Artificial Sequence
<220> FEATURE:
<223> OTHER INFORMATION: Primer

<400> SEQUENCE: 34
tccatcagga agaatccag                                                19

<210> SEQ ID NO 35
<211> LENGTH: 18
<212> TYPE: DNA
<213> ORGANISM: Artificial Sequence
<220> FEATURE:
<223> OTHER INFORMATION: Primer

<400> SEQUENCE: 35
catacgtggc tggagctg                                                 18

<210> SEQ ID NO 36

```
<211> LENGTH: 18
<212> TYPE: DNA
<213> ORGANISM: Artificial Sequence
<220> FEATURE:
<223> OTHER INFORMATION: Primer

<400> SEQUENCE: 36
gaagcgggaa gagtttgg                                                 18

<210> SEQ ID NO 37
<211> LENGTH: 20
<212> TYPE: DNA
<213> ORGANISM: Artificial Sequence
<220> FEATURE:
<223> OTHER INFORMATION: Primer

<400> SEQUENCE: 37
gaccagaggg gatgttctac                                               20

<210> SEQ ID NO 38
<211> LENGTH: 20
<212> TYPE: DNA
<213> ORGANISM: Artificial Sequence
<220> FEATURE:
<223> OTHER INFORMATION: Primer

<400> SEQUENCE: 38
actctgtccc tggaatgaag                                               20

<210> SEQ ID NO 39
<211> LENGTH: 20
<212> TYPE: DNA
<213> ORGANISM: Artificial Sequence
<220> FEATURE:
<223> OTHER INFORMATION: Primer

<400> SEQUENCE: 39
caagattctg cgtcttcatc                                               20

<210> SEQ ID NO 40
<211> LENGTH: 20
<212> TYPE: DNA
<213> ORGANISM: Artificial Sequence
<220> FEATURE:
<223> OTHER INFORMATION: Primer

<400> SEQUENCE: 40
taataggcga atctggtgtc                                               20

<210> SEQ ID NO 41
<211> LENGTH: 20
<212> TYPE: DNA
<213> ORGANISM: Artificial Sequence
<220> FEATURE:
<223> OTHER INFORMATION: Primer

<400> SEQUENCE: 41
gatattgtag ccctgtgtgc                                               20

<210> SEQ ID NO 42
<211> LENGTH: 20
<212> TYPE: DNA
<213> ORGANISM: Artificial Sequence
<220> FEATURE:
<223> OTHER INFORMATION: Primer

<400> SEQUENCE: 42
```

```
acatgctgat cacgtaaagc                                              20

<210> SEQ ID NO 43
<211> LENGTH: 20
<212> TYPE: DNA
<213> ORGANISM: Artificial Sequence
<220> FEATURE:
<223> OTHER INFORMATION: Primer

<400> SEQUENCE: 43
aaatagacga ctcccacctg                                              20

<210> SEQ ID NO 44
<211> LENGTH: 20
<212> TYPE: DNA
<213> ORGANISM: Artificial Sequence
<220> FEATURE:
<223> OTHER INFORMATION: Primer

<400> SEQUENCE: 44
ccgtctacca agtagtcacg                                              20

<210> SEQ ID NO 45
<211> LENGTH: 20
<212> TYPE: DNA
<213> ORGANISM: Artificial Sequence
<220> FEATURE:
<223> OTHER INFORMATION: Primer

<400> SEQUENCE: 45
tgggctttac tttcagatcc                                              20

<210> SEQ ID NO 46
<211> LENGTH: 18
<212> TYPE: DNA
<213> ORGANISM: Artificial Sequence
<220> FEATURE:
<223> OTHER INFORMATION: Primer

<400> SEQUENCE: 46
tgttcttggc cccttctc                                                18

<210> SEQ ID NO 47
<211> LENGTH: 19
<212> TYPE: DNA
<213> ORGANISM: Artificial Sequence
<220> FEATURE:
<223> OTHER INFORMATION: Primer

<400> SEQUENCE: 47
gtcacggcga tttatcttg                                               19

<210> SEQ ID NO 48
<211> LENGTH: 18
<212> TYPE: DNA
<213> ORGANISM: Artificial Sequence
<220> FEATURE:
<223> OTHER INFORMATION: Primer

<400> SEQUENCE: 48
cagcattgcc ttttgagg                                                18

<210> SEQ ID NO 49
<211> LENGTH: 18
<212> TYPE: DNA
```

```
<213> ORGANISM: Artificial Sequence
<220> FEATURE:
<223> OTHER INFORMATION: Primer

<400> SEQUENCE: 49
gaccgcaagt atctcgtg                                                 18

<210> SEQ ID NO 50
<211> LENGTH: 20
<212> TYPE: DNA
<213> ORGANISM: Artificial Sequence
<220> FEATURE:
<223> OTHER INFORMATION: Primer

<400> SEQUENCE: 50
tgggtaaatg cataaccatc                                               20

<210> SEQ ID NO 51
<211> LENGTH: 19
<212> TYPE: DNA
<213> ORGANISM: Artificial Sequence
<220> FEATURE:
<223> OTHER INFORMATION: Primer

<400> SEQUENCE: 51
gcagcagaag aagctgaac                                                19

<210> SEQ ID NO 52
<211> LENGTH: 21
<212> TYPE: DNA
<213> ORGANISM: Artificial Sequence
<220> FEATURE:
<223> OTHER INFORMATION: Primer

<400> SEQUENCE: 52
gggaggaggt tctgaataaa g                                             21

<210> SEQ ID NO 53
<211> LENGTH: 20
<212> TYPE: DNA
<213> ORGANISM: Artificial Sequence
<220> FEATURE:
<223> OTHER INFORMATION: Primer

<400> SEQUENCE: 53
gcatagctgg tggtatatcg                                               20

<210> SEQ ID NO 54
<211> LENGTH: 19
<212> TYPE: DNA
<213> ORGANISM: Artificial Sequence
<220> FEATURE:
<223> OTHER INFORMATION: Primer

<400> SEQUENCE: 54
agctagcatt cttgcgttc                                                19

<210> SEQ ID NO 55
<211> LENGTH: 20
<212> TYPE: DNA
<213> ORGANISM: Artificial Sequence
<220> FEATURE:
<223> OTHER INFORMATION: Primer

<400> SEQUENCE: 55
cattcattcg cttgtagagg                                               20
```

<210> SEQ ID NO 56
<211> LENGTH: 20
<212> TYPE: DNA
<213> ORGANISM: Artificial Sequence
<220> FEATURE:
<223> OTHER INFORMATION: Primer

<400> SEQUENCE: 56 cacctttct gtttccacac                                            20

<210> SEQ ID NO 57
<211> LENGTH: 26755
<212> TYPE: DNA
<213> ORGANISM: Aspergillus nidulans

<400> SEQUENCE: 57
cgtctaagat tttagctctg ttctcaatcc cctgtagtgc aacctgaaaa gtcaagagcg    60
caatcttagt gagggtctct tatttgttgt gactgttcta gcagggccat actcgaaaca   120
ttaagcccag gatgcccttg actgtaccca gtccgaactc agctggcaag cttcgaatg   180 ctgatagggt cacgtccaac gccatcccgg tccgttgccc gcaaccagta tttttggcat   240
aagcgtcttg ggcttgagta agcgattgga tgaccacctc ccaggagcat tggtagaatt   300
ttggctcccc gggttggctg tcgtcgtgct tgcggagaag gttttccaga tacctacgga   360
aaagaaagtc attcgatacc ccattacaat gggtacctat tggccgttaa gaggactcac   420
tcaatcgcct gctcctcatc ggagatgtac cgcttttcgc ttcgatcgta atcggccggc   480
gtcctgaagg ctgggtgatg agccctgct ttctttcgga tccatgcctc atcctcatcc   540
gttgctggct cagattttct ccatggaagg cgagaaaaat gatgcttctc tttgcccatg   600
atagtttctg aggctggaaa gctaagggt tcggtgtgtt gggaggagcg cagaagagat   660
aaaatggttt ctcgatattt atcccattgc tgacatgctg ccataggctc gccaggctga   720
gaggctgagc tgagtagtcg gaggcttccc tcttctactc gtctatgact gcttggtatt   780
gcaaggatac gtgaatgaca gcagtgggat gagcaatcag ctagcgcagc ctcgtttctt   840
cacgcctgag cctgttggcc acaacccttg ctactactga caggaccgcc gttctgtctt   900
cggctgacaa tgaaggtgcc cctcttctct catccacgac tgtttgttga tgcaaggata   960
tgttcatgac agcagtgagg tgaaggccac tactgcagcc tcgttactcc acgcctgagg  1020
ctgcggctag cactctcgtt aatgctgaca gggctgtcgc cgagttcacg taggagtatt  1080
aaatacgcgt cgtcagctct tgagtcgaca atcctcgcta cgtctcgttt ttctttcctc  1140
gcttaaagcc tttctgttcc ggtcttgcag cttactcaac taccttttc atagaaacca  1200 aggaggaaaa ataatgaaag aagagctgca catgtcttct attaatcccc aagaggattc  1260
caggcccaat cctgaccagg agctggtccc tatgtctaaa gaaccttcca cgtctactac  1320
cacgagcgct aggagtgaag gggcagaagc taggatgact gaggaggaga ccatgacggg  1380
aagaaagaga cggagaagag aacggaaagc tcaccggacg tgccaaaaaa ctctgaagat  1440
gaagtgaaag aggaccggag agtaaatctc ggggtaagat actataattt ccagggcttt  1500
atgaatcgaa ctgtggggga cgactgggat tatacgattg aagtctgcat cggccggccc  1560
aaccttctgg aagagattcg tgaagaactc aggaggagag aagcaatcga gaagaagaca  1620
tattccggca atcacaggcc tctgatggcc gaatctccgg aaaaaattgg tgaaaaccgc  1680
aagttgcacc gggtgcgcat aagatcgcca acagtgctca gtcatctcga acgtctaacc  1740

-continued

```
cgcaagctgg gtaacggttc tattttgaat gaggaggaca acttggtgtt tatgtacccc      1800
ttttacatct taggagtcta tcttgacgac atgcgtgaaa tcctagctga catggagaga      1860
ggagtgctgg cgtctggctc tatcccccc agcgagcctg agcccaaagg cctgtctcca      1920
tcagtgtcgc cgtcgcccat tgaccagatg aagtgcttcg ttcagttcgt ggaaagttcg      1980
atcctaccca tccataccgc tctccgacag ctggacgccc aaaccagtag aagattgtct      2040
tatgcggaaa tctcattgct gcttgagccg ggtgagctaa tctacgtcgc ccctcgctc       2100 atgacgacga agatgctgga tcgatcagca gtccagactg ttttccgatg tttgacccga      2160
atcccagccg atcatccgat cagcatcgac gacagcggct ggctgtcctc cgacatagga      2220
cgtcttctgg cggatgtata ctgcctggac catgatggtg aagaatacac cgtctgttgg      2280
cgcaaattgg agatggaata tttcgacggg gagaaagaca ttaccgcttt gcccttctat      2340
cccttgaaat ttcatccaaa ttacgagcga ttcctatcaa accgtgctcg gcagggaaca      2400
gcattccgag cgctcgtgga ggacgaaaac ttgcaccact actacgcagg ttggacgctc      2460
attactggtc tctttgaacg gaccgagtca gacggaaagt ccacggagtc caagccggag      2520
gattcagagt atgtcgatag cgaggtcttt ctggacaccc aggaagcacg acgacatatg      2580
gacgactggt cctctctccg tgagcctttc acaacgaagg gaagcttgc catcaacgac       2640 ggcgcgaagt tctgtctatg gcatatgact gaaaagaaga ctgtggcaga gaagctgaac      2700
aggatactca cgcgcgaaga ccttgtctac tggcgagcaa gggagcgata tctcctcgac      2760
aacaaatggg tgatcgacga ccgggtcttt ataaagagg aatggacgga cgaagatcta       2820
gcgctgcttc ccaaaagagt ctacggatac tcgttacggg acaggaagtt cttgcggctg      2880
gatgttgaca aattccgacc acacacgctc aagaccaaag ccaatctgga caagatcgag      2940
atcaaagata gccaccgcat gataattaga gctgcggtca agtcccattt tgacagagcg      3000
gcacaggtcc tgaaccgaga cgaggccact catgtccccg acatcttcga gggcaaaggc      3060
cgcggtctcg tcatccttct tcatggcgcc cccggcgtcg gcaagactgc cacagcggaa      3120
gcagtggcgc tagaattcga caaacccctta ttccagatta cttgcggcga tctgggcacg      3180
gggcccgcgg aggtggaaac gtcactgaag gcgattttcc gctacgcgaa catgtggagc      3240
tgcatcttgc tcctagatga agcagatgtt ttcctgactc agagaaaccg gacagatgta      3300
gagcggaatg cgttggtctc aggtacgtat ccattttgtc aggcagtgct ggtggaccag      3360
ttgtgctgca gatgcagata tgtaaatatg aaggcatcct cacactcaca ccgcaatagt      3420
gtttctcagg gtcctagagt actacagcgg ggtcctcttc ttgaccacca accgagttgg      3480
cgcactagac gaagccttcc ggtcgcgtgt gcacctcagc ctgttctatc cgcatctgaa      3540
ccgcactgat atggcgaaga tcctagagag caacctacag cgactaccgc gggacgacaa      3600
attgagccct ggagccactg caggcccaaa ccatgtcact gtgatggaca gtgagatccg      3660
ggagtttgtc ctgcagcagt tcgacgagca ctataagttg cacgagagag accctggaa       3720 tggacggcag atccgcaatg ctgttcatat tgccatgtgc ctggccttct ttgagaacgg      3780
caggaagggc cgcagggctc cggccattct aaccgcggag cattttcgca aagtccacga      3840
aactattgcc gaattcgagg actatttgag agccgctcga accgtggatg atgagaccct      3900
ggctcagatg gaaggattgc gatatgataa agaagggcag gcgtacaaaa ggcaacttgt      3960
cggctctact aaatttcaca gatggtcaga aaatgagcgt caagtgactc atcaacgcca      4020
atccgtccgc gagcaaggac agtcatatcg ggaaacgacc tcttatacac cgtctaggcg      4080
ctcattcctg ggtggggata tcgactctcc accagaatcc aggtttagcg gatcgggggc      4140
```

```
cgcagcgaga ccaaccagcc agcggtaccc gccgcgagaa atagacgact cccacctggc   4200
gcacgagaga tataacatgt ctgactctgg ttacggagag acaggtctgc gtgggactcc   4260
gaggaactac aatttgtctc cagacagacc acgaactcca aatcgtgact acttggtaga   4320
cggctcgcct gaatcagttc gctcaaggtc ttcggtccga gggagagatt gactttacgg   4380
gtaccctaag gggcagtaaa ggatgaagct aggtgttggt accattttgg cagatcaaca   4440
gtagttcgtg gaatcgagag gtagtgcctt ttcctgggct ggtgctggta ccctaacacg   4500
ggaactggaa ttcctcatta tctgatatat gaaaggggca gtcattcaag agtccatggg   4560
agtccagtta ctcgcgtcca gtcctcgaga aaaccattat catggacagt ggcgatata    4620 ccagaccgta tatctgtatg tacatttta tctctccttt tcggtccacc attctgcacc    4680
agccctctct tgtaacagca taggaagtaa tatagcccct tgtgttcgca gcacagctta   4740
gagaggtcgt aattggtaag ataggttgcc agctaaagta aactatataa attatataag   4800
cagttctgcc agtttgctaa tacgccaatc tcctataatg cccatgcgtt tacactgcaa   4860
tagtggccag ccagtgtctt ctatcagttg cccatggttg cacccatagc ctgatagtcc   4920
catcatcaga tgcagagcca atctgcttac cgtctgaaga gcggtgacta cataagacca   4980
gaaaccgcca gaagacgcta agagggtcca gtcgcgatc  attactcgac caattcgttc   5040
acgcggccag atccagcccc tggcggtcca tcgtgcaggc agtgtcaatt atgcgtattt   5100
acagaacagc aagagcagaa gctgactttg ggagtggggg gacagggtat ggttggagta   5160
taatatactc gtggatattg tcaccaagca gacaagttga acaagttggg atccattata   5220
tcagcatggg cttctttaga tcaacctcaa agtgtttatt tatatcttga agacgagaca   5280
taaagagcgg atagacaac  tgaggaattt tttgatgcca atatctctcc aggatagatc   5340
tgctgtggtt caattgtgat gaactgaaga atactgcgtg atttatgaaa agaggtttcc   5400
acaggacgag ctatttacac acgatagttc ttggtatacg gagatcgggc ttttctaggt   5460
ttcaatttag agcgaaatga gatatcaaca agccagaaga atacaggagc ggctatacgg   5520
caccggcttg ctaaagcttt attggaccta aacgagctct taaagtaaca tgattttggc   5580
acagttgaag agatttaaat cgggaaatca acggcctgcc atctcggctg agccgatcaa   5640
catattctat tcttcatccc actaaaataa ttctacatga agagaatgtc tagatcaact   5700
aactcagatg gggaacgatg gcggtcattt gctgattcta tcataaggct ggcgttgtct   5760
gcgaatcata cactgccgaa tctgctgggc tatacactga cggatggaca gcggcgagta   5820
cagcctgaac ggcgaacgac caggccttct atgttttccc ttccagtatg accatagacc   5880
tccttcagta ctattattcc aacgcattct ctgattttt  gactatcagt ttactgttcg   5940
gggtccctct acgagggatc tgttgagaat aagcacgggt gacggatccc gctgatcctt   6000
ctgctccgtc cgaatacaat atcacatcga agtaagacac aagcgagttc ccgattgcaa   6060
gtattaacac ccttagataa catcgttcag cctcgtctca agggatataa tcaacactga   6120
gctctatggc ctcgctattt gagtcaactc acattgacca acatgtcacc cccacttgac   6180
tctgccctgg agccactgtc cgaatacaag gaaacagcct ttcccagaac tgaaaaagac   6240
ccgtcgcagt acaaagagca cgaccttgta acgcctgaaa agaaatccaa gactgggtac   6300
ttttcgccgc gtggaagcca cagcagccac ggttctcacg actccagcgc ctcctccaat   6360
atcagcctcg acgacgcccg gatgtcagat gtgaacaatt cgccaaatgt attccatgac   6420
gacccagata cgatcgacga gaagttgtcg atgtactgga aggcggcgaa tgaaacggta   6480
```

```
gggcctggtt cactcatcag ccatgagagt tgaccttatc tcttttactc cacaggtgat    6540
tagagagccg tatgactaca tcgctgggat cccaggcaaa gagatccgcc gaaagctctt    6600
ggaggccttc aaccactggt acaaagttga cgaacagtcg tgccaggcta ttgcaaccac    6660
tgttggtatg gcacacaatg catccctgct gtatgttgca tccagtctct ggctcaatcg    6720
cgttttcacg agctaataag cactccacag catcgacgat attcaagaca gttccaagct    6780
ccgaagaggt gttccatgcg cacatgaagt gtttggcatc gcccagacca ttaactccgc    6840
caactatgtc tactttctgg cgcaaaacca gctgtttaga ctgcggagct ggccccaggc    6900
aatttcggta ttcaacgaag aaatggtcaa tttgcaccgc ggtcaaggca tggagctatt    6960
ctggcgggat aacctgctgc ctccgtccat ggatgactat ctgcagatga tcgctaacaa    7020
gacaggtgga ctgtttcgga tgatagtgcg gctgctccag acaagcagca gacaggtcat    7080
tgacgtcgag cagttggtgg atgttcttgg gctttacttt cagatcctcg acgactacaa    7140
gaatatcaga gaagagaagg ttcgtcttcg tcgaaccaga tcgagaacta agaagactg    7200
actacttcgc actagatggc cgcccagaaa gggttcttcg aagacctgac ggagggcaaa    7260
ttctcgttcc ccatttgcca tgcaatcgga aaggggcca gaacagaac tgctctgctc     7320
catatgttga ggctcaaaac ggatgacatg aagatcaagc aagaagcagt ctgcatactg    7380
gacaatgctg gcagtttaga ttacacgcga gaggtgcttt acgggctgga caggaaggct    7440
cgcagtctgc ttcgggagtt caagactccg aaccctttca tggaggctct tttggatgca    7500
atgttgagca gccttcaggc atgccattga ggtttatcag actgaatatg acagtcctgc    7560
gcatttgatg agataatgac attgtttctt cttgacttta tgtatctcta agggcctgtc    7620
ctaaacacta catatctttc cgaccatatc ggatcatgga ctatttctta gatacaagcg    7680
cagtacttat gcctatgttt accggggact tactcgggac acttgatccg gttggagctg    7740
tttctgctgc ccaatgctac tgtagaagac tgcattgcac actactacgg cgaaagggcc    7800
cagcacggcg actacgagca tggaaatgtt atggctaata gccactgatt cattcacatt    7860
cctagcttac agccgtataa aatagagata cagcattcgg aacgcatcat tcttcactag    7920
gagtgaattg atagggttga gtaggcgatc ccacggcgtg cagcggtgcc acgttctgcc    7980
acgttctact atgcgtggat gataggatat cccaattgtc agatttagcc tagaggcgta    8040
atcagctagc taacactacc gtttcggccc tgtctcgaat cctcccctat ggtgccgatc    8100
ccaacctgcc gaatgtggtc ggatccccct gcgatcctcc gatcccctgg acggattgcg    8160
gcggtggatt ttcagtagca taatttccct cagtacatct gactcttagt cagaaatgct    8220
aataaataca cgctgtggta tatactgaat gaattcgtgt agcgaaccgg aggctctctc    8280
tcccaaaacg ttcttgttca ggaagacagg acgtcaataa gaaacaccaa cagtcttccc    8340
acggccgcac caaacccaac gatatggaca ctttcacatc cctgacgcca ccgtggaatg    8400
caggaggggg cttcatgcga tcctatttcg actcggcggc ctcagcaggg aaggccgcca    8460
gggactttct ccggagccac gaacgttttt cccgagcatg cctgtgtata tgcatcggct    8520
acgctttgtc cgtatggatg ctgcctgtta ggatcccaat cacaatcgag ggcttcacga    8580
cgtcgctgac gataccccag acccagcgct tggatcaagg agacaccatt ctgcaagtgc    8640
atgctgaccc aagtgcgaag atccggatcc ataatgatag gtaagttagg cacaacacag    8700
agtcctgccg tgagaccaac tactaacaga catgcagtca tacagagtct cctatccagc    8760
atagcgaagc atggctggaa gctgttcgcc aggcctgtgg gagcagcgct gaggccgaaa    8820
cgcagatgct ggccatgcac cgaggtcttg cgaagcgaga cattgcaagt gtatcggtat    8880
```

```
cgtctgccga cggtagtggc caagcgcaag catatcagca ggtctatctc ttcaagtgtg    8940
gtgatgtcgc cggggctttt gataagagcg atgatgcccg gttgaaccgt gcctttgtac    9000
acaatatcac gatcggcgcc tatcttaata gccgggcaac aggagcttta tcgatcagcg    9060
cactcgcgta ctgggtaccc cagctcgtcc tggcggcagc attggccctg gctgtactcg    9120
ggtcatggaa tcccaagcaa aaggcctcct cgccttccgg accagcgacc agatcagcac    9180
gttcacgaac agtagtgact caaccccag tgccaaaggc agtggcagcc cgacccattg    9240
tcggttctgg ccacagcaaa cgtccatctg atgtggagat acgcgccatg cctgagagtc    9300
agatcatcga actgggcacg ctgggccaga tccccctta cagccttgaa cgcgcgctcc    9360
aggaccctct tcgggctgtc aaactgcgac ggcaaatcgt ctcccagcat caagccactg    9420
gcaacatcga cttcacaacg gacggctccg cgctcccgta cgaaggatac gactacaaag    9480
cagtcctcgg agcctgctgc gagaacgtga tcgggtatat gcccatccct gtgggcgtcg    9540
ccggtccgat caaaatcaac ggaaagatgg tgtttctccc catgtccacg acagagggcg    9600
cgctggttgc gagcacgaat cgtggctgca tggcgatcaa cgccggtgga ggcgtgactg    9660
ctctggtgct gggcgatggc atgacccgag cgcctatcgt tcgatttccc agtctcgaag    9720
aagccggcgc cgcaaaacaa tggctgggct ctgatgcagg atttctcatc attgaggacg    9780
cgttcaatgc atccagccgc ttcgctcggc ttcaaaacat taaggccacg gccgttggct    9840
cggacctcta tatccggttc acggccagca cgggcgacgc aatgggcatg aacatgatct    9900 ccaaagggt tgagcaagcg ctggaggcga tgcaaaagca cgggttcgag tctatggatg    9960
tcgtctcgct gtcggggaac ttctgtgcgg ataaaaaacc tgcggctgtg aactggattg    10020
aggggcgagg caagaccgtg accgcgcagg cgacaatacc tgaacatgcg gttcgagaaa    10080
cactcaagac cagtgtcgag gccctcgtgg agctcaacgt ctccaagaac ctggtgggca    10140
gtgctgttgc aggggctctg ggagggttca acgcccatgc cgccaatgtt gtcacggcga    10200
tttatcttgc cactggtcag gatcccgcac agaatgtgca aagcagcaac actctgaccg    10260
tgatgaaaaa gtgagtacac tgcctctaaa gatattctga tagatgttgc ggcgctaact    10320
cccgagcagt gtgaatggtg atttgcaaat ctctgttttc atgccttcca ttgaagtcgg    10380
caccgttggg ggagggacag tcctgggccc tcaaaaggca atgctgcaca tgatgggcgt    10440
ccaaggggcc gaccccgaac agccaggtag aaacgcacag gagctggccc tgctggtggc    10500
ggctggcgtg ctggctggag agctcagtct ttgctctgct ctgtcagcgg gctcgttggt    10560
gaaaagccac ttgacccata tcggaagaa aggatgatga gcatgatgac tatttcagaa    10620
tatgactata gagtagatga atcaggagag ggtctagatt atatgaaagc gtaacatagc    10680
aatagtgtct gggatctagg actactttt ttctaagtgt tgttctatat acctggctca    10740
tgcttctaca atacggttcc ttaggcatct gcagatgtct ctgagaagct aacaaccatc    10800
atattcaaca atatgcctcc tttgaacata actttggtgc tcgaggtctc gggctgtcga    10860
aagctggcgg tatcataggc ccagggtctt gattcatcaa tgtaaaaggt taggacacca    10920
tatagattag aagtgatcat gtagagttac tccattgtgc aggtaattca agcataaaac    10980
aatcatgtgc gagatcacat ccgactcgca atatctctaa agcgtaaatc tgcccgtaca    11040
catcagtcac gtcgcaaaac atctgcacct tctccagcat cctcatcttg gccctatcct    11100
gcgccgccat ctctgtcaag acctccaagc cccgcttcat gttggaccgc tcaaactcag    11160
cgagagagaa cagctgcttc tgccgaaccg catctgattt tggcccggcc tgggcaaact    11220
```

-continued

```
cgggaaagtt gacgcagttg agattcttct cgtcgcggtc acgggcaagc gatccgtaat    11280
cgttgtacat gcggcacatc acggcgagat ggcggcacat tgcttcagcc acatacttct    11340
cttcgcaggt ctgaaagcac gcggcgttgt gggacgcctg ctcgaacccc agcaggcact    11400
ggtagaaggc aaacgagtag gggcaggagg tgtggtcgga cgaggtggaa gacacccagc    11460
ggtagaagct ggagcgggcg gtctcgaagt cgtcgcgggt ggactccagt tgggcggcga    11520
agcggccgtt gtcgtcggcc tgctctatgt gcgacagcag gaagacctga agctcgttct    11580
tgacgcgctc gtactcgagg ggcgcggcgg ccttcacgct gggatggtcc atgacgtggt    11640
ggacgaaggc gctaaggacg cggctcacgt cgcttgggag ttgtgacccc atcttgatgc    11700
gtttggcttg cggtaggatc ctgtgaccgt ttgcgtctgc gtttcttgga ccagactggg    11760
cctggattgc gtcattcagc tccggtttgt ccttgaggtc gcggaagatc tcgtcgatgc    11820
aggaccgggt catggatctc tggctgctgt tcagtctgcc gactaccgct tccataaatt    11880
catcggcttg gtagttgagg aacgaaatca ccatcatctc gacaagggtt ttcgtggaga    11940
ggaaggtgtt cctgcggtta ttgcacaggg tccaggtgaa cggaatgtac tcaaaatact    12000
tgtcttcttc catgcccgtg cgagagaaga cggcaagacg tcggtcgcgc agctgtggca    12060
ggagcaggta tccttcgacg atggcagcgc ggaccttcca gagttccatg ctcgaaaaca    12120
ggggaagcat ggagtggaag cgtgcgaact cgatgacacg cttcttgctg acgatgaaca    12180
gattcgccag acaggctgga taagaacgtt cgaaggacac cttcagcgcg gcgaggacat    12240
agctcttact gaggagaatt gagctgtatg tcaccttctc tacccacaga tactccgctt    12300
tgtcgcctgc gctgttttgc aggaacttgc ggcctcgaga cacagccagc tgcacattcg    12360
tccacagctg attcaccacg ggcaactggc atgcgtgagc gatggtcaga atagcatatg    12420
ccgtctcttc gtgggagtgc gatccccagg atccgttctc gttctgagtc tgtagtgtgc    12480
gaaccaatgc ctgatacagg cagaccgata ctcgatctct gataaactga ctggaaatcg    12540
acttgagtcc gccatctgac catacctgca gcagcttccc aaacgcctca gccatgagca    12600
tggatggata gtacggggag aggttctgag agagtcagcg ctctgctatt ccatttctg    12660 ttgcgaaaag aagtgatacc catttatccc caatctcact gtcggccgtc caccagacat    12720
cacacagaaa ggccgctgct ttttcgatct ggggcgacac agtggccgca tcgggcgtat    12780
tcaacagcgc aagcaataca ttgctgtttg cagtgaagct gggatctctc tcgccgtgat    12840
aggtgcggaa gtgcatcggg ccctcgaatg catctattag tccctgggcc gagactggtt    12900
tgtccaacaa ggagaccgca ataagcgatt tggcggtatc gtcggcgtct gcctggatcg    12960
acggagctat acaacagaat ggttagctac gtgagggaga gtgatagagc catgttgtgg    13020
gatcgtacca aatcctacaa tacctcctcc tttgaccaac gcatcgcgaa gcatctcgcc    13080
gaggctgtcg gtgtcttcga taccgagatc gcctgtagaa tatccattgt ccaagagcgt    13140
ggtaagggcc tgaagttcag tcagctttga ttctagtcga gcaagctgtc cccttaccca    13200
cgagacctcg aaatactttg aaggatacgc gctcggcatt cctccagtgc ccctccggc    13260 gccattctgt agcaccaacc gcaagtactg ttcgcactcg tcgtcccagg aggaggaaaa    13320
catgagaaag gcgccgtgg acgatggcga gaacatgaaa gagccattga ccttctggtg    13380
cgccacttta tcaaagtcga tcatgcccac aaacgcctca agcgagtgca gcgcggtggt    13440
tctggcggag tacaggtact ccggcctgaa cttggagagc ttgatgcgat tcagccggtc    13500
gagctcggcg cgcccgtcaa attcaaactc gtgcccttc tcgcgcagga gccgcagaag    13560
cgcgggcaaa atgatttcaa agccaacgtg aacagtgtct tttacactcc acgcttgcag    13620
```

```
ttgtcgtgag agggccgcgc gtgcccgtcc gattcgctcc ttcatttctt ccacgggagg   13680
gtcggtgctg gcaatccggc tttctgcatg ggtctcgagg gccagtaagg aggctgcggt   13740
gttgaggata ccgtcgacgt cggaggcgta ggtctcccaa ctgccatcct ctagctgggt   13800
ccgcaggatg tattcgaagc attttggcag gagccattga cgcccttctg gtgtcgtctt   13860
ctggaccatg gacacccagg ccgtgtcgta gactgccgcg gacataaagc ccagctctcc   13920
atcttttgtc cggagctgtt ggaccagctg ggaggcttgc gtgcatagat ctgtcacgtc   13980
tgcgcaagtc atggttcgtc tgactgcgag gagaagctga gcatgtagac tgaacgatag   14040
agagggagtt ccaggtattt gatgtcagcc agagtcaacc tggacattgt tcaagaggca   14100
ctccagactg actattgcgg tcggtgacgg agtgaacggg cacggaggga tcatctttcg   14160
ccccggggga gcagtcctta aaatagcctg ggcactggct tatgtctcta ggagcaatgc   14220
ctgcagcctc aagattgtgt tcgagtcatg gaagtttgtc tatggattag acggactgac   14280
aggcctacca cccggcgaac tacatggggg ctgcatatat gctcaatccg gcggtaacag   14340
tcaccgagat aatcaattgc ttatggattg tctgcccaag ggaactagag ctctctggag   14400
agcatggaat cgtctacggc aagcaatatc atgagctgta attcattgtc aatccatgtt   14460
cggatgacct agcttcacca tcttgtctac cttagaccca tcaattgctt aaagctttcg   14520
agctagcagt cggaaggcca gatatgggcc gcaagatttc cctgggatat tccctgacgc   14580
acagagtgcg acacaatgag tcgtaggagc tgatatacac aaaattgatt gcatttctcg   14640
ctaatcagtg ttctagagac cctgaacttc cttagagaaa tgtaccgtcc ctataggggtt   14700 tcgcgtataa tcccggcggg tcgggggact gatccttcgg tgtcggaatg atccatcgct   14760
ccgatgcatg agttcccaat gaagtacttg aatatttcct tgtcccgtga tatagcatct   14820
gaacatttta attttctagt actctcaatg cacccccgaa tcccacgcgt cacccagcta   14880
tgaccgcgga tacgcttgtc gacgcaccgg ctctgccgca tcagaatggc agtacagaag   14940
agaaactgaa ggagcgcgga agctttggaa agctctacac gtacaaggtc agcaccgttt   15000
tcatgttatc cctatgagtc ggaaagccca gcatatggtc gcagggctaa ctggcaacag   15060
cggagccccc gagccctagg catccaagct gtcgcaaaat ccatcggctt ggagctggag   15120
caagtcgagc tgcagccggc caacggcgtc ccagacttct actggaacct gaacccgctg   15180
ggcaagaccc cgacgtttgt cggcgcagac ggcctggtgc tgacggagtg tatggcgatt   15240
gccctgcacg gtgcgttccc ccctcgactt acgatgatac gcttgctttt gtgctgaata   15300
acactcacaa gagcagtgac caacgaagac tcgacgacca cgctcctggg cagcagctcg   15360
ctcgacttcg tccagatcat ccgctggatc tcgttcacca acacggatgt cgtcacccgc   15420
atggcgtcct gggtccggcc gttgatcggc tacgcgccgt acagcaagga ggaggtgctc   15480
aaggcgcagc agcagacgac gcaggccatc ggcgtcttcg aggacagctt gcgcgaccgc   15540
aagtatctcg tgggcgaccg cctgacgctg gctgatatca tgtgtgtcag cttggtgtcg   15600
tttgggttcg cgcagatctt cgataaggag tggagggagg cctttccata cttttcgggc   15660
tggtacatga tggttatgca tttacccatc atgaaggcag tggtggagga ggtgccgttt   15720
gtcgaggagg gcttgccgaa tgcaccgccc acggagccgt tcagggcgcc ttagaacagt   15780
aatactgcga tctatatatg ggtagaataa ttgtggaaga tctggattaa tcagataggc   15840
ggatctgttc cgcagtatac agtatttagt cgagcaacta cttggtctct gggatgtata   15900
gaagatcagg tcaaatcttc gttgcttgct ctataaagta ctagtacatt ccacccaccc   15960
```

```
atacaaagcg acgaaaacaa caattgctta ttattcatcc tatcgatgaa ctgcctggtc   16020
cataaggctc tcagtatgat cccaaaccaa ctgaggtatc ttctgctccc gatactgcgc   16080
cagaatcttg gtgctcggcc taacatcccc cttccaattc aacaggtagg cgccactccc   16140
cggttcccca gtaatgcctt tagcgacctc gccagcctcc agcggaacac cctggggcac   16200
aatgccctgc tttgctgggt agtgtgccga gctcagatgg aaaagatgtc gctcgccact   16260
ctcgccgaga tccacggaaa acggcttcat gaacggccac acgaggtaat tgtagaaggt   16320
cgaaaccgga gctgggaagc tgttggtgta gatgttggtg ccaacgagac ccgggtagac   16380
gtgaatgaaa ctgacggccg ggtggtgcg ggcgaggtgc tccatgctca gggaggtcat   16440
ggtgatggag tgcttgtagg cgttgagcag ggagaagttg tgcttgaggt cgaggtcggc   16500
cgtgtttatg gagtactcga agccgccgcc gtagacgcta atcacgcggc ttgggctcga   16560
cgcctccagc agcgggagga ggttctgaat aaagcgcatc cgggagtagt agcggagagc   16620
gaagaggtag tcgatgcctt cgacggtttc tgtatctttt tgttagcgca aggtactccg   16680
tggacgggtc tccgtctgca taccgtttcg gccccctaga gaaatcccgc ccggggtcat   16740
gaagagaaag ttcagcttct tctgctgctg gagaatctgc tggcacgcgg cgtccacatt   16800
ccgtacgagc gacacatccg cctcgatgaa gtggaagcgg cccttggggt tcaattgctg   16860
cagttccgac aagaacggcc gggtgcgagc ctcgttgcga ccgatgatat aggccgtcgg   16920
gctgtcggcg taacgggcca gctggcgcag ggtgctctgg ccgatgccac tggtgccgcc   16980
aacaaacaag gccgtaatgt tggggagcgc ccgaaggccg gcgttagatg cttgcaccgt   17040
cttcagagag accattctcg ttctcaatgg aaggaatcaa aaacgaatgg aaggactgcg   17100
ctggccgtgt tatttacatc gaccactgaa agccacctcg gtgatcccac gccgaaggat   17160
cagccagagt gggcccacgc gatccctccc gtccgacggc gcagatcaga tcgtcacaat   17220
ccacattcca cagcggccat tcgttcgcat ttatcagatc accatgctgg acaagatggc   17280
tgcgaccagc agaacagtcg gtacctgtct acactgtctg aaccatggtt gatgcaacgt   17340
ctccccccgg cgtcaacgca gtggtgaatt actacgtgcc caacagcgat gggtctccgc   17400
ctgccaccaa cgacatggcc gtcatgctgg gccaaaagga catgatttcc cacaaaatgc   17460
gaatccgcga tctgcgccct tacaaggagg agtattcgct ggatcgcaac ggcttccagt   17520
acgcgacgat ccactccacg cttacggatg ccaccgacga gacccagatc aaagaggtct   17580
actaccgaga gattgagaaa ctggtccaag atatgtgcgt gtgctcgttc gcctccatga   17640
cgcgctagtc taatctgcat gaatactgca gcaccgggc caagcgggtg cttgccttcc   17700
accatgcagt gcgcacccgc accggcaacg agttcggcga gcagatcaaa gaccgctacc   17760
agggcgtcga ggggcccgcg tatcgcgtac acattgacca gacccccccag ggcgcgctca   17820 gcatcgtgca gtttatgttt cccgatctcg cggacgatgt ccgcaacggc agtttccagg   17880
tgatcaacgt ttggcgcccg ttgacgcggg tgcagcgtga cccctgatg gtggctgatg   17940 cggccgagat gccgccgag gacctgcttc taatcagccg gaagtattac aacgggctgc   18000
attcgtccaa ctttgtcatt aagtatgatg gtcgaatggc ggctggggag ggcccgacgg   18060
atgggctgag cggtgatgga aagcatagct ggtggtatat cggggaccag gagcccaccg   18120
aagcgttggt tttctcctca tctggcttcc gcaatggaaa ggcgatcatc ggcacggcac   18180
atggtgcgtt ctgtttgcct gatcaagatc agtacccagc tcgtcagagc attgagtgtc   18240
ggtgtgttgc tatctattga taaatcatgt ctagaccttt actcggcaga accaatgata   18300
aatgcatatg aacgcaagaa tgctagctca ttatatggcc atgatgagtc ccagatatag   18360
```

```
aacttgttca tctattgacg ctctgacgtc aacggagtga cgcaagaggg gacagctcgt   18420
gcatgaccaa tgctagctga tgctctagac gatttgtttc tctattcgga tattgatcta   18480
tgcaatttcc cgttaccatt caccgacgac atcgccgggc cgcctcgtgc gcattccgcg   18540
cggagctgcg taagaaaacc gcatcacaga aggaacaccg cagcttcgcc gattcccccc   18600
ttcgctcccg ctggtgtcgc gtcaggttac ttcgattgga aaataatcgg ccattgcaac   18660
aggattccca gcaccggaat gtttcagact tttcggatgc tgtttctcga gaggggagac   18720
cattgcctgg ttgttctggt tggtcggtgg gttgggaatt ttggctggaa tggttggaag   18780
agtggaatca cgccatgct aaaagcgctt gaactgggta tatgggaata ctcacctggc   18840
cgactgtagt tctcgcaatt cttgtcgaag ccgctggagc tctaagatga gttctgtttt   18900
cggtatcgtt gtgctcgatg ccgcgctctg atcggggctg atcgtcttcc tcccaaggcc   18960
tgttcctgta gatatactga cggtattctc gtcttggaag agaccccaag cttcgctatg   19020
tactggatta gctcctgagt ctggattcca tcatgatgat cgtaccgata tgtggccatt   19080
gtggtgggtc gtcaatgtaa tctaacagga gaagaataga cgaagggaag aggcggacag   19140
tgtacggtag agaggctgat gtcggcgggg ccacctatcc caggcgactc ccgtggggcg   19200
gtggagttat tactagcgtc gataaggata gagacgaagt cctcgtaatt attggatggc   19260
cgacatggcc gccttggccg cctatatagc ttactaaata ctgactaagc tattcagacc   19320
ccaagggcag gcggtcaaga aagcaatatg ccccgcctgt cgagtctggt catgtgacta   19380
acattgcaac gaatgactgt attgagagtc ttgatctcct aactacgatc tatataaaca   19440
atatatagct tttcgatagc ttcaaaaaaa atcctcatta tctgtaggta gctcagtttc   19500
tatggatagc tgtggattgt ctaagcggtg tgatcgtccc tttgcaaaaa aaaacagagt   19560
tatataataa tgggttaata gttacaggac agaaggtcct gcatctttat tggtaagtcg   19620
agcgtttgcc ggttgacatc tcgtttcttt ttggtctagt cagtgacact actatgaatg   19680
gttactgcct gtggattgag gattatcttg aaggattcaa gggatgatcc cttgccgacc   19740
cgccgacacc atccgtcgga gggagtcgta ggattgatta caggtaggag tgtatagtag   19800
gaattcttgt atagggtcgt cgagtttggg catatttagc ccagtattcc cgtcaacatg   19860
tcgactaaac tatgtgcatt gttgatacag ctaaaacaaa cttggagaaa cgctaagttc   19920
tgcagatatg gacaactata cctggcactc tgggaccctc atcccttccg attcaccatc   19980
atccattgat cgctcgcagc tctatctgga gatcctcggc gttcttagcg tggtctacct   20040
gctccaaacc ctggtcgcat attccaaatc cttcaaggcc ccttcgtgg gcttccgatt   20100 ctggtatgag ccgaaatggt tggtaggact acgtttctcc cagggcgctc tggcgcaggt   20160
caatgaagga tacgccaagg tacgcaatgc taccgttccc ccaggactct gtctaatgcg   20220
cttgacagta caagaacgcc atgttcaagg tcgcccgcaa cgactcagac atcctggtta   20280
tccccaacaa gtatgtcgag gaactgcgat ccctgcctga cgagaagatc agcgccatcc   20340
gcgcgcatat caagaatctc ctgggaaagt actcgaccac gctgatcctc ctggagagcg   20400
acctgcatac gcgcatgctg cagaccaagc tgacccctaa tctcggctcc ttcatcgagg   20460
tcatcgagtc ggagctcctc ttcgccatgg accaggagat ccccgcgaac ctagacgact   20520
ggcagagcgt caatgtgttc cacatcgttc ttcgcatcgt ggcgcgcatc tccgcacgcg   20580
tgttcttggg cgtccccgcc tgccgcaatg aggaatggct ccagacctct attcactaca   20640
ccgagaacgt ctttgcgacc gtcatgctgt tgcggcgcctt ccccaagtgg atgcacccga   20700
```

```
ttgtgggaca cctcctcccc agctactggg caatccacag gaacctgcgg accgcgaagc   20760
gcatcatcag tcccatggtg cgccagcgcc gcgcagaaga ggccaagcgg aacccggact   20820
atgtaaagcc caacgatctc ctccagtgga tgatggacgg cgcaaacgag aacgacgggc   20880
agcccgacaa gctggcgcac cgccagctcc tcctaagcct ggcttccatc cacacaacaa   20940
ccatggcggc ggcgcactgc ttctacgatc tctgccaaca tcccgagtac tttgagccgt   21000
tgcgcgagga gatcaacgac gtaattgccc aggatggcgg ctggaaaaag accactctca   21060
acaagatgcg caagctggac agcttttctta aagaaagcca acgcatcaac ccgcccagtc   21120
tctgtaggta ctccttgtca tatccgataa acaattccgc taacgctttc tccagtggca   21180
ttcaaccgca ttgtctcgga agacctgacg ctctcggacg gcaccctcct gcccaaagga   21240
acgcatttca gcatgccctc cgcggccatc ctccaggaca acggcgtgga acccggtgcc   21300
gaccaattcg atgggttccg atactacaag aagcgcctca accccgagga agccaacaag   21360
caccagttcg ccatgaccga caacaacaac ctccattttg ccacggcaa gtactcatgt   21420
cccggccgct tcttcgcctc caacgagatc aagatcatca tggcgcacct gttgaccgac   21480
tacgaattca ataccccccg gggcgcgaca aggccgcgga atctgacggc cgatgagaac   21540
ctgtatccag atccgtcggc acgtctgctc atgagacgac gggtggtggc tccgccgcag   21600
gcgtcgatca cgccgcagct tgtctcagcc tagaccggtg gagagggatg cctcgcctgt   21660
ggagtagccc aaggtcaatt gcggatatgt gattcgtgct caccagataa tgcgcatgta   21720
acgattttac tttcctttgt ggtgtctaat caatattaca catagaatta agcctaccag   21780
cggccaagct gcatctctcc tactagggaa tctagaccac tgtaatcacg gattccttcc   21840
gagtaggata gctcgctaag agcctacttt tccctgatcc gctggtcggt ctggggggggg   21900
ctttggcact aaaactagct taatatagaa atccaggagg cagcacgggg ctggcggcgg   21960
cccaaagtac caacgccact caggaaccat gtcgcaggac gggctctgct ccgtgcagta   22020
ttcgtctccc ctatcatggc tccataagag tcatcctctg gcagtgttac atcgtcccct   22080
tcgttgaacg ggagatatga caggccccaa cgcttgccta cgcgggcagt gaagtgttta   22140
acagagctaa gcgtactcga gcgtgagata tttgccaagt caacacccaa gacgcgattc   22200
tactcgtctg ctcgtaacgc cgcacgaata cagtcagcac tatctgcgca ccttgagaga   22260
ccatgttcag ccgctaccag cttagtctgg gcggatgggg ctgaaccctta ggcacccaat   22320
cttcaacgct cttttgtactc agtatcgaca caacttgccg tgtcattcgc ttttgacgcc   22380
agagacgacc agcgctagga ttcttgctgg ggctgctcaa ggccgttgat tctcgtgagc   22440
gcaatgcggg gtgcctatgc tgacgtagcc cctccttcag ccagctttct atcgcctctc   22500
tctcccttct gatccttgac tcctacctga ccaatataca acatgtaccc gtggagttcg   22560
acaggaacgt caccgttttc gcatcccgac aatgaaggcg cggaatcggg ggatatgagc   22620
atggggggaag agcagcagca accccaccag aggcgccaga aattgtgagt aaaatgtgtc   22680
gcaaccgatg agaccccccga cttcgagagg aatgtattta gagatcacca accgacgttt   22740
tcgacctaac agcaacaacc tgcgcgcatg ccagtcctgc cgcgcttcga agtacgatg   22800
cgaccagcct aacccgggca tgccctgtct tcggtgccag aaatcaggca agccgtgcgt   22860
ggatgccgcc agtcaaccgg ggaagcgaca cgccaacct atcaacagta tcctggagat   22920
ggagtcgcga atcgaaacga tattgtcgtc cgcagaattg caggacgcg ctggggacgg   22980
ggagactgcc cattccaccg cactccgttc gccttcccag ttgtcgcacc acatccaacc   23040
gtttcagcac ctcccccatgg gattcgcgat accgttcaat ggtgagtctg cgtagatcca   23100
```

```
gtctggaatc gtggcgagtt actttcatcg ctaacatggc caccttccgt ctgcctagga   23160
ggaaattccg ggacggaaga tctgaactcg agcatccgat catggctgaa tgacaacatc   23220
accgacctgg atgctcgtac cacagagaca atcttcagtc attatttgac caacatggtg   23280
cccacctttc cggtcgtcgt ctttgcgaca ggcaccacgg cggccgacgt ccgacggaac   23340
aaccctattc ttttctagc tattctcgac gtggcctcgt cgggattctg tgcgcttgag    23400
acgcagcgga aactgcgaaa gctgattgtt caagcgtacg tgcattgcat gctgcgaacc   23460
gaacagtata ctctcggatt gctccaggcc ctgattgtat ccgccacatg gtatcgcacg   23520
attgagcctg tcgagccggg ggagcagatg gatatctacc agatcagcca cacagcagcc   23580
aatatggcct tgatcatgag gctaggggag agtttgaatg ccaaatcttg gggggtccc    23640 atgtttcctc ggcgggagat gaaaaagggt cctggaagcg cctttcaggc ggactcgctg   23700
gaagctcggc gcgtgtggct tgggtgtcat tatatttgct cgaagtgaga aagacatacc   23760
caagagcgcg gcagcgttaa cctagtctat gcagtacctc catgtccctc cgcgcccaa    23820 acatcatgag atggacccgt ctgatggacg aatgtctgga ggtattggaa aattccccgg   23880
cggcccttct atcggacagg cttctgtgtc agcatatccg gctgcagcat atcactgaag   23940
aattcgcgat gcatttgtcc gcagaagagg cttcagctcc cgcgaaatcc cgagcgattc   24000
agatccaggt aacccatcgt gctttcaaac gacagctcag cgaatggcgt aggactgttg   24060
gtgatggttg ggatggtaac tcctccctgc ttgtccttga tcgcctgccc agccactgat   24120
gcggattgtc tagagtccct cgagttttcg tattatttct catgcctgta cataaacgaa   24180
gtagcccact gcacagcgac gagtgatgat gttcccgaag ataacgccca gcgcttgacg   24240
ccaccaccac cgattgtggc aatcgagccg catgcgatta ccgagtttat ggatacgata   24300
gataatattt ttcgggtgtt cacctcactg gatatgtcga ccattcgagc cctacccgcg   24360
atgtacctga ttcggataat ctacacattc atcatcctgg tcaaactata ctttgcggca   24420
gccaaactac cagcgcagga cgccgtgttg caagtcgacg gactgcaggt ctctaggcgc   24480
ttcaatcgcg tgatccagat gaccgcagga tggggcccgt tgtggcctgc tacgaaacta   24540
accaccgtgt tcaccaagat gcggtcgtgg tttgaaagcg gaggggataa caattgccag   24600
aggctgcagc aggccgcggc gtggctcacg ggatgggagc ttaagccccc gtcccagggc   24660
cgagacgctc acgccatgaa catggccgaa gttgtctcgg atgatggatc aattgtcgct   24720
tccagctcac gaggtccggc atcctgggtt ccgtcgctgg cgtccacgga cgtggatact   24780
cttgccttct cgcacgaacc cccctcggc actgagtttt cgatagcccc tccacctttc    24840
cggtcaatgt cttgtgctac aaaatcatgt tctcctcagg cgggagctgc tgagtttatg   24900
cacgacgagg aggttccgct tgaaggccaa cgtctggggg acctcccgaa atagaccag    24960 atggacgacg tgggcatgga ttggagccag tataccaaca tgggctttga cttgtacaat   25020
ctagacgcgc catttttgcc aaaccctcct tctggctttg atccagacgc agcaatgaag   25080
gataattgcg cagatagaaa cacatgatca tcccttggga ggttttctgg tttgcaacta   25140
gcgttctgag ctttgtgtgt ctttgattag atcgagcagt tcatggatat tattcacaca   25200
tgggcgagtc atatatggcc gcatccatgc atcttcaatc aatgatcaac cgctgaagat   25260
tactgtccta tgctctagtc tctatcctga accatcttga gaaatatctt catgttttca   25320 cttttctagat gctcttccaa gctctcctag gaagtttgtg gcgctcatac tgctgctttc   25380
catcgccgtt cgtggagtta gctggtgact gggaattttc agtagtcggt ataagtcgga   25440
```

```
ggagtcccaa tcgttcaggc cgtggggagt tttgcgattg gttttcgata ttccatccta    25500
tattagaagc tgtgcagagt cgtataacct atatccatat atatatcttg ggcctatagg    25560
atttccataa tgtagctagg tatagaaaca ccattgttac tagaagtcag aggggacctc    25620
tgttgcattt cctccacgat tctgatggaa aagatccaac aagcttgttg atagaacaat    25680
tattttcccg tttcccatct tgagttttta acagcatcaa attttagctt tcacaccact    25740
ttttgcattt aagaacatct ccagccaagt taagatcaga gcaaaataga ggatgctagg    25800
ccacttgcaa ccaagatttt tcaacagact acgaaaagaa ggcctttact gatggcctac    25860
cggccgctga gcacactaca tgagcagaat tccaactggc gatggcagaa gcatctgact    25920
aggcagaaat tagctcggtt aaagaggtgc cgatgcttag agcgagagca agtgtatatg    25980
gcagtgctcc tttccatctg gcattacgac gttgactcga gtggtttgct ctctcgtctc    26040
aaaggtgctg atcctaattg cagctgacac cttcgacatt gcaagataat acatctcata    26100
ctatgtgcat ttcggctaag gccgtttcat gtagagccat gtatgggatg catcaacaac    26160
cgaggactgt gaaagaggca acgtatggga ctacggacag gtattctaag acagggagga    26220
tttttgccag tagtctgaac ggacagttgc accgggactg ggatcggtgt tctaaacagt    26280
gccttacttt cgttgctggg agagatgcca tataacgcct ctctcgtccc ataccaatt    26340 acgtgtcagt gctccttgtc ctagtacaga aacagtctca aaataaacag atttggctag    26400
tgcatattat atacattgcc ccccgcaatt acgcaaagtg aagagttttg gcaaactcct    26460
cgatggtaat aaggcgtcct gtgacctgct ggatcgacca ctcaaccacc ttttctgttt    26520
ccacaccata gtacccatag tcctgaataa acagaaacat attcacaatg ctgtccgcac    26580
catcaggagg acagaaggat cggaacttgg actccggcat caccacatac ttaactgtcc    26640
tgccagacac cttgctgaga atctgcgcca cctctacaag cgaatgaatg caagacgagg    26700
ccccaagcac cttaccgtcg tacttctctg gctgctcgag aatggcacca acaaa        26755
```

<210> SEQ ID NO 58
<211> LENGTH: 2872
<212> TYPE: DNA
<213> ORGANISM: Aspergillus nidulans

<400> SEQUENCE: 58

```
atgaatcgaa ctgtggggga cgactgggat tatacgattg aagtctgcat cggccggccc      60
aaccttctgg aagagattcg tgaagaactc aggaggagag aagcaatcga gaagaagaca     120
tattccggca atcacaggcc tctgatggcc gaatctccgg aaaaaattgg tgaaaaccgc     180
aagttgcacc gggtgcgcat aagatcgcca acagtgctca gtcatctcga acgtctaacc     240
cgcaagctgg gtaacggttc tattttgaat gaggaggaca acttggtgtt tatgtacccc     300
ttttacatct taggagtcta tcttgacgac atgcgtgaaa tcctagctga catggagaga     360
ggagtgctgg cgtctggctc tatccccccc agcgagcctg agcccaaagg cctgtctcca     420
tcagtgtcgc cgtcgcccat tgaccagatg aagtgcttcg ttcagttcgt ggaaagttcg     480
atcctaccca tccataccgc tctccgacag ctggacgccc aaaccagtag aagattgtct     540
tatgcggaaa tctcattgct gcttgagccg ggtgagctaa tctacgtcgc ccctcgctc      600 atgacgacga agatgctgga tcgatcagca gtccagactg ttttccgatg tttgacccga     660
atcccagccg atcatccgat cagcatcgac gacagcggct ggctgtcctc cgacatagga     720
cgtcttctgg cggatgtata ctgcctggac catgatggtg aagaatacac cgtcgttggg     780
cgcaaattgg agatggaata tttcgacggg gagaaagaca ttaccgcttt gcccttctat     840
```

```
cccttgaaat tcatccaaa ttacgagcga ttcctatcaa accgtgctcg gcagggaaca    900
gcattccgag cgctcgtgga ggacgaaaac ttgcaccact actacgcagg ttggacgctc    960
attactggtc tctttgaacg gaccgagtca gacggaaagt ccacggagtc caagccggag   1020
gattcagagt atgtcgatag cgaggtcttt ctggacaccc aggaagcacg acgacatatg   1080
gacgactggt cctctctccg tgagcctttc acaacgaagg gaagccttgc catcaacgac   1140
ggcgcgaagt tctgtctatg gcatatgact gaaaagaaga ctgtggcaga aagctgaac    1200
aggatactca cgcgcgaaga ccttgtctac tggcgagcaa gggagcgata tctcctcgac   1260
aacaaatggg tgatcgacga ccgggtcttt ataaagagg aatggacgga cgaagatcta    1320
gcgctgcttc ccaaaagagt ctacggatac tcgttacggg acaggaagtt cttgcggctg   1380
gatgttgaca aattccgacc acacacgctc aagaccaaag ccaatctgga caagatcgag   1440
atcaaagata gccaccgcat gataattaga gctgcggtca gtcccatttt gacagagcg    1500
gcacaggtcc tgaaccgaga cgaggccact catgtccccg acatcttcga gggcaaaggc   1560
cgcggtctcg tcatccttct tcatggcgcc cccggcgtcg gcaagactgc cacagcggaa   1620
gcagtggcgc tagaattcga caaacccttaa ttccagatta cttgcggcga tctgggcacg   1680
gggcccgcgg aggtggaaac gtcactgaag gcgattttcc gctacgcgaa catgtggagc   1740
tgcatcttgc cctagatga agcagatgtt ttcctgactc agagaaaccg gacagatgta    1800
gagcggaatg cgttggtctc aggtacgtat ccattttgtc aggcagtgct ggtggaccag   1860
ttgtgctgca gatgcagata tgtaaatatg aaggcatcct cacactcaca ccgcaatagt   1920
gtttctcagg gtcctagagt actacagcgg ggtcctcttc ttgaccacca accgagttgg   1980
cgcactagac gaagccttcc ggtcgcgtgt gcacctcagc ctgttctatc cgcatctgaa   2040
ccgcactgat atggcgaaga tcctagagag caacctacag cgactaccgc gggacgacaa   2100
attgagccct ggagccactg caggcccaaa ccatgtcact gtgatggaca gtgagatccg   2160
ggagtttgtc ctgcagcagt tcgacgagca ctataagttg cacgagagag daccctggaa   2220
tggacggcag atccgcaatg ctgttcatat tgccatgtgc ctggccttct ttgagaacgg   2280
caggaagggc cgcagggctc cggccattct aaccgcggag catttcgca aagtccacga    2340
aactattgcc gaattcgagg actatttgag agccgctcga accgtggatg atgagaccct   2400
ggctcagatg gaaggattgc gatatgataa agaagggcag cgtacaaaa ggcaacttgt    2460
cggctctact aaatttcaca gatggtcaga aaatgagcgt caagtgactc atcaacgcca   2520
atccgtccgc gagcaaggac agtcatatcg ggaaacgacc tcttatacac cgtctaggcg   2580
ctcattcctg ggtggggata tcgactctcc accagaatcc aggtttagcg gatcggggc    2640
cgcagcgaga ccaaccagcc agcggtaccc gccgcgagaa atagacgact cccacctggc   2700
gcacgagaga tataacatgt ctgactctgg ttacggagag acaggtctgc gtgggactcc   2760
gaggaactac aattttgtctc cagacagacc acgaactcca aatcgtgact acttggtaga   2820
cggctcgcct gaatcagttc gctcaaggtc ttcggtccga gggagagatt ga            2872
```

<210> SEQ ID NO 59
<211> LENGTH: 924
<212> TYPE: PRT
<213> ORGANISM: Aspergillus nidulans

<400> SEQUENCE: 59

```
Met Asn Arg Thr Val Gly Asp Asp Trp Asp Tyr Thr Ile Glu Val Cys
1               5                   10                  15
```

-continued

```
Ile Gly Arg Pro Asn Leu Leu Glu Glu Ile Arg Glu Leu Arg Arg
             20                  25                  30
Arg Glu Ala Ile Glu Lys Lys Thr Tyr Ser Gly Asn His Arg Pro Leu
         35                  40                  45
Met Ala Glu Ser Pro Lys Ile Gly Glu Asn Arg Lys Leu His Arg
 50                  55                  60
Val Arg Ile Arg Ser Pro Thr Val Leu Ser His Leu Glu Arg Leu Thr
 65                  70                  75                  80
Arg Lys Leu Gly Asn Gly Ser Ile Leu Asn Glu Glu Asp Asn Leu Val
                 85                  90                  95
Phe Met Tyr Pro Phe Tyr Ile Leu Gly Val Tyr Leu Asp Met Arg
                100                 105                 110
Glu Ile Leu Ala Asp Met Glu Arg Gly Val Leu Ala Ser Gly Ser Ile
             115                 120                 125
Pro Pro Ser Glu Pro Glu Pro Lys Gly Leu Ser Pro Ser Val Ser Pro
130                 135                 140
Ser Pro Ile Asp Gln Met Lys Cys Phe Val Gln Phe Val Glu Ser Ser
145                 150                 155                 160
Ile Leu Pro Ile His Thr Ala Leu Arg Gln Leu Asp Ala Gln Thr Ser
                165                 170                 175
Arg Arg Leu Ser Tyr Ala Glu Ile Ser Leu Leu Leu Glu Pro Gly Glu
             180                 185                 190
Leu Ile Tyr Val Ala Pro Ser Leu Met Thr Thr Lys Met Leu Asp Arg
         195                 200                 205
Ser Ala Val Gln Thr Val Phe Arg Cys Leu Thr Arg Ile Pro Ala Asp
 210                 215                 220
His Pro Ile Ser Ile Asp Asp Ser Gly Trp Leu Ser Ser Asp Ile Gly
225                 230                 235                 240
Arg Leu Leu Ala Asp Val Tyr Cys Leu Asp His Asp Gly Glu Glu Tyr
                245                 250                 255
Thr Val Cys Trp Arg Lys Leu Glu Met Glu Tyr Phe Asp Gly Glu Lys
             260                 265                 270
Asp Ile Thr Ala Leu Pro Phe Tyr Pro Leu Lys Phe His Pro Asn Tyr
         275                 280                 285
Glu Arg Phe Leu Ser Asn Arg Ala Arg Gln Gly Thr Ala Phe Arg Ala
290                 295                 300
Leu Val Glu Asp Glu Asn Leu His His Tyr Tyr Ala Gly Trp Thr Leu
305                 310                 315                 320
Ile Thr Gly Leu Phe Glu Arg Thr Glu Ser Asp Gly Lys Ser Thr Glu
                325                 330                 335
Ser Lys Pro Glu Asp Ser Glu Tyr Val Asp Ser Glu Val Phe Leu Asp
             340                 345                 350
Thr Gln Glu Ala Arg Arg His Met Asp Asp Trp Ser Ser Leu Arg Glu
         355                 360                 365
Pro Phe Thr Thr Lys Gly Ser Leu Ala Ile Asn Asp Gly Ala Lys Phe
 370                 375                 380
Cys Leu Trp His Met Thr Glu Lys Lys Thr Val Ala Glu Lys Leu Asn
385                 390                 395                 400
Arg Ile Leu Thr Arg Glu Asp Leu Val Tyr Trp Arg Ala Arg Glu Arg
                405                 410                 415
Tyr Leu Leu Asp Asn Lys Trp Val Ile Asp Asp Arg Val Phe Ile Lys
             420                 425                 430
```

```
Glu Glu Trp Thr Asp Glu Asp Leu Ala Leu Leu Pro Lys Arg Val Tyr
            435                 440                 445

Gly Tyr Ser Leu Arg Asp Arg Lys Phe Leu Arg Leu Asp Val Asp Lys
450                 455                 460

Phe Arg Pro His Thr Leu Lys Thr Lys Ala Asn Leu Asp Lys Ile Glu
465                 470                 475                 480

Ile Lys Asp Ser His Arg Met Ile Ile Arg Ala Ala Val Lys Ser His
                485                 490                 495

Phe Asp Arg Ala Ala Gln Val Leu Asn Arg Asp Glu Ala Thr His Val
            500                 505                 510

Pro Asp Ile Phe Glu Gly Lys Gly Arg Gly Leu Val Ile Leu Leu His
        515                 520                 525

Gly Ala Pro Gly Val Gly Lys Thr Ala Thr Ala Glu Ala Val Ala Leu
530                 535                 540

Glu Phe Asp Lys Pro Leu Phe Gln Ile Thr Cys Gly Asp Leu Gly Thr
545                 550                 555                 560

Gly Pro Ala Glu Val Glu Thr Ser Leu Lys Ala Ile Phe Arg Tyr Ala
                565                 570                 575

Asn Met Trp Ser Cys Ile Leu Leu Asp Glu Ala Asp Val Phe Leu
            580                 585                 590

Thr Gln Arg Asn Arg Thr Asp Val Glu Arg Asn Ala Leu Val Ser Val
        595                 600                 605

Phe Leu Arg Val Leu Glu Tyr Tyr Ser Gly Val Leu Phe Leu Thr Thr
        610                 615                 620

Asn Arg Val Gly Ala Leu Asp Glu Ala Phe Arg Ser Arg Val His Leu
625                 630                 635                 640

Ser Leu Phe Tyr Pro His Leu Asn Arg Thr Asp Met Ala Lys Ile Leu
                645                 650                 655

Glu Ser Asn Leu Gln Arg Leu Pro Arg Asp Asp Lys Leu Ser Pro Gly
            660                 665                 670

Ala Thr Ala Gly Pro Asn His Val Thr Val Met Asp Ser Glu Ile Arg
        675                 680                 685

Glu Phe Val Leu Gln Gln Phe Asp Glu His Tyr Lys Leu His Glu Arg
        690                 695                 700

Gly Pro Trp Asn Gly Arg Gln Ile Arg Asn Ala Val His Ile Ala Met
705                 710                 715                 720

Cys Leu Ala Phe Phe Glu Asn Gly Arg Lys Gly Arg Arg Ala Pro Ala
                725                 730                 735

Ile Leu Thr Ala Glu His Phe Arg Lys Val His Glu Thr Ile Ala Glu
            740                 745                 750

Phe Glu Asp Tyr Leu Arg Ala Ala Arg Thr Val Asp Asp Glu Thr Leu
        755                 760                 765

Ala Gln Met Glu Gly Leu Arg Tyr Asp Lys Glu Gly Gln Ala Tyr Lys
        770                 775                 780

Arg Gln Leu Val Gly Ser Thr Lys Phe His Arg Trp Ser Glu Asn Glu
785                 790                 795                 800

Arg Gln Val Thr His Gln Arg Gln Ser Val Arg Glu Gln Gly Gln Ser
                805                 810                 815

Tyr Arg Glu Thr Thr Ser Tyr Thr Pro Ser Arg Arg Ser Phe Leu Gly
            820                 825                 830

Gly Asp Ile Asp Ser Pro Pro Glu Ser Arg Phe Ser Gly Ser Gly Ala
        835                 840                 845

Ala Ala Arg Pro Thr Ser Gln Arg Tyr Pro Pro Arg Glu Ile Asp Asp
```

-continued

```
    850                 855                 860

Ser His Leu Ala His Glu Arg Tyr Asn Met Ser Asp Ser Gly Tyr Gly
865                 870                 875                 880

Glu Thr Gly Leu Arg Gly Thr Pro Arg Asn Tyr Asn Leu Ser Pro Asp
                885                 890                 895

Arg Pro Arg Thr Pro Asn Arg Asp Tyr Leu Val Asp Gly Ser Pro Glu
            900                 905                 910

Ser Val Arg Ser Arg Ser Ser Val Arg Gly Arg Asp
        915                 920

<210> SEQ ID NO 60
<211> LENGTH: 1368
<212> TYPE: DNA
<213> ORGANISM: Aspergillus nidulans

<400> SEQUENCE: 60
atgtcacccc cacttgactc tgccctggag ccactgtccg aatacaagga aacagccttt      60
cccagaactg aaaaagaccc gtcgcagtac aaagagcacg accttgtaac gcctgaaaaa     120
gaaatccaga ctgggtactt ttcgccgcgt ggaagccaca gcagccacgg ttctcacgac     180
tccagcgcct cctccaatat cagcctcgac gacgcccgga tgtcagatgt gaacaattcg     240
ccaaatgtat tccatgacga cccagatacg atcgacgaga agttgtcgat gtactggaag     300
gcggcgaatg aaacggtagg gcctggttca ctcatcagcc atgagagttg accttatctc     360
ttttactcca caggtgatta gagagccgta tgactacatc gctgggatcc caggcaaaga     420
gatccgccga aagctcttgg aggccttcaa ccactggtac aaagttgacg aacagtcgtg     480
ccaggctatt gcaaccactg ttggtatggc acacaatgca tccctgctgt atgttgcatc     540
cagtctctgg ctcaatcgcg ttttcacgag ctaataagca ctccacagca tcgacgatat     600
tcaagacagt tccaagctcc gaagaggtgt tccatgcgca catgaagtgt ttggcatcgc     660
ccagaccatt aactccgcca actatgtcta ctttctggcg caaaaccagc tgtttagact     720
gcggagctgg ccccaggcaa tttcggtatt caacgaagaa atggtcaatt tgcaccgcgg     780
tcaaggcatg gagctattct ggcgggataa cctgctgcct ccgtccatgg atgactatct     840
gcagatgatc gctaacaaga caggtggact gtttcggatg atagtgcggc tgctccagac     900
aagcagcaga caggtcattg acgtcgagca gttggtggat gttcttgggc tttactttca     960
gatcctcgac gactacaaga atatcagaga agagaaggtt cgtcttcgtc gaaccagatc    1020
gagaactaaa gaagactgac tacttcgcac tagatggccg cccagaaagg gttcttcgaa    1080
gacctgacgg agggcaaatt ctcgttcccc atttgccatg caatcggaga aggggccaag    1140
aacagaactg ctctgctcca tatgttgagg ctcaaaacgg atgacatgaa gatcaagcaa    1200
gaagcagtct gcatactgga caatgctggc agtttagatt acacgcgaga ggtgctttac    1260
gggctggaca ggaaggctcg cagtctgctt cgggagttca agactccgaa ccctttcatg    1320
gaggctcttt tggatgcaat gttgagcagc cttcaggcat gccattga                 1368

<210> SEQ ID NO 61
<211> LENGTH: 397
<212> TYPE: PRT
<213> ORGANISM: Aspergillus nidulans

<400> SEQUENCE: 61

Met Ser Pro Pro Leu Asp Ser Ala Leu Glu Pro Leu Ser Glu Tyr Lys
1               5                   10                  15
```

Glu Thr Ala Phe Pro Arg Thr Glu Lys Asp Pro Ser Gln Tyr Lys Glu
            20                  25                  30

His Asp Leu Val Thr Pro Glu Lys Glu Ile Gln Thr Gly Tyr Phe Ser
        35                  40                  45

Pro Arg Gly Ser His Ser His Gly Ser His Asp Ser Ser Ala Ser
    50                  55                  60

Ser Asn Ile Ser Leu Asp Asp Ala Arg Met Ser Asp Val Asn Asn Ser
65                  70                  75                  80

Pro Asn Val Phe His Asp Asp Pro Asp Thr Ile Asp Glu Lys Leu Ser
                85                  90                  95

Met Tyr Trp Lys Ala Ala Asn Glu Thr Val Ile Arg Glu Pro Tyr Asp
            100                 105                 110

Tyr Ile Ala Gly Ile Pro Gly Lys Glu Ile Arg Arg Lys Leu Leu Glu
            115                 120                 125

Ala Phe Asn His Trp Tyr Lys Val Asp Glu Gln Ser Cys Gln Ala Ile
        130                 135                 140

Ala Thr Thr Val Gly Met Ala His Asn Ala Ser Leu Leu Ile Asp Asp
145                 150                 155                 160

Ile Gln Asp Ser Ser Lys Leu Arg Arg Gly Val Pro Cys Ala His Glu
                165                 170                 175

Val Phe Gly Ile Ala Gln Thr Ile Asn Ser Ala Asn Tyr Val Tyr Phe
            180                 185                 190

Leu Ala Gln Asn Gln Leu Phe Arg Leu Arg Ser Trp Pro Gln Ala Ile
        195                 200                 205

Ser Val Phe Asn Glu Glu Met Val Asn Leu His Arg Gly Gln Gly Met
210                 215                 220

Glu Leu Phe Trp Arg Asp Asn Leu Leu Pro Pro Ser Met Asp Asp Tyr
225                 230                 235                 240

Leu Gln Met Ile Ala Asn Lys Thr Gly Gly Leu Phe Arg Met Ile Val
                245                 250                 255

Arg Leu Leu Gln Thr Ser Ser Arg Gln Val Ile Asp Val Glu Gln Leu
            260                 265                 270

Val Asp Val Leu Gly Leu Tyr Phe Gln Ile Leu Asp Asp Tyr Lys Asn
        275                 280                 285

Ile Arg Glu Glu Lys Met Ala Ala Gln Lys Gly Phe Phe Glu Asp Leu
    290                 295                 300

Thr Glu Gly Lys Phe Ser Phe Pro Ile Cys His Ala Ile Gly Glu Gly
305                 310                 315                 320

Ala Lys Asn Arg Thr Ala Leu Leu His Met Leu Arg Leu Lys Thr Asp
                325                 330                 335

Asp Met Lys Ile Lys Gln Glu Ala Val Cys Ile Leu Asp Asn Ala Gly
            340                 345                 350

Ser Leu Asp Tyr Thr Arg Glu Val Leu Tyr Gly Leu Asp Arg Lys Ala
        355                 360                 365

Arg Ser Leu Leu Arg Glu Phe Lys Thr Pro Asn Pro Phe Met Glu Ala
    370                 375                 380

Leu Leu Asp Ala Met Leu Ser Ser Leu Gln Ala Cys His
385                 390                 395

<210> SEQ ID NO 62
<211> LENGTH: 1310
<212> TYPE: DNA
<213> ORGANISM: Aspergillus nidulans

<400> SEQUENCE: 62

```
atgcctgaga gtcagatcat cgaactgggc acgctgggcc agatccccct ttacagcctt      60
gaacgcgcgc tccaggaccc tcttcgggct gtcaaactgc gacggcaaat cgtctcccag     120
catcaagcca ctggcaacat cgacttcaca acggacggct ccgcgctccc gtacgaagga     180
tacgactaca aagcagtcct cggagcctgc tgcgagaacg tgatcgggta tatgcccatc     240
cctgtgggcg tcgccggtcc gatcaaaatc aacggaaaga tggtgtttct ccccatgtcc     300
acgacagagg gcgcgctggt tgcgagcacg aatcgtggct gcatggcgat caacgccggt     360
ggaggcgtga ctgctctggt gctgggcgat ggcatgaccc gagcgcctat cgttcgattt     420
cccagtctcg aagaagccgg cgccgcaaaa caatggctgg gctctgatgc aggatttctc     480
atcattgagg acgcgttcaa tgcatccagc cgcttcgctc ggcttcaaaa cattaaggcc     540
acggccgttg gctcggacct ctatatccgg ttcacggcca gcgggcgca cgcaatgggc      600
atgaacatga tctccaaagg ggttgagcaa gcgctggagg cgatgcaaaa gcacgggttc     660
gagtctatgg atgtcgtctc gctgtcgggg aacttctgtg cggataaaaa acctgcggct     720
gtgaactgga ttgaggggcg aggcaagacc gtgaccgcgc aggcgacaat acctgaacat     780
gcggttcgag aaacactcaa gaccagtgtc gaggccctcg tggagctcaa cgtctccaag     840
aacctggtgg gcagtgctgt tgcagggggct ctgggagggt tcaacgccca tgccgccaat     900
gttgtcacgg cgatttatct tgccactggt caggatcccg cacagaatgt gcaaagcagc     960
aacactctga ccgtgatgaa aaagtgagta cactgcctct aaagatattc tgatagatgt    1020
tgcggcgcta actcccgagc agtgtgaatg gtgatttgca aatctctgtt ttcatgcctt    1080
ccattgaagt cggcaccgtt gggggaggga cagtcctggg ccctcaaaag gcaatgctgc    1140
acatgatggg cgtccaaggg gccgaccccg aacagccagg tagaaacgca caggagctgg    1200
ccctgctggt ggcggctggc gtgctggctg gagagctcag tctttgctct gctctgtcag    1260
cgggctcgtt ggtgaaaagc cacttgaccc ataatcggaa gaaaggatga              1310
```

<210> SEQ ID NO 63
<211> LENGTH: 416
<212> TYPE: PRT
<213> ORGANISM: Aspergillus nidulans

<400> SEQUENCE: 63

| | | | | | | | | | | | | | | |
|---|---|---|---|---|---|---|---|---|---|---|---|---|---|---|
| Met | Pro | Glu | Ser | Gln | Ile | Ile | Glu | Leu | Gly | Thr | Leu | Gly | Gln | Ile | Pro |
| 1 | | | | 5 | | | | | 10 | | | | | 15 | |
| Leu | Tyr | Ser | Leu | Glu | Arg | Ala | Leu | Gln | Asp | Pro | Leu | Arg | Ala | Val | Lys |
| | | | 20 | | | | | 25 | | | | | 30 | | |
| Leu | Arg | Arg | Gln | Ile | Val | Ser | Gln | His | Gln | Ala | Thr | Gly | Asn | Ile | Asp |
| | | 35 | | | | | 40 | | | | | 45 | | | |
| Phe | Thr | Thr | Asp | Gly | Ser | Ala | Leu | Pro | Tyr | Glu | Gly | Tyr | Asp | Tyr | Lys |
| | 50 | | | | | 55 | | | | | 60 | | | | |
| Ala | Val | Leu | Gly | Ala | Cys | Cys | Glu | Asn | Val | Ile | Gly | Tyr | Met | Pro | Ile |
| 65 | | | | | 70 | | | | | 75 | | | | | 80 |
| Pro | Val | Gly | Val | Ala | Gly | Pro | Ile | Lys | Ile | Asn | Gly | Lys | Met | Val | Phe |
| | | | | 85 | | | | | 90 | | | | | 95 | |
| Leu | Pro | Met | Ser | Thr | Thr | Glu | Gly | Ala | Leu | Val | Ala | Ser | Thr | Asn | Arg |
| | | | 100 | | | | | 105 | | | | | 110 | | |
| Gly | Cys | Met | Ala | Ile | Asn | Ala | Gly | Gly | Gly | Val | Thr | Ala | Leu | Val | Leu |
| | | 115 | | | | | 120 | | | | | 125 | | | |
| Gly | Asp | Gly | Met | Thr | Arg | Ala | Pro | Ile | Val | Arg | Phe | Pro | Ser | Leu | Glu |
| | 130 | | | | | 135 | | | | | 140 | | | | |

```
Glu Ala Gly Ala Ala Lys Gln Trp Leu Gly Ser Asp Ala Gly Phe Leu
145                 150                 155                 160

Ile Ile Glu Asp Ala Phe Asn Ala Ser Ser Arg Phe Ala Arg Leu Gln
            165                 170                 175

Asn Ile Lys Ala Thr Ala Val Gly Ser Asp Leu Tyr Ile Arg Phe Thr
        180                 185                 190

Ala Ser Thr Gly Asp Ala Met Gly Met Asn Met Ile Ser Lys Gly Val
    195                 200                 205

Glu Gln Ala Leu Glu Ala Met Gln Lys His Gly Phe Glu Ser Met Asp
210                 215                 220

Val Val Ser Leu Ser Gly Asn Phe Cys Ala Asp Lys Lys Pro Ala Ala
225                 230                 235                 240

Val Asn Trp Ile Glu Gly Arg Gly Lys Thr Val Thr Ala Gln Ala Thr
            245                 250                 255

Ile Pro Glu His Ala Val Arg Glu Thr Leu Lys Thr Ser Val Glu Ala
            260                 265                 270

Leu Val Glu Leu Asn Val Ser Lys Asn Leu Val Gly Ser Ala Val Ala
        275                 280                 285

Gly Ala Leu Gly Gly Phe Asn Ala His Ala Ala Asn Val Val Thr Ala
    290                 295                 300

Ile Tyr Leu Ala Thr Gly Gln Asp Pro Ala Gln Asn Val Gln Ser Ser
305                 310                 315                 320

Asn Thr Leu Thr Val Met Lys Asn Val Asn Gly Asp Leu Gln Ile Ser
            325                 330                 335

Val Phe Met Pro Ser Ile Glu Val Gly Thr Val Gly Gly Gly Thr Val
            340                 345                 350

Leu Gly Pro Gln Lys Ala Met Leu His Met Met Gly Val Gln Gly Ala
        355                 360                 365

Asp Pro Glu Gln Pro Gly Arg Asn Ala Gln Glu Leu Ala Leu Leu Val
    370                 375                 380

Ala Ala Gly Val Leu Ala Gly Glu Leu Ser Leu Cys Ser Ala Leu Ser
385                 390                 395                 400

Ala Gly Ser Leu Val Lys Ser His Leu Thr His Asn Arg Lys Lys Gly
            405                 410                 415

<210> SEQ ID NO 64
<211> LENGTH: 3056
<212> TYPE: DNA
<213> ORGANISM: Aspergillus nidulans

<400> SEQUENCE: 64
tcatgtagag ttactccatt gtgcaggtaa ttcaagcata aaacaatcat gtgcgagatc      60
acatccgact cgcaatatct ctaaagcgta aatctgcccg tacacatcag tcacgtcgca     120
aaacatctgc accttctcca gcatcctcat cttggcccta tcctgcgccg ccatctctgt     180
caagacctcc aagccccgct tcatgttgga ccgctcaaac tcagcgagag agaacagctg     240
cttctgccga accgcatctg attttggccc ggcctgggca aactcgggaa agttgacgca     300
gttgagattc ttctcgtcgc ggtcacgggc aagcgatccg taatcgttgt acatgcggca     360
catcacggcg agatggcggc acattgcttc agccacatac ttctcttcgc aggtctgaaa     420
gcacgcggcg ttgtgggacg cctgctcgaa cccagcagg cactggtaga aggcaaacga     480
gtaggggcag gaggtgtggt cggacgaggt ggaagacacc cagcggtaga agctggagcg     540
ggcggtctcg aagtcgtcgc gggtggactc cagttgggcg gcgaagcggc cgttgtcgtc     600
```

-continued

```
ggcctgctct atgtgcgaca gcaggaagac ctgaagctcg ttcttgacgc gctcgtactc    660
gaggggcgcg gcggccttca cgctgggatg gtccatgacg tggtggacga aggcgctaag    720
gacgcggctc acgtcgcttg ggagttgtga ccccatcttg atgcgtttgg cttgcggtag    780
gatcctgtga ccgtttgcgt ctgcgtttct tggaccagac tgggcctgga ttgcgtcatt    840
cagctccggt ttgtccttga ggtcgcggaa gatctcgtcg atgcaggacc gggtcatgga    900
tctctggctg ctgttcagtc tgccgactac cgcttccata aattcatcgg cttggtagtt    960
gaggaacgaa atcaccatca tctcgacaag ggttttcgtg gagaggaagg tgttcctgcg   1020
gttattgcac agggtccagg tgaacggaat gtactcaaaa tacttgtctt cttccatgcc   1080
cgtgcgagag aagacggcaa gacgtcggtc gcgcagctgt ggcaggagca ggtatccttc   1140
gacgatggca gcgcggacct tccagagttc catgctcgaa acagggggaa gcatggagtg   1200
gaagcgtgcg aactcgatga cacgcttctt gctgacgatg aacagattcg ccagacaggc   1260
tggataagaa cgttcgaagg acaccttcag cgcggcgagg acatagctct tactgaggag   1320
aattgagctg tatgtcacct tctctaccca cagatactcc gctttgtcgc ctgcgctgtt   1380
ttgcaggaac ttgcggcctc gagacacagc cagctgcaca ttcgtccaca gctgattcac   1440
cacgggcaac tggcatgcgt gagcgatggt cagaatagca tatgccgtct cttcgtggga   1500
gtgcgatccc caggatccgt tctcgttctg agtctgtagt gtgcgaacca atgcctgata   1560
caggcagacc gatactcgat ctctgataaa ctgactggaa atcgacttga gtccgccatc   1620
tgaccatacc tgcagcagct tcccaaacgc ctcagccatg agcatggatg gatagtacgg   1680
ggagaggttc tgagagagtc agcgctctgc tatttccatt tctgttgcga aagaagtga   1740
tacccatttta tccccaatct cactgtcggc cgtccaccag acatcacaca gaaaggccgc   1800
tgcttttttcg atctggggcg acacagtggc cgcatcgggc gtattcaaca gcgcaagcaa   1860
tacattgctg tttgcagtga agctgggatc tctctcgccg tgataggtgc ggaagtgcat   1920
cgggccctcg aatgcatcta ttagtccctg ggccgagact ggtttgtcca acaaggagac   1980
cgcaataagc gatttggcgg tatcgtcggc gtctgcctgg atcgacggag ctatacaaca   2040
gaatggttag ctacgtgagg gagagtgata gagccatgtt gtgggatcgt accaaatcct   2100
acaatacctc ctcctttgac caacgcatcg cgaagcatct cgccgaggct gtcggtgtct   2160
tcgataccga gatcgcctgt agaatatcca ttgtccaaga gcgtggtaag ggcctgaagt   2220
tcagtcagct ttgattctag tcgagcaagc tgtcccctta cccacgagac ctcgaaatac   2280
tttgaaggat acgcgctcgg cattcctcca gtgcccctc cggcgccatt ctgtagcacc   2340
aaccgcaagt actgttcgca ctcgtcgtcc caggaggagg aaaacatgag aaaggcggcc   2400
gtggacgatg cgagaacat gaaagagcca ttgaccttct ggtgcgccac tttatcaaag   2460
tcgatcatgc ccacaaacgc ctcaagcgag tgcagcgcgg tggttctggc ggagtacagg   2520
tactccggcc tgaacttgga gagcttgatg cgattcagcc ggtcgagctc ggcgcgcccg   2580
tcaaattcaa actcgtgccc tttctcgcgc aggagccgca gaagcgcggg caaaatgatt   2640
tcaaagccaa cgtgaacagt gtcttttaca ctccacgctt gcagttgtcg tgagagggcc   2700
gcgcgtgccc gtccgattcg ctccttcatt tcttccacgg gagggtcggt gctggcaatc   2760
cggctttctg catgggtctc gagggccagt aaggaggctg cggtgttgag gataccgtcg   2820
acgtcggagg cgtaggtctc ccaactgcca tcctctagct gggtccgcag gatgtattcg   2880
aagcattttg gcaggagcca ttgacgccct tctggtgtcg tcttctggac catggacacc   2940
```

```
caggccgtgt cgtagactgc cgcggacata aagcccagct ctccatcttt tgtccggagc    3000
tgttggacca gctgggaggc ttgcgtgcat agatctgtca cgtctgcgca agtcat        3056
```

<210> SEQ ID NO 65
<211> LENGTH: 979
<212> TYPE: PRT
<213> ORGANISM: Aspergillus nidulans

<400> SEQUENCE: 65

```
Met Thr Cys Ala Asp Val Thr Asp Leu Cys Thr Gln Ala Ser Gln Leu
1               5                   10                  15

Val Gln Gln Leu Arg Thr Lys Asp Gly Glu Leu Gly Phe Met Ser Ala
            20                  25                  30

Ala Val Tyr Asp Thr Ala Trp Val Ser Met Val Gln Lys Thr Thr Pro
        35                  40                  45

Glu Gly Arg Gln Trp Leu Leu Pro Lys Cys Phe Glu Tyr Ile Leu Arg
    50                  55                  60

Thr Gln Leu Glu Asp Gly Ser Trp Glu Thr Tyr Ala Ser Asp Val Asp
65                  70                  75                  80

Gly Ile Leu Asn Thr Ala Ala Ser Leu Leu Ala Leu Glu Thr His Ala
                85                  90                  95

Glu Ser Arg Ile Ala Ser Thr Asp Pro Pro Val Glu Glu Met Lys Glu
            100                 105                 110

Arg Ile Gly Arg Ala Arg Ala Ala Leu Ser Arg Gln Leu Gln Ala Trp
        115                 120                 125

Ser Val Lys Asp Thr Val His Val Gly Phe Glu Ile Ile Leu Pro Ala
    130                 135                 140

Leu Leu Arg Leu Leu Arg Glu Lys Gly His Glu Phe Glu Phe Asp Gly
145                 150                 155                 160

Arg Ala Glu Leu Asp Arg Leu Asn Arg Ile Lys Leu Ser Lys Phe Arg
                165                 170                 175

Pro Glu Tyr Leu Tyr Ser Ala Arg Thr Thr Ala Leu His Ser Leu Glu
            180                 185                 190

Ala Phe Val Gly Met Ile Asp Phe Asp Lys Val Ala His Gln Lys Val
        195                 200                 205

Asn Gly Ser Phe Met Phe Ser Pro Ser Ser Thr Ala Ala Phe Leu Met
    210                 215                 220

Phe Ser Ser Ser Trp Asp Asp Glu Cys Glu Gln Tyr Leu Arg Leu Val
225                 230                 235                 240

Leu Gln Asn Gly Ala Gly Gly Thr Gly Gly Met Pro Ser Ala Tyr
                245                 250                 255

Pro Ser Lys Tyr Phe Glu Val Ser Trp Val Arg Gly Gln Leu Ala Arg
            260                 265                 270

Leu Glu Ser Lys Leu Thr Glu Leu Gln Ala Leu Thr Thr Leu Leu Asp
        275                 280                 285

Asn Gly Tyr Ser Thr Gly Asp Leu Gly Ile Glu Asp Thr Asp Ser Leu
    290                 295                 300

Gly Glu Met Leu Arg Asp Ala Leu Val Lys Gly Gly Ile Val Gly
305                 310                 315                 320

Phe Ala Pro Ser Ile Gln Ala Asp Ala Asp Thr Ala Lys Ser Leu
                325                 330                 335

Ile Ala Val Ser Leu Leu Asp Lys Pro Val Ser Ala Gln Gly Leu Ile
            340                 345                 350

Asp Ala Phe Glu Gly Pro Met His Phe Arg Thr Tyr His Gly Glu Arg
```

-continued

```
                355                 360                 365
Asp Pro Ser Phe Thr Ala Asn Ser Asn Val Leu Leu Ala Leu Leu Asn
370                 375                 380

Thr Pro Asp Ala Ala Thr Val Ser Pro Gln Ile Glu Lys Ala Ala Ala
385                 390                 395                 400

Phe Leu Cys Asp Val Trp Trp Thr Ala Asp Ser Glu Ile Gly Asp Lys
                405                 410                 415

Trp Asn Leu Ser Pro Tyr Tyr Pro Ser Met Leu Met Ala Glu Ala Phe
                420                 425                 430

Gly Lys Leu Leu Gln Val Trp Ser Asp Gly Leu Lys Ser Ile Ser
                435                 440                 445

Ser Gln Phe Ile Arg Asp Arg Val Ser Val Cys Leu Tyr Gln Ala Leu
            450                 455                 460

Val Arg Thr Leu Gln Thr Gln Asn Glu Asn Gly Ser Trp Gly Ser His
465                 470                 475                 480

Ser His Glu Glu Thr Ala Tyr Ala Ile Leu Thr Ile Ala His Ala Cys
                485                 490                 495

Gln Leu Pro Val Val Asn Gln Leu Trp Thr Asn Val Gln Leu Ala Val
                500                 505                 510

Ser Arg Gly Arg Lys Phe Leu Gln Asn Ser Ala Gly Asp Lys Ala Glu
            515                 520                 525

Tyr Leu Trp Val Glu Lys Val Thr Tyr Ser Ser Ile Leu Leu Ser Lys
530                 535                 540

Ser Tyr Val Leu Ala Ala Leu Lys Val Ser Phe Glu Arg Ser Tyr Pro
545                 550                 555                 560

Ala Cys Leu Ala Asn Leu Phe Ile Val Ser Lys Lys Arg Val Ile Glu
                565                 570                 575

Phe Ala Arg Phe His Ser Met Leu Pro Leu Phe Ser Ser Met Glu Leu
                580                 585                 590

Trp Lys Val Arg Ala Ala Ile Val Glu Gly Tyr Leu Leu Pro Gln
            595                 600                 605

Leu Arg Asp Arg Arg Leu Ala Val Phe Ser Arg Thr Gly Met Glu Glu
610                 615                 620

Asp Lys Tyr Phe Glu Tyr Ile Pro Phe Thr Trp Thr Leu Cys Asn Asn
625                 630                 635                 640

Arg Arg Asn Thr Phe Leu Ser Thr Lys Thr Leu Val Glu Met Met Val
                645                 650                 655

Ile Ser Phe Leu Asn Tyr Gln Ala Asp Glu Phe Met Glu Ala Val Val
                660                 665                 670

Gly Arg Leu Asn Ser Ser Gln Arg Ser Met Thr Arg Ser Cys Ile Asp
            675                 680                 685

Glu Ile Phe Arg Asp Leu Lys Asp Lys Pro Glu Leu Asn Asp Ala Ile
690                 695                 700

Gln Ala Gln Ser Gly Pro Arg Asn Ala Asp Ala Asn Gly His Arg Ile
705                 710                 715                 720

Leu Pro Gln Ala Lys Arg Ile Lys Met Gly Ser Gln Leu Pro Ser Asp
                725                 730                 735

Val Ser Arg Val Leu Ser Ala Phe Val His Val Met Asp His Pro
                740                 745                 750

Ser Val Lys Ala Ala Ala Pro Leu Glu Tyr Glu Arg Val Lys Asn Glu
            755                 760                 765

Leu Gln Val Phe Leu Leu Ser His Ile Glu Gln Ala Asp Asp Asn Gly
770                 775                 780
```

```
Arg Phe Ala Ala Gln Leu Glu Ser Thr Arg Asp Asp Phe Glu Thr Ala
785                 790                 795                 800

Arg Ser Ser Phe Tyr Arg Trp Val Ser Thr Ser Ser Asp His Thr
            805                 810                 815

Ser Cys Pro Tyr Ser Phe Ala Phe Tyr Gln Cys Leu Leu Gly Phe Glu
            820                 825                 830

Gln Ala Ser His Asn Ala Ala Cys Phe Gln Thr Cys Glu Glu Lys Tyr
            835                 840                 845

Val Ala Glu Ala Met Cys Arg His Leu Ala Val Met Cys Arg Met Tyr
850                 855                 860

Asn Asp Tyr Gly Ser Leu Ala Arg Asp Arg Asp Glu Lys Asn Leu Asn
865                 870                 875                 880

Cys Val Asn Phe Pro Glu Phe Ala Gln Ala Gly Pro Lys Ser Asp Ala
            885                 890                 895

Val Arg Gln Lys Gln Leu Phe Ser Leu Ala Glu Phe Glu Arg Ser Asn
            900                 905                 910

Met Lys Arg Gly Leu Glu Val Leu Thr Glu Met Ala Ala Gln Asp Arg
            915                 920                 925

Ala Lys Met Arg Met Leu Glu Lys Val Gln Met Phe Cys Asp Val Thr
            930                 935                 940

Asp Val Tyr Gly Gln Ile Tyr Ala Leu Glu Ile Leu Arg Val Gly Cys
945                 950                 955                 960

Asp Leu Ala His Asp Cys Phe Met Leu Glu Leu Pro Ala Gln Trp Ser
                965                 970                 975

Asn Ser Thr

<210> SEQ ID NO 66
<211> LENGTH: 996
<212> TYPE: DNA
<213> ORGANISM: Aspergillus nidulans

<400> SEQUENCE: 66
atgaagtact tgaatatttc cttgtcccgt gatatagcat ctgaacattt taatttctta    60
gtactctcaa tgcaccccgg aatcccacgc gtcacccagc tatgaccgcg gatacgcttg   120
tcgacgcacc ggctctgccg catcagaatg gcagtacaga agagaaactg aaggagcgcg   180
gaagctttgg aaagctctac acgtacaagg tcagcaccgt tttcatgtta tccctatgag   240
tcggaaagcc cagcatatgg tcgcagggct aactggcaac agcggagccc ccgagcccta   300
ggcatccaag ctgtcgcaaa atccatcggc ttggagctgg agcaagtcga gctgcagccg   360
gccaacggcg tcccagactt ctactggaac ctgaacccgc tgggcaagac cccgacgttt   420
gtcggcgcag acggcctggt gctgacggag tgtatgcgca ttgccctgca cggtgcgttc   480
ccccctcgac ttacgatgat acgcttgctt ttgtgctgaa taacactcac aagagcagtg   540
accaacgaag actcgacgac cacgctcctg ggcagcagct cgctcgactt cgtccagatc   600
atccgctgga tctcgttcac caacacggat gtcgtcaccc gcatggcgtc ctgggtccgg   660
ccgttgatcg gctacacgcc gtacagcaag gaggaggtgc tcaaggcgca gcagcagacg   720
acgcaggcca tcggcgtctt cgaggacagc ttgcgcgacc gcaagtatct cgtgggcgac   780
cgcctgacgc tggctgatat catgtgtgtc agcttggtgt cgtttgggtt cgcgcagatc   840
ttcgataagg agtggaggga ggccttttca tactttttcgg gctggtacat gatggttatg   900
catttaccca tcatgaaggc agtggtggag gaggtgccgt tgtcgaggg gggcttgccg   960
```
aatgcaccgc ccacggagcc gttcagggcg ccttag         996

<210> SEQ ID NO 67
<211> LENGTH: 266
<212> TYPE: PRT
<213> ORGANISM: Aspergillus nidulans

<400> SEQUENCE: 67

Met Asn Thr Leu Asn Ala Pro Arg Asn Pro Thr Arg His Pro Ala Met
1               5                   10                  15

Thr Ala Asp Thr Leu Val Asp Ala Pro Ala Leu Pro His Gln Asn Gly
            20                  25                  30

Ser Thr Glu Glu Lys Leu Lys Glu Arg Gly Ser Phe Gly Lys Leu Tyr
        35                  40                  45

Thr Tyr Lys Arg Ser Pro Arg Ala Leu Gly Ile Gln Ala Val Ala Lys
50                  55                  60

Ser Ile Gly Leu Glu Leu Glu Gln Val Glu Leu Gln Pro Ala Asn Gly
65                  70                  75                  80

Val Pro Asp Phe Tyr Trp Asn Leu Asn Pro Leu Gly Lys Thr Pro Thr
                85                  90                  95

Phe Val Gly Ala Asp Gly Leu Val Leu Thr Glu Cys Met Ala Ile Ala
            100                 105                 110

Leu His Val Thr Asn Glu Asp Ser Thr Thr Thr Leu Leu Gly Ser Ser
        115                 120                 125

Ser Leu Asp Phe Val Gln Ile Ile Arg Trp Ile Ser Phe Thr Asn Thr
130                 135                 140

Asp Val Val Thr Arg Met Ala Ser Trp Val Arg Pro Leu Ile Gly Tyr
145                 150                 155                 160

Thr Pro Tyr Ser Lys Glu Glu Val Leu Lys Ala Gln Gln Gln Thr Thr
                165                 170                 175

Gln Ala Ile Gly Val Phe Glu Asp Ser Leu Arg Asp Arg Lys Tyr Leu
            180                 185                 190

Val Gly Asp Arg Leu Thr Leu Ala Asp Ile Met Cys Val Ser Leu Val
        195                 200                 205

Ser Phe Gly Phe Ala Gln Ile Phe Asp Lys Glu Trp Arg Glu Ala Phe
210                 215                 220

Pro Tyr Phe Ser Gly Trp Tyr Met Met Val Met His Leu Pro Ile Met
225                 230                 235                 240

Lys Ala Val Val Glu Glu Val Pro Phe Val Glu Glu Gly Leu Pro Asn
                245                 250                 255

Ala Pro Pro Thr Glu Pro Phe Arg Ala Pro
            260                 265

<210> SEQ ID NO 68
<211> LENGTH: 1056
<212> TYPE: DNA
<213> ORGANISM: Aspergillus nidulans

<400> SEQUENCE: 68
ctatcgatga actgcctggt ccataaggct ctcagtatga tcccaaacca actgaggtat      60
cttctgctcc cgatactgcg ccagaatctt ggtgctcggc ctaacatccc ccttccaatt     120
caacaggtag gcgccactcc ccggttcccc agtaatgcct ttagcgacct cgccagcctc     180
cagcggaaca ccctggggca caatgccctg ctttgctggg tagtgtgccg agctcagatg     240
gaaaagatgt cgctcgccac tctcgccgag atccacggaa aacggcttca tgaacggcca     300

```
cacgaggtaa ttgtagaagg tcgaaaccgg agctgggaag ctgttggtgt agatgttggt    360
gccaacgaga cccgggtaga cgtgaatgaa actgacggcc gggtgggtgc gggcgaggtg    420
ctccatgctc agggaggtca tggtgatgga gtgcttgtag gcgttgagca gggagaagtt    480
gtgcttgagg tcgaggtcgg ccgtgtttat ggagtactcg aagccgccgc cgtagacgct    540
aatcacgcgg cttgggctcg acgcctccag cagcgggagg aggttctgaa taaagcgcat    600
ccgggagtag tagcggagag cgaagaggta gtcgatgcct tcgacggttt ctgtatcttt    660
ttgttagcgc aaggtactcc gtggacgggt ctccgtctgc ataccgtttc ggcccctag     720 agaaatcccg cccggggtca tgaagagaaa gttcagcttc ttctgctgct ggagaatctg    780
ctggcacgcg gcgtccacat tccgtacgag cgacacatcc gcctcgatga agtggaagcg    840
gcccttgggg ttcaattgct gcagttccga caagaacggc cgggtgcgag cctcgttgcg    900
accgatgata taggccgtcg ggctgtcggc gtaacgggcc agctggcgca gggtgctctg    960
gccgatgcca ctggtgccgc caacaaacaa ggccgtaatg ttggggagcg cccgaaggcc   1020
ggcgttagat gcttgcaccg tcttcagaga gaccat                             1056
```

<210> SEQ ID NO 69
<211> LENGTH: 333
<212> TYPE: PRT
<213> ORGANISM: Aspergillus nidulans

<400> SEQUENCE: 69

```
Met Val Ser Leu Lys Thr Val Gln Ala Ser Asn Ala Gly Leu Arg Ala
1               5                   10                  15

Leu Pro Asn Ile Thr Ala Leu Phe Val Gly Gly Thr Ser Gly Ile Gly
            20                  25                  30

Gln Ser Thr Leu Arg Gln Leu Ala Arg Tyr Ala Asp Ser Pro Thr Ala
        35                  40                  45

Tyr Ile Ile Gly Arg Asn Glu Ala Arg Thr Arg Pro Phe Leu Ser Glu
    50                  55                  60

Leu Gln Gln Leu Asn Pro Lys Gly Arg Phe His Phe Ile Glu Ala Asp
65                  70                  75                  80

Val Ser Leu Val Arg Asn Val Asp Ala Ala Cys Gln Gln Ile Leu Gln
                85                  90                  95

Gln Gln Lys Lys Leu Asn Phe Leu Phe Met Thr Pro Gly Gly Ile Ser
            100                 105                 110

Leu Gly Gly Arg Asn Glu Thr Val Glu Gly Ile Asp Tyr Leu Phe Ala
        115                 120                 125

Leu Arg Tyr Tyr Ser Arg Met Arg Phe Ile Gln Asn Leu Leu Pro Leu
    130                 135                 140

Leu Glu Ala Ser Ser Pro Ser Arg Val Ile Ser Val Tyr Gly Gly Gly
145                 150                 155                 160

Phe Glu Tyr Ser Ile Asn Thr Ala Asp Leu Asp Leu Lys His Asn Phe
                165                 170                 175

Ser Leu Leu Asn Ala Tyr Lys His Ser Ile Thr Met Thr Ser Leu Ser
            180                 185                 190

Met Glu His Leu Ala Arg Thr His Pro Ala Val Ser Phe Ile His Val
        195                 200                 205

Tyr Pro Gly Leu Val Gly Thr Asn Ile Tyr Thr Asn Ser Phe Pro Ala
    210                 215                 220

Pro Val Ser Thr Phe Tyr Asn Tyr Leu Val Trp Pro Phe Met Lys Pro
225                 230                 235                 240
```

```
Phe Ser Val Asp Leu Gly Glu Ser Gly Glu Arg His Leu Phe His Leu
                245                 250                 255

Ser Ser Ala His Tyr Pro Ala Lys Gln Gly Ile Val Pro Gln Gly Val
            260                 265                 270

Pro Leu Glu Ala Gly Glu Val Ala Lys Gly Ile Thr Gly Glu Pro Gly
        275                 280                 285

Ser Gly Ala Tyr Leu Leu Asn Trp Lys Gly Asp Val Arg Pro Ser Thr
    290                 295                 300

Lys Ile Leu Ala Gln Tyr Arg Glu Gln Lys Ile Pro Gln Leu Val Trp
305                 310                 315                 320

Asp His Thr Glu Ser Leu Met Asp Gln Ala Val His Arg
                325                 330

<210> SEQ ID NO 70
<211> LENGTH: 1036
<212> TYPE: DNA
<213> ORGANISM: Aspergillus nidulans

<400> SEQUENCE: 70
atggttgatg caacgtctcc ccccggcgtc aacgcagtgg tgaattacta cgtgcccaac     60
agcgatgggt ctccgcctgc caccaacgac atggccgtca tgctgggcca aaaggacatg    120
atttcccaca aaatgcgaat ccgcgatctg cgcccttaca aggaggagta ttcgctggat    180
cgcaacggct tccagtacgc gacgatccac tccacgctta cggatgccac cgacgagacc    240
cagatcaaag aggtctacta ccgagagatt gagaaactgg tccaagatat gtgcgtgtgc    300
tcgttcgcct ccatgacgcg ctagtctaat ctgcatgaat actgcagcac cggggccaag    360
cgggtgcttg ccttccacca tgcagtgcgc acccgcaccg caacgagtt cggcgagcag    420 atcaaagacc gctaccaggg cgtcgagggg cccgcgtatc gcgtacacat tgaccagacc    480
ccccagggcg cgctcagcat cgtgcagttt atgtttcccg atctcgcgga cgatgtccgc    540
aacggcagtt tccaggtgat caacgttttgg cgcccgttga cgcgggtgca gcgtgacccc    600
ctgatggtgg ctgatgcggc cgagatgccg cccgaggacc tgcttctaat cagccggaag    660
tattacaacg gctgcattc gtccaacttt gtcattaagt atgatggtcg aatggcggct    720
ggggagggcc cgacggatgg gctgagcggt gatggaaagc atagctggtg gtatatcggg    780
gaccaggagc ccaccgaagc gttggttttc tcctcatctg gcttccgcaa tggaaaggcg    840
atcatcggca cggcacatgg tgcgttctgt ttgcctgatc aagatcagta cccagctcgt    900
cagagcattg agtgtcggtg tgttgctatc tattgataaa tcatgtctag acctttactc    960
ggcagaacca atgataaatg catatgaacg caagaatgct agctcattat atggccatga   1020
tgagtcccag atatag                                                   1036

<210> SEQ ID NO 71
<211> LENGTH: 295
<212> TYPE: PRT
<213> ORGANISM: Aspergillus nidulans

<400> SEQUENCE: 71

Met Val Asp Ala Thr Ser Pro Pro Gly Val Asn Ala Val Val Asn Tyr
1               5                  10                  15

Tyr Val Pro Asn Ser Asp Gly Ser Pro Pro Ala Thr Asn Asp Met Ala
            20                  25                  30

Val Met Leu Gly Gln Lys Asp Met Ile Ser His Lys Met Arg Ile Arg
        35                  40                  45
```

```
Asp Leu Arg Pro Tyr Lys Glu Glu Tyr Ser Leu Asp Arg Asn Gly Phe
 50                  55                  60

Gln Tyr Ala Thr Ile His Ser Thr Leu Thr Asp Ala Thr Asp Glu Thr
 65                  70                  75                  80

Gln Ile Lys Glu Val Tyr Tyr Arg Glu Ile Glu Lys Leu Val Gln Asp
                 85                  90                  95

Ile Thr Gly Ala Lys Arg Val Leu Ala Phe His His Ala Val Arg Thr
                100                 105                 110

Arg Thr Gly Asn Glu Phe Gly Glu Gln Ile Lys Asp Arg Tyr Gln Gly
            115                 120                 125

Val Glu Gly Pro Ala Tyr Arg Val His Ile Asp Gln Thr Pro Gln Gly
130                 135                 140

Ala Leu Ser Ile Val Gln Phe Met Phe Pro Asp Leu Ala Asp Asp Val
145                 150                 155                 160

Arg Asn Gly Ser Phe Gln Val Ile Asn Val Trp Arg Pro Leu Thr Arg
                165                 170                 175

Val Gln Arg Asp Pro Leu Met Val Ala Asp Ala Ala Glu Met Pro Pro
            180                 185                 190

Glu Asp Leu Leu Leu Ile Ser Arg Lys Tyr Tyr Asn Gly Leu His Ser
        195                 200                 205

Ser Asn Phe Val Ile Lys Tyr Asp Gly Arg Met Ala Ala Gly Glu Gly
210                 215                 220

Pro Thr Asp Gly Leu Ser Gly Asp Gly Lys His Ser Trp Trp Tyr Ile
225                 230                 235                 240

Gly Asp Gln Glu Pro Thr Glu Ala Leu Val Phe Ser Ser Ser Gly Phe
                245                 250                 255

Arg Asn Gly Lys Ala Ile Ile Gly Thr Ala His Asp Leu Tyr Ser Ala
            260                 265                 270

Glu Pro Met Ile Asn Ala Tyr Glu Arg Lys Asn Ala Ser Ser Leu Tyr
        275                 280                 285

Gly His Asp Glu Ser Gln Ile
    290                 295

<210> SEQ ID NO 72
<211> LENGTH: 1706
<212> TYPE: DNA
<213> ORGANISM: Aspergillus nidulans

<400> SEQUENCE: 72
atggacaact ataccggca ctctgggacc ctcatccctt ccgattcacc atcatccatt      60
gatcgctcgc agctctatct ggagatcctc ggcgttctta gcgtggtcta cctgctccaa     120
accctggtcg catattccaa atccttcaag gccccttttcg tgggcttccg attctgtat    180 gagccgaaat ggttggtagg actacgtttc tcccagggcg ctctggcgca ggtcaatgaa    240
ggatacgcca agtacgcaa tgctaccgtt cccccaggac tctgtctaat gcgcttgaca    300
gtacaagaac gccatgttca aggtcgcccg caacgactca gacatcctgg ttatccccaa    360
caagtatgtc gaggaactgc gatccctgcc tgacgagaag atcagcgcca tccgcgcgca    420
tatcaagaat ctcctgggaa agtactcgac cacgctgatc ctcctggaga gcgacctgca    480
tacgcgcatg ctgcagacca agctgacccc taatctcggc tccttcatcg aggtcatcga    540
gtcggagctc ctcttcgcca tggaccagga gatccccgcg aacctagacg actggcagag    600
cgtcaatgtg ttccacatcg ttcttcgcat cgtggcgcgc atctccgcac gcgtgttctt    660
gggcgtcccc gcctgccgca atgaggaatg gctccagacc tctattcact acaccgagaa    720
```

-continued

```
cgtctttgcg accgtcatgc tgttgcggcg cttccccaag tggatgcacc cgattgtggg     780
acacctcctc cccagctact gggcaatcca caggaacctg cggaccgcga agcgcatcat     840
cagtcccatg gtgcgccagc gccgcgcaga agaggccaag cggaacccgg actatgtaaa     900
gcccaacgat ctcctccagt ggatgatgga cggcgcaaac gagaacgacg ggcagcccga     960
caagctggcg caccgccagc tcctcctaag cctggcttcc atccacacaa caaccatggc    1020
ggcggcgcac tgcttctacg atctctgcca acatcccgag tactttgagc cgttgcgcga    1080
ggagatcaac gacgtaattg cccaggatgg cggctggaaa aagaccactc tcaacaagat    1140
gcgcaagctg gacagctttc ttaaagaaag ccaacgcatc aacccgccca gtctctgtag    1200
gtactccttg tcatatccga taaacaattc cgctaacgct ttctccagtg cattcaacc     1260
gcattgtctc ggaagacctg acgctctcgg acggcaccct cctgcccaaa ggaacgcatt    1320
tcagcatgcc ctccgcggcc atcctccagg acaacggcgt ggaacccggt gccgaccaat    1380
tcgatgggtt ccgatactac aagaagcgcc tcaaccccga ggaagccaac aagcaccagt    1440
tcgccatgac cgacaacaac aacctccatt ttggccacgg caagtactca tgtcccggcc    1500
gcttcttcgc ctccaacgag atcaagatca tcatggcgca cctgttgacc gactacgaat    1560
tcaaataccc ccggggcgcg acaaggccgc ggaatctgac ggccgatgag aacctgtatc    1620
cagatccgtc ggcacgtctg ctcatgagac gacgggtggt ggctccgccg caggcgtcga    1680
tcacgccgca gcttgtctca gcctag                                          1706
```

<210> SEQ ID NO 73
<211> LENGTH: 534
<212> TYPE: PRT
<213> ORGANISM: Aspergillus nidulans

<400> SEQUENCE: 73

```
Met Asp Asn Tyr Thr Trp His Ser Gly Thr Leu Ile Pro Ser Asp Ser
1               5                   10                  15

Pro Ser Ser Ile Asp Arg Ser Gln Leu Tyr Leu Glu Ile Leu Gly Val
            20                  25                  30

Leu Ser Val Val Tyr Leu Leu Gln Thr Leu Val Ala Tyr Ser Lys Ser
        35                  40                  45

Phe Lys Ala Pro Phe Val Gly Phe Arg Phe Trp Tyr Glu Pro Lys Trp
    50                  55                  60

Leu Val Gly Leu Arg Phe Ser Gln Gly Ala Leu Ala Gln Val Asn Glu
65                  70                  75                  80

Gly Tyr Ala Lys Tyr Lys Asn Ala Met Phe Lys Val Ala Arg Asn Asp
                85                  90                  95

Ser Asp Ile Leu Val Ile Pro Asn Lys Tyr Val Glu Glu Leu Arg Ser
            100                 105                 110

Leu Pro Asp Glu Lys Ile Ser Ala Ile Arg Ala His Ile Lys Asn Leu
        115                 120                 125

Leu Gly Lys Tyr Ser Thr Thr Leu Ile Leu Leu Glu Ser Asp Leu His
    130                 135                 140

Thr Arg Met Leu Gln Thr Lys Leu Thr Pro Asn Leu Gly Ser Phe Ile
145                 150                 155                 160

Glu Val Ile Glu Ser Glu Leu Leu Phe Ala Met Asp Gln Glu Ile Pro
                165                 170                 175

Ala Asn Leu Asp Asp Trp Gln Ser Val Asn Val Phe His Ile Val Leu
            180                 185                 190
```

```
Arg Ile Val Ala Arg Ile Ser Ala Arg Val Phe Leu Gly Val Pro Ala
            195                 200                 205
Cys Arg Asn Glu Glu Trp Leu Gln Thr Ser Ile His Tyr Thr Glu Asn
210                 215                 220
Val Phe Ala Thr Val Met Leu Leu Arg Arg Phe Pro Lys Trp Met His
225                 230                 235                 240
Pro Ile Val Gly His Leu Leu Pro Ser Tyr Trp Ala Ile His Arg Asn
                    245                 250                 255
Leu Arg Thr Ala Lys Arg Ile Ile Ser Pro Met Val Arg Gln Arg Arg
                260                 265                 270
Ala Glu Glu Ala Lys Arg Asn Pro Asp Tyr Val Lys Pro Asn Asp Leu
            275                 280                 285
Leu Gln Trp Met Met Asp Gly Ala Asn Glu Asn Asp Gly Gln Pro Asp
        290                 295                 300
Lys Leu Ala His Arg Gln Leu Leu Ser Leu Ala Ser Ile His Thr
305                 310                 315                 320
Thr Thr Met Ala Ala His Cys Phe Tyr Asp Leu Cys Gln His Pro
                325                 330                 335
Glu Tyr Phe Glu Pro Leu Arg Glu Ile Asn Asp Val Ile Ala Gln
                340                 345                 350
Asp Gly Gly Trp Lys Lys Thr Thr Leu Asn Lys Met Arg Lys Leu Asp
            355                 360                 365
Ser Phe Leu Lys Glu Ser Gln Arg Ile Asn Pro Ser Leu Leu Ala
        370                 375                 380
Phe Asn Arg Ile Val Ser Glu Asp Leu Thr Leu Ser Asp Gly Thr Leu
385                 390                 395                 400
Leu Pro Lys Gly Thr His Phe Ser Met Pro Ser Ala Ala Ile Leu Gln
                405                 410                 415
Asp Asn Gly Val Glu Pro Gly Ala Asp Gln Phe Asp Gly Phe Arg Tyr
                420                 425                 430
Tyr Lys Lys Arg Leu Asn Pro Glu Glu Ala Asn Lys His Gln Phe Ala
            435                 440                 445
Met Thr Asp Asn Asn Leu His Phe Gly His Gly Lys Tyr Ser Cys
450                 455                 460
Pro Gly Arg Phe Phe Ala Ser Asn Glu Ile Lys Ile Met Ala His
465                 470                 475                 480
Leu Leu Thr Asp Tyr Glu Phe Lys Tyr Pro Arg Gly Ala Thr Arg Pro
                485                 490                 495
Arg Asn Leu Thr Ala Asp Glu Asn Leu Tyr Pro Asp Pro Ser Ala Arg
                500                 505                 510
Leu Leu Met Arg Arg Arg Val Val Ala Pro Pro Gln Ala Ser Ile Thr
                515                 520                 525
Pro Gln Leu Val Ser Ala
    530

<210> SEQ ID NO 74
<211> LENGTH: 746
<212> TYPE: PRT
<213> ORGANISM: Aspergillus nidulans

<400> SEQUENCE: 74

Met Tyr Pro Trp Ser Ser Thr Gly Thr Ser Pro Phe Ser His Pro Asp
1               5                   10                  15
Asn Glu Gly Ala Glu Ser Gly Asp Met Ser Met Gly Glu Glu Gln Gln
                20                  25                  30
```

```
Gln Pro His Gln Arg Arg Gln Lys Phe Asn Asn Leu Arg Ala Cys Gln
         35                  40                  45

Ser Cys Arg Ala Ser Lys Val Arg Cys Asp Gln Pro Asn Pro Gly Met
 50                  55                  60

Pro Cys Leu Arg Cys Gln Lys Ser Gly Lys Pro Cys Val Asp Ala Ala
 65                  70                  75                  80

Ser Gln Pro Gly Lys Arg Gln Arg Gln Pro Ile Asn Ser Ile Leu Glu
             85                  90                  95

Met Glu Ser Arg Ile Glu Thr Ile Leu Ser Ser Ala Glu Leu Gln Asp
             100                 105                 110

Ser Ala Gly Asp Gly Glu Thr Ala His Ser Thr Ala Leu Arg Ser Pro
             115                 120                 125

Ser Gln Leu Ser His His Ile Gln Pro Phe Gln His Leu Pro Met Gly
             130                 135                 140

Phe Ala Ile Pro Phe Asn Gly Gly Asn Ser Gly Thr Glu Asp Leu Asn
145                 150                 155                 160

Ser Ser Ile Arg Ser Trp Leu Asn Asp Asn Ile Thr Asp Leu Asp Ala
             165                 170                 175

Arg Thr Thr Glu Thr Ile Phe Ser His Tyr Leu Thr Asn Met Val Pro
             180                 185                 190

Thr Phe Pro Val Val Val Phe Ala Thr Gly Thr Thr Ala Ala Asp Val
             195                 200                 205

Arg Arg Asn Asn Pro Ile Leu Phe Leu Ala Ile Leu Asp Val Ala Ser
             210                 215                 220

Ser Gly Phe Cys Ala Leu Glu Thr Gln Arg Lys Leu Arg Lys Leu Ile
225                 230                 235                 240

Val Gln Ala Tyr Val His Cys Met Leu Arg Thr Glu Gln Tyr Thr Leu
             245                 250                 255

Gly Leu Leu Gln Ala Leu Ile Val Ser Ala Thr Trp Tyr Arg Thr Ile
             260                 265                 270

Glu Pro Val Glu Pro Gly Glu Gln Met Asp Ile Tyr Gln Ile Ser His
             275                 280                 285

Thr Ala Ala Asn Met Ala Leu Ile Met Arg Leu Gly Glu Ser Leu Asn
             290                 295                 300

Ala Lys Ser Trp Gly Gly Pro Met Phe Pro Arg Arg Glu Met Lys Lys
305                 310                 315                 320

Gly Pro Gly Ser Ala Phe Gln Ala Asp Ser Leu Glu Ala Arg Arg Val
             325                 330                 335

Trp Leu Gly Cys His Tyr Ile Cys Ser Asn Thr Ser Met Ser Leu Arg
             340                 345                 350

Ala Pro Asn Ile Met Arg Trp Thr Arg Leu Met Asp Glu Cys Leu Glu
             355                 360                 365

Val Leu Glu Asn Ser Pro Ala Ala Leu Leu Ser Asp Arg Leu Leu Cys
370                 375                 380

Gln His Ile Arg Leu Gln His Ile Thr Glu Glu Phe Ala Met His Leu
385                 390                 395                 400

Ser Ala Glu Glu Ala Ser Ala Pro Ala Lys Ser Arg Ala Ile Gln Ile
             405                 410                 415

Gln Val Thr His Arg Ala Phe Lys Arg Gln Leu Ser Glu Trp Arg Arg
             420                 425                 430

Thr Val Gly Asp Gly Trp Asp Ala His Cys Thr Ala Thr Ser Asp Asp
             435                 440                 445
```

-continued

```
Val Pro Glu Asp Asn Ala Gln Arg Leu Thr Pro Pro Pro Ile Val
    450                 455                 460

Ala Ile Glu Pro His Ala Ile Thr Glu Phe Met Asp Thr Ile Asp Asn
465                 470                 475                 480

Ile Phe Arg Val Phe Thr Ser Leu Asp Met Ser Thr Ile Arg Ala Leu
                485                 490                 495

Pro Ala Met Tyr Leu Ile Arg Ile Ile Tyr Thr Phe Ile Ile Leu Val
            500                 505                 510

Lys Leu Tyr Phe Ala Ala Ala Lys Leu Pro Ala Gln Asp Ala Val Leu
        515                 520                 525

Gln Val Asp Gly Leu Gln Val Ser Arg Arg Phe Asn Arg Val Ile Gln
    530                 535                 540

Met Thr Ala Gly Trp Gly Pro Leu Trp Pro Ala Thr Lys Leu Thr Thr
545                 550                 555                 560

Val Phe Thr Lys Met Arg Ser Trp Phe Glu Ser Gly Gly Asp Asn Asn
                565                 570                 575

Cys Gln Arg Leu Gln Gln Ala Ala Ala Trp Leu Thr Gly Trp Glu Leu
            580                 585                 590

Lys Pro Pro Ser Gln Gly Arg Asp Ala His Ala Met Asn Met Ala Glu
        595                 600                 605

Val Val Ser Asp Asp Gly Ser Ile Val Ala Ser Ser Ser Arg Gly Pro
    610                 615                 620

Ala Ser Trp Val Pro Ser Leu Ala Ser Thr Asp Val Asp Thr Leu Ala
625                 630                 635                 640

Phe Ser His Glu Pro Pro Leu Gly Thr Glu Phe Ser Ile Ala Pro Pro
                645                 650                 655

Pro Phe Arg Ser Met Ser Cys Ala Thr Lys Ser Cys Ser Pro Gln Ala
            660                 665                 670

Gly Ala Ala Glu Phe Met His Asp Glu Glu Val Pro Leu Glu Gly Gln
        675                 680                 685

Arg Leu Gly Asp Leu Pro Asn Ile Asp Gln Met Asp Asp Val Gly Met
    690                 695                 700

Asp Trp Ser Gln Tyr Thr Asn Met Gly Phe Asp Leu Tyr Asn Leu Asp
705                 710                 715                 720

Ala Pro Phe Leu Pro Asn Pro Pro Ser Gly Phe Asp Pro Asp Ala Ala
                725                 730                 735

Met Lys Asp Asn Cys Ala Asp Arg Asn Thr
            740                 745
```